(12) United States Patent
Selles et al.

(10) Patent No.: US 8,084,395 B2
(45) Date of Patent: Dec. 27, 2011

(54) 4-AZA INDOLE DERIVATIVES AND THEIR USE AS FUNGICIDES

(75) Inventors: Patrice Selles, Greensboro, NC (US); Fredrik Cederbaum, Schaffhauserstrasse (CH); Florence Marie-Emilie Bonnaterre, Les Lilas (FR); William Guy Whittingham, Bracknell (GB); Mafalda Nina, Shaffhauserstrasse (CH); Jane Elizabeth Wibley, Bracknell (GB)

(73) Assignee: Syngenta Crop Protection, Inc., Greensboro, NC (US)

( * ) Notice: Subject to any disclaimer, the term of this patent is extended or adjusted under 35 U.S.C. 154(b) by 0 days.

(21) Appl. No.: 12/597,044

(22) PCT Filed: Apr. 16, 2008

(86) PCT No.: PCT/GB2008/001348
§ 371 (c)(1),
(2), (4) Date: Mar. 1, 2010

(87) PCT Pub. No.: WO2008/132434
PCT Pub. Date: Nov. 6, 2008

(65) Prior Publication Data
US 2010/0184598 A1  Jul. 22, 2010

(30) Foreign Application Priority Data
Apr. 26, 2007 (GB) .................................. 0708141.7

(51) Int. Cl.
*A01N 25/00* (2006.01)
(52) U.S. Cl. ................................. 504/116.1
(58) Field of Classification Search .................. None
See application file for complete search history.

(56) References Cited

U.S. PATENT DOCUMENTS
2001/0044538 A1* 11/2001 Cheng et al. .................. 544/238
2006/0135516 A1* 6/2006 Berdini et al. ............. 514/234.2

FOREIGN PATENT DOCUMENTS
WO  9920624  4/1999
WO  2007085660  8/2007

OTHER PUBLICATIONS

Christian Pillonel, Evaluation of Phenylaminopyrimidines as Antifungal Protein Kinase Inhibitors, 61 Pest Manag. Sci., 1069-76 (2005).*
Gill Adrian, L., et al.: "Identification of Novel p38.alpha. MAP Kinase Inhibitors Using Fragment-Based Lead Generation:" Journal of Medicinal Chemistry, American Chemical Society, Washington, US, [Online] vol. 48, No. 2, Jan. 1, 2005, pp. 414-426, XP009120797.
Koolman H. et al.: "Syntheses of novel 2,3-diaryl-substituted 5-cyano-4-azainodles exhibiting c-Met inhibition activity"; Bioorganic & Medicinal Chemistry Letters, Pergamon, Elsevier Science, GB, vol. 19, No. 7, Apr. 1, 2009, pp. 1879-1882, XP025974880, ISSN: 0960-894X.
Papalia G A et al.: "Thermodynamic characterization of pyrazole and azaindole derivatives binding to p38 mitogen-activated protein kinase using Biacore T100 technology and van't Hoff analysis;" Analytical Biochemistry, Academic Press Inc., New York, vol. 383, No. 2, Dec. 15, 2008, pp. 255-264, XP025585791.
Ichihara Y et al.: "Indole type broad spectrum agricultural fungicide—esp effective against powdery mildew of cucumber:" 1981. WPI/Thomson Host—WPI / Thomson, XP002436093.
Adachi A et al: "Agricultural fungicide contg. 3-aminoalkyl-indole-2-carboxylic acid—for control of rice blast, mildew wheat rust etc." WPI / Thomson-Host—WPI/ Thomson, 1985, XP002436092.
Zook M. et al.: "Origin of the thiazole ring of camalexin, a phytoalexin from *Arabidopsis thliana*;" Plant Physiology, American Society of Plant Physiologists, Rockville, MD, US, vol. 113, Jan. 1, 1997, pp. 463-468, XP002436086, ISSN: 0032-0889.
Dekker W. H. et al.: "Structure-activity relationships of some antifungal indoles;" Journal of Agricultural and Food Chemistry, American Chemical Society, Washington, US, vol. 23, No. 4, Jan. 1, 1975, pp. 785-791, XP002436082, ISSN: 0021-8561.
Pedras M. S. C. et al.: "Metabolism and detoxification of phytoalexins and analogs by phytopathogenic fungi;" Phytochemistry, Pergamon Press, GB, vol. 66, No. 4, Feb. 1, 2005, pp. 391-411, XP004735326.
Pedras M. S. C. et al.: "Phytoalexins from crucifers: synthesis, biosynthesis, and biotransformation;" Phytochemistry, Pergamon Press, GB, vol. 53, No. 2, Jan. 1, 2000, p. 161-176, XP004291272, ISSN: 0031-9422.

* cited by examiner

*Primary Examiner* — Janet Andres
*Assistant Examiner* — Timothy R Rozof
(74) *Attorney, Agent, or Firm* — James Cueva

(57) ABSTRACT

The present invention relates to a method of preventing and/or controlling fungal infection in plants and/or plant propagation material comprising applying to the plant or plant propagation material a fungicidally effective amount of a compound of formula (I) or a salt of N-oxide thereof. In addition, the present invention also relates to a compound of formula (I).

5 Claims, No Drawings

4-AZA INDOLE DERIVATIVES AND THEIR USE AS FUNGICIDES

This application is a 371 of International Application No. PCT/GB2008/001348 filed Apr. 16, 2008, which claims priority to GB 0708141.7 filed Apr. 26, 2007, the contents of which are incorporated herein by reference.

The present invention relates to novel fungicidally active 4-aza-indoles, compositions comprising these novel compounds and their use in methods for the control and/or prevention of fungal infection in plants. In addition, the invention relates to processes for preparing the novel compounds of the invention.

Certain 4-aza-indoles and their use in the prevention and treatment of human and animal disease, although not that caused by fungi, are described in WO 99/20624. Similar compounds are described in WO 03/06629, WO 2006/014325 and WO 98/22457, the latter also disclosing their use as anti-inflammatory agents.

It has now been found that certain 4-aza-indoles have fungicidal activity and, in particular, activity against plant pathogenic fungi.

Accordingly, the present invention provides a method of preventing and/or controlling fungal infection in plants and/or plant propagation material comprising applying to the plant or plant propagation material a fungicidally effective amount of a compound of formula (I):

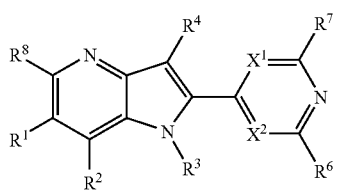
(I)

wherein:
$X^1$ is N or CH;
$X_2$ is N or $CR^5$;
$R^1$ and $R^2$ are, independently:
(i) hydrogen, halogen, hydroxyl, cyano or nitro,
(ii) optionally substituted alkyl, alkenyl or alkynyl,
(iii) optionally substituted aryl, heteroaryl, cyclyl or heterocyclyl, or
(iv) —C(O)$R^{10}$, —C(O)N$R^{10}R^{11}$, —C(S)N$R^{10}R^{11}$, —C(NO$R^{10}$)$R^{11}$, —C(O)O$R^{10}$, —O$R^{10}$, —S$R^{10}$, —S(O)$R^{10}$, —S(O)N$R^{10}R^{11}$, —S(O)$_2$N$R^{10}R^{11}$, —S(O)$_2R^{10}$, —N$R^{10}R^{11}$, —P(O)(O$R^{10}$)(O$R^{11}$) or —OP(O)(O$R^{10}$)(O$R^{11}$);

$R^3$ is:
(i) hydrogen, hydroxyl, cyano or nitro,
(ii) optionally substituted alkyl, alkenyl, allenyl, alkynyl or haloalkyl,
(iii) optionally substituted aryl, heteroaryl, cyclyl or heterocyclyl or heteroaralkyl or
(iv) —C(O)O$R^{12}$, —O$R^{12}$, —OC(O)$R^{12}$, —S(O)$_2R^{12}$ or —N$R^{12}R^{13}$;

$R^4$ is:
(i) hydrogen, halogen, hydroxyl, cyano or nitro,
(ii) optionally substituted alkyl, alkenyl, allenyl, alkynyl or haloalkyl,
(iii) optionally substituted aryl, heteroaryl, cyclyl or heterocyclyl or
(iv) —C(O)$R^{14}$, —C(O)O$R^{14}$, —C(NO$R^{14}$)$R^{15}$, —O$R^{14}$, —S$R^{14}$, —S(O)N$R^{14}R^{15}$, —S(O)$_2R^{14}$, or —N$R^{14}R^{15}$;

$R^5$ is:
(i) hydrogen, halogen, hydroxyl, cyano or nitro,
(ii) optionally substituted alkyl, alkenyl or alkynyl,
(iii) —C(O)$R^{16}$, —C(O)O$R^{16}$, —O$R^{16}$, —S$R^{16}$, —S(O)$R^{16}$, —S(O)N$R^{16}R^{17}$, —S(O)$_2R^{16}$, or —N$R^{16}R^{17}$;

$R^6$ is hydrogen, halogen, cyano, —C(O)O$R^{18}$, —S$R^{18}$, —N$R^{18}R^{19}$, —C(O)N$R^{18}R^{19}$ or —N=C$R^{20}$, —C(=N$R^{18}$)N$R^{19}R^{20}$ or optionally substituted aryl, heteroaryl, cyclyl or heterocyclyl;

$R^7$ and $R^8$ independently, independently, hydrogen, halogen, hydroxyl, cyano, nitro, —N$R^{21}R^{22}$ or optionally substituted alkyl;

$R^{10}$, $R^{11}$, $R^{14}$, $R^{15}$, $R^{16}$ and $R^{17}$ are, independently, hydrogen, halogen, hydroxyl, cyano, nitro, optionally substituted alkyl, alkoxy, alkenyl or alkynyl, or optionally substituted aryl, heteroaryl, cyclyl or heterocyclyl;

$R^{12}$ and $R^{13}$ are, independently, hydrogen, halogen, hydroxyl, cyano, nitro, —N$R^{21}R^{22}$, optionally substituted alkyl, alkoxy, alkenyl or alkynyl, or optionally substituted aryl, heteroaryl, cyclyl or heterocyclyl;

$R^{18}$ and $R^{19}$ are, independently,
(i) hydrogen,
(ii) optionally substituted alkyl, alkenyl or alkynyl,
(iii) optionally substituted aryl, heteroaryl, cyclyl or heterocyclyl, or
(iv) —C(S)$R^{23}$—C(O)$R^{23}$, —SO$_2R^{23}$, —C(O)O$R^{23}$, —O$R^{23}$ or C(O)N$R^{23}R^{24}$;

$R^{20}$ is hydroxyl, optionally substituted alkyl or alkoxy or —N$R^{21}$K or —N=C$R^{21}R^{22}$;

$R^{21}$ and $R^{22}$ are, independently, hydrogen, optionally substituted alkyl, alkenyl or alkynyl, optionally substituted cyclyl, heterocyclyl, aryl, or heteroaryl or aralkyl or —C(O)O$R^{25}$;

$R^{23}$ and $R^{24}$ are, independently, hydrogen, hydroxyl, optionally substituted alkyl, alkenyl or alkynyl, or optionally substituted aryl, heteroaryl, cyclyl or heterocyclyl or aralkyl; and $R^{25}$ is optionally substituted alkyl, alkenyl or alkynyl;

and/or
independently, (i) $R^1$ and $R^2$, (ii) $R^1$ and $R^3$ (iii) $R^2$ and $R^3$, (iv) $R^3$ and $R^5$, (v) $R^5$ and $R^6$, (vi) $R^5$ and $R^{18}$, (vii) $R^5$ and $R^{19}$, (viii) $R^{14}$ and $R^{15}$ and (ix) $R^{18}$ and $R^{19}$ form an optionally substituted aryl, heteroaryl, cyclyl or heterocyclyl group containing from 5 to 18 ring atoms;

or a salt of N-oxide thereof.

Unless otherwise stated, the following terms used in the specification and claims have the meanings given below:

"Alkyl" means a linear saturated monovalent hydrocarbon radical of one to eight carbon atoms or a branched saturated monovalent hydrocarbon radical of three to eight carbon atoms, e.g. methyl, ethyl, n-propyl, iso-propyl, n-butyl, sec-butyl, iso-butyl, tert-butyl, n-pentyl, n-hexyl and the like. Preferably, linear alkyl groups contain one to six carbon atoms, more preferably one to four carbon atoms and most preferably are selected from methyl, ethyl or n-propyl. Preferably, branched alkyl groups contain three to six carbon atoms and more preferably are selected from iso-propyl, sec-butyl, iso-butyl or tert-butyl.

"Alkenyl" means a linear monovalent saturated hydrocarbon radical of two to eight carbon atoms, or a branched monovalent hydrocarbon radical of three to eight carbon atoms containing at least one double bond, e.g. ethenyl, propenyl and the like. Where appropriate, an alkenyl group can be of either the (E)- or (Z)-configuration. Preferably, linear alkenyl groups contain two to six carbon atoms and more preferably are selected from ethenyl, prop-1-enyl, prop-2-enyl, prop-1,2-dienyl, but-1-enyl, but-2-enyl, but-3-enyl, but-1,2-dienyl and but-1,3-dienyl. Preferably, branched alkenyl groups contain three to six carbon atoms and more preferably are selected from 1-methylethenyl, 1-methylprop-1-enyl, 1-methylprop-2-enyl, 2-methylprop-1-enyl and 2-methylprop-2-enyl.

"Allenyl" means a linear monovalent saturated hydrocarbon radical of three to eight carbon atoms, or a branched monovalent hydrocarbon radical of three to eight carbon atoms containing at least two double bonds between three contiguous carbon atoms, e.g. propa-1,2 dienyl, penta-1,2 dienyl, penta-2,3 dienyl, hexa-1,2-dienyl and the like. Where appropriate, an alkenyl group can be of either the (R)- or (S)-configuration. Preferred is propa-1,2-dienyl.

"Alkynyl" means a linear monovalent saturated hydrocarbon radical of two to eight carbon atoms, or a branched monovalent hydrocarbon radical of four to eight carbon atoms, containing at least one triple bond, e.g. ethynyl, propynyl and the like. Preferably, linear alkynyl groups contain two to six carbon atoms and more preferably are selected from ethynyl, prop-1-ynyl, prop-2-ynyl, but-1-ynyl, but-2-ynyl and but-3-ynyl. Preferably, branched alkynyl groups contain four to six carbon atoms and more preferably are selected from 1-methylprop-2-ynyl, 3-methylbut-1-ynyl, 1-methylbut-2-ynyl, 1-methylbut-3-ynyl and 1-methylbut-3-ynyl.

"Alkylene" means a linear saturated divalent hydrocarbon radical of one to six carbon atoms or a branched saturated divalent hydrocarbon radical or three to six carbon atoms, e.g. methylene, ethylene, propylene, 2-methylpropylene and the like. Preferred alkylene groups are the divalent radicals of the alkyl groups defined above.

"Alkenylene" means a linear divalent hydrocarbon radical of two to six carbon atoms or a branched divalent hydrocarbon radical of three to six carbon atoms, containing at least one double bond, e.g. ethenylene, propenylene and the like. Preferred alkenylene groups are the divalent radicals of the alkenyl groups defined above.

"Cyclyl" means a monovalent cyclic hydrocarbon radical of three to eight ring carbons, preferably three to six ring carbons, e.g. cyclopropyl, cyclohexyl and the like. Cyclyl groups may be fully saturated or mono- or di-unsaturated. Preferably, cyclyl groups contain three to six ring carbons, more preferably they are selected from cyclopropyl, cyclobutyl, cyclopentyl and cyclohexyl. Mono-unsaturated cyclyl groups are preferably selected from cyclobutenyl, cyclopentenyl and cyclohexenyl.

"Heterocyclyl" means a cyclyl radical containing one, two or three ring heteroatoms selected from N, O or $S(O)_n$ (where n is an integer from 0 to 2), the remaining ring atoms being carbon where one or two carbon atoms may optionally be replaced by a carbonyl group. Examples of such rings include, but are not limited to, oxirane, oxetane, tetrahydrofuran, tetrahydropyran, 1,3-dioxolane, 1,4-dioxane, aziridine, azetidine, pyrrolidine, piperidine, oxazinane, morpholine, thiomorpholine, imidazolidine, pyrazolidine and piperazine. More preferably, the heterocyclyl group contains three to five ring atoms including one O and/or one N ring atom.

"Aryl" means a monovalent monocyclic or bicyclic aromatic hydrocarbon radical of six to ten ring carbons atoms. Suitable aryl groups include phenyl and naphthyl, in particular, phenyl.

"Heteroaryl" means a monovalent monocyclic or bicyclic aromatic hydrocarbon radical of five to ten ring atoms, preferably five or six ring atoms, containing one, two, three or four ring heteroatoms selected, independently, from N, O or S, the remaining ring atoms being carbon. Examples of heteroaryl groups include, but are not limited to pyridyl, pyrimidinyl, pyrazolyl, thiazolyl, thiophenyl, isoxazolyl, and tetrazolyl groups.

"Alkoxy" means a radical —OR, where R is optionally substituted alkyl, alkenyl or alkynyl or an optionally substituted cyclyl, heterocyclyl, aryl or heteroaryl group or an aralkyl or heteroaralkyl group. Preferably, alkoxy groups are selected from methoxy, ethoxy, 1-methylethoxy, propoxy, 1-methylpropoxy and 2-methylpropoxy. More preferably alkoxy means methoxy or ethoxy.

"Halo" or "halogen" means fluoro, chloro, bromo or iodo, preferably chloro or fluoro.

"Haloalkyl" means alkyl as defined above substituted with one or more of the same or different halo atoms. Examples of haloalkyl groups include, but are not limited to fluoromethyl, difluoromethyl, trifluoromethyl, 2-fluoroethyl, 2-trifluoroethyl, 2-chloro-ethyl, 2-iodoethyl, 3-fluoropropyl, 3-chloropropyl, 2-trifluoro-1-chloroethyl and 1-difluoro-2-difluoro-3-trifluoropropyl.

"Haloalkenyl" means alkenyl as defined above substituted with one or more of the same or different halo atoms. Examples of haloalkenyl groups include, but are not limited to 2-dibromoethenyl, 2-fluoro-2-bromoethenyl, 5-bromopent-3-enyl and 3 dichloroprop-2-enyl.

"Aralkyl" means a radical —$R^aR^b$ where $R^a$ is an alkylene or alkenylene group and $R^b$ is an aryl group as defined above.

"Heteroaralkyl" means a radical —$R^aR^b$ where $R^a$ is an alkylene or alkenylene group and $R^b$ is a heteroaryl group as defined above.

"Acyl" means —C(O)R, wherein R is hydrogen, optionally substituted alkyl, alkenyl or alkynyl or optionally substituted cyclyl, heterocyclyl, aryl or heteroaryl.

"Acyloxy" means a radical —OC(O)R where R is hydrogen, optionally substituted alkyl, alkenyl or alkynyl or optionally substituted cyclyl, heterocyclyl, aryl or heteroaryl.

The groups defined above, in particular, alkyl, alkenyl, alkynyl, cyclyl, heterocyclyl, aryl and heteroaryl groups, may be optionally substituted by one or more substituents independently selected from halogen, hydroxyl, cyano, alkyl (optionally substituted by cyano), haloalkyl, alkenyl, haloalkenyl, alkynyl (optionally substituted by —C(O)OR), haloalkynyl, cyclyl (optionally substituted by cyano, halogen, hydroxyl or methyl), heterocyclyl, aryl (optionally substituted by halogen), heteroaryl, alkoxy (optionally substituted by alkoxy or acyl), —C(O)R, —C(O)OR, —SR, —S(O)R, —S(O)$_2$R, —S(O)NRR', —OS(O)NRR', —P(O)(OR)(OR'), —O(P)(O)(OR)(OR'), —NRR', —NRC(O)OR', —C(O)NRR', —O—N═CRR' or trialkylsilyl, wherein R and R' are, independently, hydrogen or alkyl, alkoxy, haloalkyl, alkenyl, haloalkenyl, alkynyl, cyclyl, heterocyclyl, aryl or heteroaryl. In particular, R and R' are, independently, hydrogen or alkyl (in particular, methyl or ethyl). Preferred optional substituents are alkoxy (in particular, methoxy or ethoxy), hydroxyl, cyano, halogen (in particular, fluoro, chloro or bromo), heterocyclyl (in particular, oxirane or tetrahydrofuran), heteroaryl (in particular, pyridyl), —C(O)OR (wherein R is hydrogen or alkyl (in particular, methyl or ethyl)) and trialkylsilyl (in particular, trimethylsilyl).

The compounds of formula (I) may exist in different geometric or optical isomeric forms or in different tautomeric forms. One or more centres of chirality may be present, in which case compounds of the formula (I) may be present as pure enantiomers, mixtures of enantiomers, pure diastereomers or mixtures of diastereomers. There may be double bonds present in the molecule, such as C═C or C═N bonds, in which case compounds of formula (I) may exist as single isomers of mixtures of isomers. Centres of tautomerisation may be present. This invention covers all such isomers and tautomers and mixtures thereof in all proportions as well as isotopic forms such as deuterated compounds.

Suitable salts of the compounds of formula (I) include acid addition salts such as those with an inorganic acid such as hydrochloric, hydrobromic, sulfuric, nitric or phosphoric acid, or an organic carboxylic acid such as oxalic, tartaric, lactic, butyric, toluic, hexanoic or phthalic acid, or a sulphonic acid such as methane, benzene or toluene sulphonic acid. Other examples of organic carboxylic acids include haloacids such as trifluoroacetic acid.

N-oxides are oxidised forms of tertiary amines or oxidised forms of nitrogen containing heteroaromatic compounds. They are described in many books for example in "Heterocyclic N-oxides" by Angelo Albini and Silvio Pietra, CRC Press, Boca Raton, Fla., 1991.

In particularly preferred embodiments of the invention, the preferred groups for $X^1$ and $X^2$ and $R^1$ to $R^{25}$, in any combination thereof, are as set out below.

Preferably, $X^1$ is CH.

Preferably, $X^2$ is $CR^5$. More preferably, $X^2$ is CH.

Preferably, $R^1$ is hydrogen, halogen, cyano, optionally substituted $C_{1-6}$ alkyl, $C_{2-6}$ alkenyl or $C_{2-6}$ alkynyl, optionally substituted aryl or —$C(O)R^{10}$, wherein the optional substituents in all cases are as defined above and, more preferably, are selected from hydroxyl, alkoxy, halogen or trialkylsilyl. More preferably, $R^1$ is hydrogen, halogen, cyano or optionally substituted $C_{1-6}$ alkyl or $C_{2-6}$ alkynyl (in particular, the $C_{2-6}$ alkynyl is 2-trimethylsilyl-ethynyl). Even more preferably, $R^1$ is hydrogen, chloro, bromo, cyano or methyl. Most preferably, $R^1$ is hydrogen, chloro or methyl.

Preferably, $R^2$ is hydrogen or $C_{1-6}$ alkyl. More preferably, $R^2$ is hydrogen or methyl. Most preferably, $R^2$ is hydrogen.

Preferably, $R^3$ is hydrogen, hydroxyl, —$C(O)R^{12}$, —$OR^{12}$, —$C(O)OR^{12}$, —$OC(O)R^{12}$, —$S(O)_2R^{12}$, optionally substituted $C_{1-6}$ alkyl, $C_{2-6}$ alkenyl, $C_{3-6}$ allenyl, $C_{2-6}$ alkynyl or optionally substituted saturated cyclyl, wherein the optional substitutents in all cases are as defined above and, more preferably, are selected from cyano, halogen, hydroxyl, $C_{1-4}$ alkyl, $C_{2-4}$ alkenyl, alkoxy (optionally substituted by alkoxy or acyl), cyclyl, heterocyclyl, aryl, heteroaryl, —$NH_2$, trialkylsilyl, —$C(O)R$ or —$C(O)OR$ (wherein R is hydrogen, methyl or ethyl). More preferably, $R^3$ is hydrogen, —$OR^{12}$ or optionally substituted $C_{1-6}$ alkyl, $C_{2-4}$ alkenyl, $C_{3-4}$ allenyl or $C_{2-4}$ alkynyl. Most preferably, $R^3$ is hydrogen, cyanomethyl, aminoethyl, aminopropyl, prop-2-enyl, prop-2-ynyl, propa-1,2-dienyl, methoxymethyl, 2-fluoromethyl, —$OCH_2C\equiv H$, —$OCH_2OCH_3$, —$OCH_2CN$, —$OCH(CH_3)CN$.

Preferably, $R^4$ is hydrogen, halogen, optionally substituted $C_{2-6}$ alkynyl or optionally substituted aryl or heteroaryl, wherein the optional substituents are as defined above and, more preferably, are selected from hydroxyl, halogen (in particular, fluoro or chloro), haloalkyl, acyl or $C_{1-4}$ alkyl (in particular, methyl). More preferably, $R^4$ is optionally substituted phenyl or optionally substituted heteroaryl. Even more preferably, $R^4$ is optionally substituted phenyl. Even more preferably, $R^4$ is phenyl, 3-methylphenyl, trifluoromethylphenyl, 4-chlorophenyl, 2-fluorophenyl, 3-fluorophenyl, 4-fluorophenyl, 2,5-difluorophenyl or 3-methyl-4-fluorophenyl. Most preferably, $R^4$ is phenyl or 4-fluorophenyl.

Preferably $R^5$ is hydrogen, halogen, optionally substituted $C_{1-6}$ alkyl, $C_{2-6}$ alkenyl or $C_{2-6}$ alkynyl, or forms an optionally substituted aryl, hetearyl, cyclyl or hetercycyl ring with $R^6$, wherein the optional substituents in all cases are as defined above and, more preferably, are selected from halogen, cyano, hydroxyl, haloalkyl or $C_{1-4}$ alkyl. Preferably, the ring formed with $R^6$ is a 5 or 6 membered heterocycle. More preferably, $R^5$ is hydrogen or halogen. Most preferably, $R^5$ is hydrogen.

Preferably $R^6$ is hydrogen, chloro, —$C(O)OR^{18}$, —$NR^{18}R^{19}$, —$N=CR^{20}$ or forms an optionally substituted aryl, heteroaryl, cyclyl or heterocycyl ring with $R^5$ as defined above. More preferably, $R^6$ is hydrogen or —$NR^{18}R^{19}$. More preferably, $R^6$ is —$NHR^{19}$. More preferably, $R^6$ is —$NHC(O)R^{23}$.

Preferably $R^7$ and $R^8$ are, independently, hydrogen, hydroxyl, cyano, —$NR^{21}R^{22}$ or optionally substituted $C_{1-6}$ alkyl, wherein the optional substituents are as defined above and, more preferably, are selected from halogen, cyano, hydroxyl or haloalkyl. More preferably, $R^7$ and $R^8$ are, independently hydrogen, hydroxyl or —$NR^{21}R^{22}$. Most preferably, $R^7$ and $R^8$ are both hydrogen.

Preferably, $R^{10}$, $R^{11}$, $R^{14}$, $R^{15}$, $R^{16}$ and $R^{17}$ are, independently, hydrogen or optionally substituted $C_{1-6}$ alkyl, $C_{2-6}$ alkenyl or $C_{2-6}$ alkynyl, wherein the optional substituents are as defined above and, more preferably, are hydroxyl, halogen, cyano or alkoxy. More preferably $R^{10}$, $R^{11}$, $R^{14}$, $R^{15}$, $R^{16}$ ad $R^{17}$ are, independently, hydrogen or optionally substituted $C_{1-3}$ alkyl. Most preferably, $R^{10}$, $R^{11}$, $R^{14}$, $R^{15}$, $R^{16}$ and $R^{17}$ are, independently, hydrogen, methyl or ethyl.

Preferably $R^{12}$ and $R^{13}$ are, independently, optionally substituted $C_{1-6}$ alkyl, $C_{2-6}$ alkenyl or $C_{2-6}$ alkynyl or optionally substituted $C_{3-6}$ cyclyl, wherein the optional substituents in all cases are as defined above and, more preferably are hydroxyl, halogen, cyano, alkoxy, cyclyl (optionally substituted with hydroxyl or methyl), —$C(O)OR$, —$OS(O)NRR'$ (wherein R and R' are, independently, hydrogen, alkyl, alkenyl or alkynyl). More preferably, $R^{12}$ and $R^{13}$ are, independently, optionally substituted $C_{1-4}$ alkyl, $C_{2-4}$ alkenyl or $C_{2-4}$ alkynyl. Most preferably, $R^{12}$ and $R^{13}$ are, independently, cyanomethyl, prop-2-enyl or prop-2-ynyl.

Preferably $R^{18}$ is hydrogen, optionally substituted $C_{1-6}$ alkyl, $C_{2-6}$ alkenyl or $C_{2-6}$ alkynyl, —$C(O)R^{23}$, —$C(O)OR^{23}$, —$S(O)_2R^{23}$ or —$C(O)NR^{23}R^{24}$ or forms an optionally substituted heterocyclyl ring with $R^{19}$, wherein the optional substituents in all cases are as defined above and, more preferably are selected from hydroxyl, cyano, halogen or alkoxy. More preferably, $R^{18}$ is hydrogen, $C_{1-4}$ substituted alkyl, $C_{2-4}$ alkenyl, or $C_{2-4}$ alkynyl. Preferably the $C_{1-4}$ alkyl group is ethyl or iso-propyl. Preferably, the $C_{2-4}$ alkenyl group is propen-2-enyl. Preferably, the $C_{2-4}$ alkynyl group is prop-2ynyl or but-2-ynyl. Most preferably, $R^{18}$ is hydrogen.

Preferably $R^{19}$ is hydrogen, —$C(S)R^{23}$, —$C(O)R^{23}$, —$C(O)OR^{23}$, —$S(O)_2R^{23}$ or —$C(O)NR^{23}R^{24}$ optionally substituted $C_{1-6}$ alkyl, $C_{2-6}$ alkenyl or $C_{2-6}$ alkynyl, optionally substituted aryl, heteroaryl, cyclyl or heterocyclyl or forms an optionally substituted heterocyclyl ring with $R^{18}$, wherein the optional substituents in all case are as defined above and, more preferably, are selected from hydroxyl, cyano, halogen, alkoxy, cyclyl or heterocyclyl. More preferably, $R^{19}$ is hydrogen, —$C(S)R^{23}$, —$C(O)R^{23}$ or —$C(O)OR^{23}$ or optionally substituted $C_{1-4}$ alkyl. Preferably, the optionally substituted $C_{1-4}$ alkyl is iso-butyl. Most preferably, $R^{19}$ is hydrogen, —$C(O)R^{23}$ or —$C(O)OR^{23}$.

Preferably, $R^{20}$ is —$NR^{21}R^{22}$.

Preferably, $R^{21}$ and $R^{22}$ are, independently, hydrogen, optionally substituted $C_{1-4}$ alkyl or —$C(O)OR^{25}$, wherein the optional substituents are as defined above and, more preferably, are selected from hydroxyl, cyano, halogen, alkoxy, acyl, cyclyl or heterocyclyl. More preferably, $R^{21}$ and $R^{22}$ are, independently, hydrogen or optionally substituted $C_{1-4}$ alkyl. Most preferably, $R^{21}$ and $R^{22}$ are, independently, hydrogen, methyl or ethyl.

Preferably $R^{23}$ and $R^{24}$ are, independently, hydrogen, hydroxyl, optionally substituted $C_{1-6}$ alkyl, $C_{2-6}$ alkenyl or $C_{2-6}$ alkynyl or optionally substituted cyclyl or aryl, wherein the optional substituents in all cases are as defined above and, more preferably, are hydroxyl, halogen, cyano, $C_{1-4}$ alkyl, alkoxy, haloalkenyl, cyclyl or —C(O)OR (wherein R is cyclyl). Preferably, the aryl group is optionally substituted phenyl. More preferably, the aryl group is 3-halophenyl or 4-halophenyl. More preferably, $R^{23}$ and $R^{24}$ are, independently, hydrogen, optionally substituted $C_{1-6}$ alkyl or $C_{2-6}$ alkenyl or an optionally substituted saturated or mono-unsaturated cyclyl group. Even more preferably, $R^{23}$ and $R^{24}$ are, independently, optionally substituted $C_{1-6}$ alkyl or an optionally substituted $C_{3-6}$ saturated cyclyl group. Preferably the optionally substituted $C_{1-6}$ alkyl is methyl, ethyl or iso-propyl. Preferably, the $C_{3-6}$ saturated cyclyl group is a cyclopropyl or cyclobutyl group, which may be substituted with one or more substituents being selected from cyano, halogen (preferably fluoro), $C_{1-4}$ alkyl (preferably methyl) or haloalkenyl.

Preferably, $R^{25}$ is $C_{1-4}$ alkyl. More preferably, $R^{25}$ is methyl, ethyl, propyl or 2-dimethylethyl.

In a particularly preferred embodiment, when $R^3$ is hydrogen, $R^6$ is other than hydrogen. More preferably, $R^3$ is hydrogen and $R^6$ is —$NR^{18}R^{19}$. More preferably, $R^3$ is hydrogen and $R^6$ is —$NHR^{19}$. More preferably, $R^3$ is hydrogen and $R^6$ is —$NHC(O)R^{23}$.

In an alternative preferred embodiment, $R^6$ is hydrogen and $R^3$ is other than hydrogen. More preferably, $R^6$ is hydrogen and $R^3$ is —$OR^{12}$ or optionally substituted $C_{1-6}$ alkyl, $C_{2-4}$ alkenyl, $C_{3-4}$ allenyl or $C_{2-4}$ alkynyl. Most preferably, $R^6$ is hydrogen and $R^3$ is cyanomethyl, aminoethyl, aminopropyl, prop-2-enyl, prop-2-ynyl, propa-1,2-dienyl, methoxymethyl, 2-fluoromethyl, —$OCH_2C$ H, —$OCH_2OCH_3$, —$OCH_2CN$, —$OCH(CH_3)CN$.

In a particular embodiment, the method of the invention utilises a compound of formula (Ia):

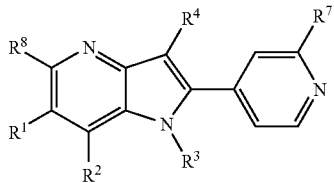

(Ia)

wherein $R^1$, $R^2$, $R^3$, $R^4$, $R^7$ and $R^8$ are as defined above and, preferably:

$R^1$ is hydrogen, halogen, cyano, optionally substituted $C_{1-6}$ alkyl (in particular, optionally substituted $C_{1-4}$ alkyl and, most particularly, optionally substituted methyl or ethyl, wherein the optional substitutent is as defined above and more preferably is hydroxyl, e.g. 1-hydroxylethyl) or —$C(O)R^{10}$ and $R^{10}$ is hydrogen or $C_{1-4}$ alkyl;

$R^2$, $R^7$ and $R^8$ are, independently, hydrogen, halogen or $C_{1-4}$ alkyl;

$R^3$ is hydrogen, hydroxyl, cyano, optionally substituted $C_{1-6}$ alkyl, $C_{2-6}$ alkenyl, $C_{3-6}$ allenyl or $C_{2-6}$ alkynyl, —$NR^{12}R^{13}$, —$OR^{12}$ or —$C(O)R^{12}$, wherein:

(a) the optional substituents on the alkyl, alkenyl and alkynyl groups are as defined above and, more preferably, are independently selected from halo, cyano, hydroxyl, alkoxy (optionally substituted by alkoxy or acyl), $C_{1-4}$ alkyl, $C_{2-4}$ alkenyl, cyclyl, heterocyclyl, heteroaryl, —C(O)R, —C(O)OR and —SR, wherein R is hydrogen, $C_{1-4}$ alkyl, $C_{2-4}$ alkenyl or $C_{2-4}$ alkynyl, and (b) $R^{12}$ is optionally substituted alkyl, alkenyl, alkynyl or cyclyl, the optional substituents being as defined above and, more preferably, halo, cyano, hydroxyl, alkoxy, cyclyl, heterocyclyl, —C(O)R, —C(O)OR or —OS(O) NRR', wherein R and R' are, independently hydrogen or alkyl, and $R^4$ is optionally substituted aryl (in particular, phenyl or naphthyl), the optional substituents being as defined above and, more preferably halogen or $C_{1-4}$ alkyl.

More preferably, $R^1$ is hydrogen, halo or optionally substituted $C_{1-4}$ alkyl, wherein the optional substituent is preferably hydroxyl; $R^{10}$ is methyl or ethyl; $R^2$, $R^7$ and $R^8$ are, independently, hydrogen, methyl, ethyl or chloro; $R^3$ is hydrogen, —$OR^{12}$ or optionally substituted $C_{1-4}$ alkyl, $C_{2-4}$ alkenyl or $C_{2-4}$ alkynyl; and $R^4$ is phenyl, which is optionally substituted by at least one substituent selected from halogen and $C_{1-4}$ alkyl (in particular, methyl).

Even more preferably, $R^1$ is hydrogen, chloro or methyl; $R^2$, $R^7$ and $R^8$ are each hydrogen; $R^3$ is hydrogen, cyanomethyl, prop-2-enyl or prop-2-ynyl; and $R^4$ is phenyl, 2-fluorophenyl, 3-fluorophenyl, 4-fluorophenyl, 4-chlorophenyl, 3-methylphenyl or 3-methyl-4-fluorophenyl and most preferably is 4-fluorophenyl.

In a particular embodiment, the method of the invention utilises a compound of formula (Ib):

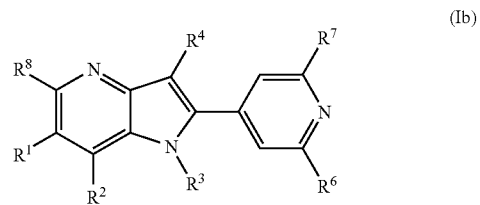

(Ib)

wherein $R^1$, $R^2$, $R^3$, $R^4$, $R^6$, $R^7$ and $R^8$ are as defined above and, preferably:

$R^1$ is hydrogen, halogen, optionally substituted $C_{1-6}$ alkyl or —$C(O)R^{10}$ and $R^{10}$ is hydrogen or $C_{1-4}$ alkyl;

$R^2$ is hydrogen or $C_{1-4}$ alkyl;

$R^3$ is hydrogen, hydroxyl, optionally substituted $C_{1-6}$ alkyl, $C_{2-6}$ alkenyl or $C_{2-6}$ alkynyl, —$C(O)R^{12}$ or —$OR^{12}$ and $R^{12}$ is optionally substituted $C_{1-4}$ alkyl or cyclyl, the optional substituents in all cases being as defined above and, more preferably, halogen, cyano, hydroxyl, alkoxy, cyclyl, heterocyclyl, —$NH_2$, trialkylsilyl or C(O)OR, wherein R is hydrogen, $C_{1-4}$ alkyl, $C_{2-4}$ alkenyl or $C_{2-4}$ alkynyl;

$R^4$ is optionally substituted aryl, the optional substituents being as defined above and, more preferably halogen or $C_{1-4}$ alkyl;

$R^6$ is halogen or —$NR^{18}R^{19}$ and
  (i) $R^{18}$ is hydrogen, —$C(O)R^{23}$, —$C(O)OR^{23}$ or optionally substituted $C_{1-4}$ alkyl, $C_{2-4}$ alkenyl or $C_{2-4}$ alkynyl and $R^{23}$ is optionally substituted $C_{1-4}$ alkyl and
  (ii) $R^{19}$ is hydrogen, optionally substituted $C_{1-4}$ alkyl, $C_{2-4}$ alkenyl or $C_{2-4}$ alkynyl, —$C(S)R^{23}$—$C(O)R^{23}$ or —$C(O)OR^{23}$ and $R^{23}$ is hydrogen, optionally substituted $C_{1-4}$ alkyl, $C_{2-4}$ alkenyl, $C_{2-4}$ alkynyl or $C_{3-6}$ cyclyl;

$R^7$ is hydrogen, halogen or $C_{1-4}$ alkyl; and $R^8$ is hydrogen, halogen, $C_{1-4}$ alkyl or $NR^{21}R^{22}$ and $R^{21}$ and $R^{22}$, are independently, hydrogen or $C_{1-4}$ alkyl.

More preferably, $R^1$ is hydrogen, halo or optionally substituted $C_{1-4}$ alkyl; $R^2$ is hydrogen or methyl; $R^3$ is hydrogen, optionally substituted $C_{1-4}$ alkyl, $C_{2-4}$ alkenyl or $C_{2-4}$ alkynyl or —$OR^{12}$; $R^4$ is phenyl, which is optionally substituted by at least one substituent selected from halogen and $C_{1-4}$ alkyl; $R^6$ is halogen or —NR$^{18}$R$^{19}$ and R$^{18}$ is hydrogen, prop-2-enyl or prop-2-ynyl and R$^{19}$ is —C(O)R$^{23}$ and R$^{23}$ is hydrogen, methyl, ethyl, iso-propyl, 1-methylethyl, 1-methylpropyl, 2-dimethylethyl, propyl, 1-methylethenyl, 2-methylprop-1-enyl, but-3-enyl, cyclopropyl, 1-methylcyclopropyl, 1-fluorocyclopropyl or cyclobutyl; R$^7$ is hydrogen, chloro, fluoro or methyl; and R$^8$ is hydrogen, chloro, methyl or 2-methoxy-1-ethylamino.

Even more preferably, R$^1$ is hydrogen, chloro or methyl; R$^2$ hydrogen or methyl; R$^3$ is hydrogen, cyanomethyl, prop-2-enyl or prop-2-ynyl; R$^4$ is 2-fluorophenyl, 3-fluorophenyl, 4-fluorophenyl, 4-chlorophenyl, 3-methylphenyl or 3-methyl-4-fluorophenyl and most preferably is 4-fluorophenyl; R$^6$ is —NR$^{18}$R$^{19}$ and R$^{18}$ is hydrogen and R$^{19}$ is —C(O)R$^{23}$ and R$^{23}$ is methyl, ethyl, iso-propyl, cyclopropyl, cyclobutyl or 1-methylcyclopropyl; R$^7$ hydrogen; and R$^8$ is hydrogen, chloro or methyl.

In a particular embodiment, the method of the invention utilises a compound of formula (Ic)

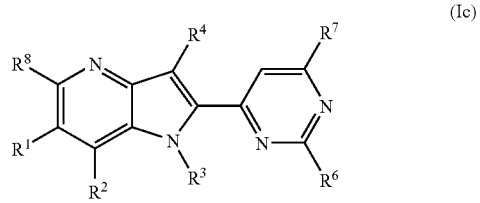

(Ic)

wherein R$^1$, R$^2$, R$^3$, R$^4$, R$^6$, R$^7$ and R$^8$ are as defined above and, preferably:

R$^1$, R$^2$, R$^7$ and R$^8$ are, independently, hydrogen, halogen or C$_{1-4}$ alkyl; R$^3$ is hydrogen or optionally substituted C$_{1-5}$ alkyl, C$_{2-6}$ alkenyl or C$_{2-6}$ alkynyl, the optional substituents being as defined above and, more preferably, halogen or alkoxy; R$^4$ is optionally substituted aryl, the optional substituents being as defined above and, more preferably, halogen; and R$^6$ is hydrogen, —SR$^{18}$ or —NR$^{18}$R$^{19}$ wherein R$^{18}$ is hydrogen or C$_{1-4}$ alkyl and R$^{19}$ is optionally substituted alkyl, —C(S)R$^{23}$ or —C(O)R$^{23}$ and R$^{23}$ is hydrogen or C$_{1-4}$ alkyl.

More preferably R$^1$, R$^2$, R$^7$ and R$^8$ are, independently, hydrogen, methyl, ethyl or chloro; R$^3$ is hydrogen, haloalkyl, alkoxyalkyl, alkenyl or alkynyl; R$^4$ is optionally substituted phenyl, the optional substituent being halogen; and R$^6$ is hydrogen or —NR$^{18}$R$^{19}$ wherein R$^{18}$ is hydrogen and R$^{19}$ is 2-methoxy-1-methylethyl, —C(S)R$^{23}$ or —C(O)R$^{23}$ and R$^{23}$ is C$_{1-4}$alkyl.

Even more preferably, R$^1$, R$^2$, R$^7$ and R$^8$ are, independently, hydrogen; R$^3$ is hydrogen, 2-fluoroethyl, methoxymethyl, prop-1,2-diene or prop-2-ynyl; R$^4$ is fluorophenyl (in particular, 4-fluorophenyl); and R$^6$ is —NR$^{18}$R$^{19}$ wherein R$^{18}$ is hydrogen and R$^{19}$ is —C(O)R$^{23}$ and R$^{23}$ methyl, ethyl, 1-methylethyl, 1-dimethylethyl or 3-methylpropyl.

More particularly, compounds for use in the present invention are shown in Table 1 (compounds of formula (Ia)), Table 2 (compounds of formula (Ib)) and Table 3 (compounds of formula (Ic)) below:

| Compound Number | R1 | R2 | R3 | R4 | R7 | R8 | Melting point ° | Mass (ES+__ |
|---|---|---|---|---|---|---|---|---|
| 1 | H | H | ethyl ester group | 4-F-phenyl | H | H | 127.0-128.0 | |
| 2 | H | H | Et | 4-F-phenyl | H | H | 208.0-209.0 | |
| 3 | H | H | acetyl group | 4-F-phenyl | H | H | 164.0-165.0 | |

-continued
| Compound Number | R1 | R2 | R3 | R4 | R7 | R8 | Melting point ° | Mass (ES+__ |
|---|---|---|---|---|---|---|---|---|
| 4 | H | H | 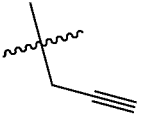 | 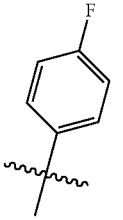 | H | H | 175.0-176.0 | |
| 5 | H | H | 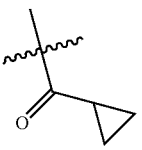 | 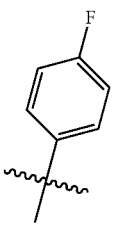 | H | H | 169.0-170.0 | |
| 6 | H | H | 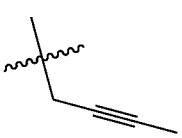 | 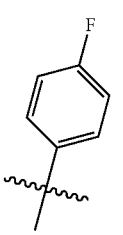 | H | H | 165.0-166.0 | |
| 7 | H | H | 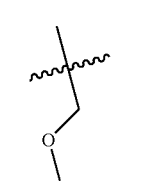 | 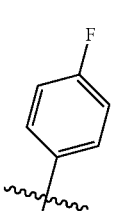 | H | H | 156.0-157.0 | |
| 8 | H | H | 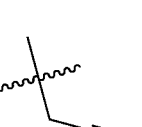 | 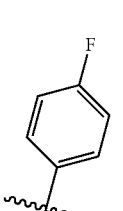 | H | H | 237.0-238.0 | |
| 9 | Cl | H | H | 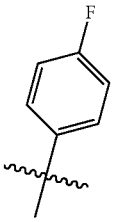 | H | H | 255.0-256.0 | |

-continued

| Compound Number | R1 | R2 | R3 | R4 | R7 | R8 | Melting point ° | Mass (ES+) |
|---|---|---|---|---|---|---|---|---|
| 10 | H | H | (2-methylallyl) | 4-F-phenyl | H | H | 157.0-158.0 | |
| 11 | H | H | (pent-4-enyl) | 4-F-phenyl | H | H | 169.0-170.0 | |
| 12 | H | H | (allyl, methyl branched) | 4-F-phenyl | H | H | 151.0-152.0 | |
| 13 | H | H | (allyl, methyl branched) | 4-F-phenyl | H | H | 151.0-152.0 | |
| 14 | H | H | (4-bromo-but-2-enyl, methyl branched) | 4-F-phenyl | H | H | — | 436/438 |
| 15 | H | H | (2-(2-methoxyethoxy)ethoxy, methyl branched) | 4-F-phenyl | H | H | 78.0-79.0 | |

-continued
| Compound Number | R1 | R2 | R3 | R4 | R7 | R8 | Melting point ° | Mass (ES+ |
|---|---|---|---|---|---|---|---|---|
| 16 | H | H | 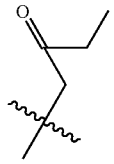 | 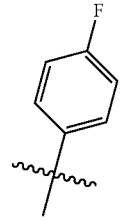 | H | H | 173.0-174.0 | |
| 17 | H | H | 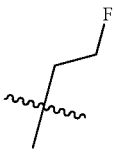 | 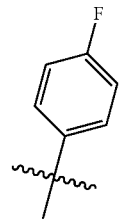 | H | H | 181.0-182.0 | |
| 18 | H | H | 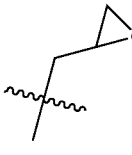 | 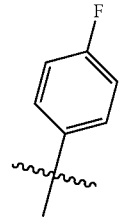 | H | H | 157.0-158.0 | |
| 19 | H | H | 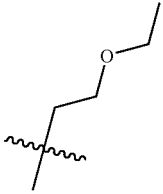 | 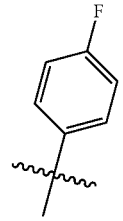 | H | H | 124.0-125.0 | |
| 20 | H | H | Me | 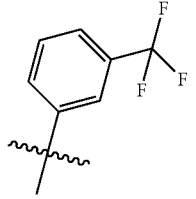 | H | H | 87.0-88.0 | |
| 21 | H | H | Me | 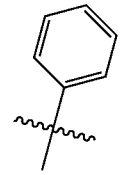 | H | H | 195.0-196.0 | |
| 22 | H | H | Me | 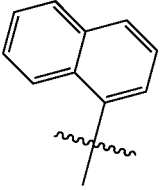 | H | H | 200.0-201.0 | |

-continued
| Compound Number | R1 | R2 | R3 | R4 | R7 | R8 | Melting point ° | Mass (ES+_ |
|---|---|---|---|---|---|---|---|---|
| 23 | H | H | Me | 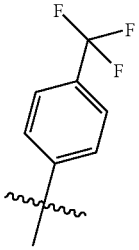 | H | H | 182.0-183.0 | |
| 25 | H | H | Me | 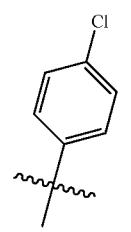 | H | H | 193.0-194.0 | |
| 26 | H | H | 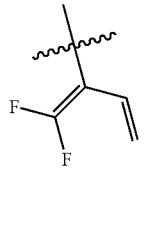 | 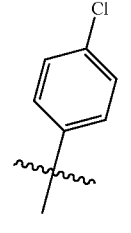 | H | H | — | 394 |
| 27 | H | H | H | 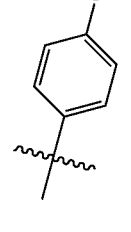 | H | H | — | 290 |
| 28 | H | H | Me | 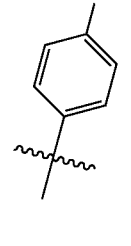 | H | H | — | 304 |
| 29 | H | H | Me |  | H | H | 188.0-189.0 | |

-continued
| Compound Number | R1 | R2 | R3 | R4 | R7 | R8 | Melting point ° | Mass (ES+ |
|---|---|---|---|---|---|---|---|---|
| 30 | H | H | 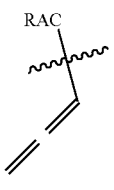 | 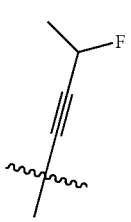 | H | H | 153.0-154.0 | |
| 31 | H | H | Me | 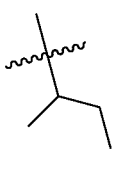 | H | H | — | 280 |
| 32 | H | H | 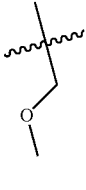 | 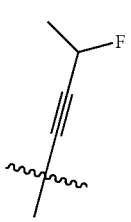 | H | H | 164.0-165.0 | |
| 33 | Cl | H |  | 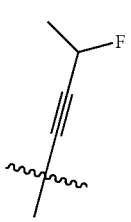 | H | H | 159.0-160.0 | |
| 34 | Cl | H | 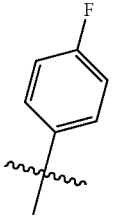 | 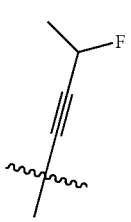 | H | H | 181.0-182.0 | |
| 35 | Me | H | H | 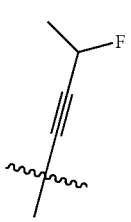 | H | H | 260.0-261.0 | |

-continued

| Compound Number | R1 | R2 | R3 | R4 | R7 | R8 | Melting point ° | Mass (ES+__ |
|---|---|---|---|---|---|---|---|---|
| 36 | Cl | H | (CH2-C≡CH) | 4-F-phenyl | H | H | 184.0-185.0 | |
| 37 | Cl | H | RAC (CH2-CH=CH2 branched / allyl-type) | 4-F-phenyl | H | H | 175.0-176.0 | |
| 38 | Me | H | (CH2-CH=CH2) | 4-F-phenyl | H | H | 132.0-133.0 | |
| 39 | Me | H | (CH2-C≡CH) | 4-F-phenyl | H | H | 152.0-153.0 | |
| 40 | Me | H | (CH2-O-CH3) | 4-F-phenyl | H | H | 140.0-141.0 | |
| 41 | Me | H | (sec-butyl-like: CH(CH3)CH2CH3) | 4-F-phenyl | H | H | 161.0-162.0 | |

-continued
| Compound Number | R1 | R2 | R3 | R4 | R7 | R8 | Melting point ° | Mass (ES+ |
|---|---|---|---|---|---|---|---|---|
| 42 | Cl | H | H | 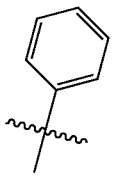 | H | H | 265.0-265.0 | |
| 43 | H | H | 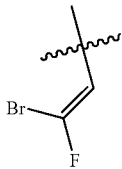 | 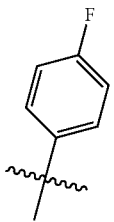 | H | H | — | 412/414 |
| 44 | Cl | H | 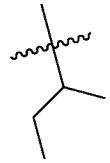 | 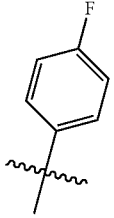 | H | H | 155.0-156.0 | |
| 45 | Cl | H | 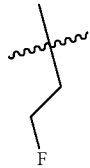 | 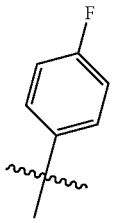 | H | H | 175.0-176.0 | |
| 46 | Cl | H | 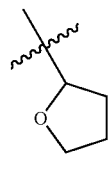 | 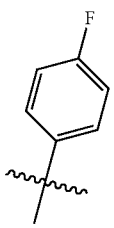 | H | H | 230.0-231.0 | |
| 47 | H | H | Me | 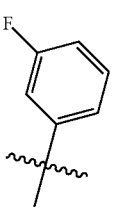 | H | H | 144.0-145.0 | |
| 48 | H | H | Me | 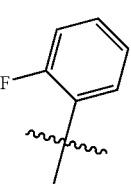 | H | H | 134.0-135.0 | |

-continued
| Compound Number | R1 | R2 | R3 | R4 | R7 | R8 | Melting point ° | Mass (ES+_ |
|---|---|---|---|---|---|---|---|---|
| 49 | Cl | H | 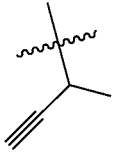 | 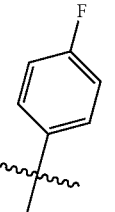 | H | H | 209.0-210.0 | |
| 50 | H | H | 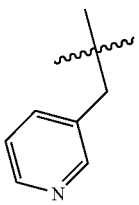 | 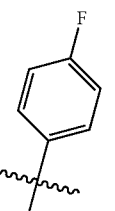 | H | H | 210.0-211.0 | |
| 51 | H | H | OH | 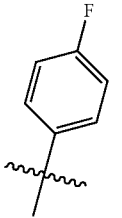 | H | H | 266.0-267.0 | |
| 52 | H | H | 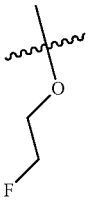 | 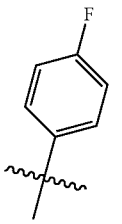 | H | H | 128.0-129.0 | |
| 53 | H | H | 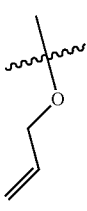 | 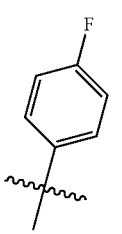 | H | H | — | 346 |
| 54 | H | H | 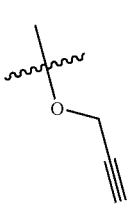 | 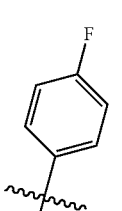 | H | H | 137.0-138.0 | |

-continued

| Compound Number | R1 | R2 | R3 | R4 | R7 | R8 | Melting point ° | Mass (ES+ |
|---|---|---|---|---|---|---|---|---|
| 55 | H | H | ![O-CH2-O-CH3] | 4-F-C6H4 | H | H | 150.0-151.0 | |
| 55 | H | H | ![O-CH2-O-CH3] | 4-F-C6H4 | H | H | 150.0-151.0 | |
| 57 | H | H | ![OCH3] | 4-F-C6H4 | H | H | 173.0-174.0 | |
| 58 | Me | H | ![CH2CH2F] | 4-F-C6H4 | H | H | 168.0-169.0 | |
| 59 | H | H | ![OEt] | 4-F-C6H4 | H | H | 140.0-141.0 | |
| 60 | H | H | ![vinyl] | 4-F-C6H4 | H | H | 174.0-175.0 | |

-continued
| Compound Number | R1 | R2 | R3 | R4 | R7 | R8 | Melting point ° | Mass (ES+ |
|---|---|---|---|---|---|---|---|---|
| 61 | H | H | 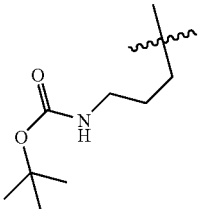 | 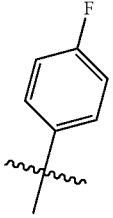 | H | H | 76.0-77.0 | |
| 63 | H | H | 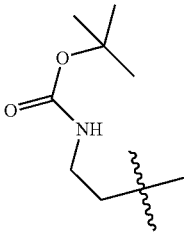 | 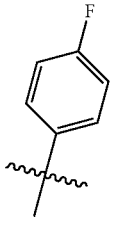 | H | H | | 433 |
| 64 | H | H | 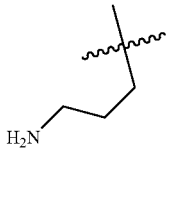 | 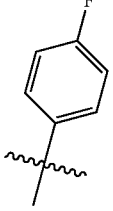 | H | H | 152.0-153.0 | |
| 66 | H | H | 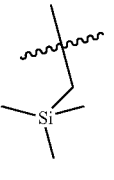 | 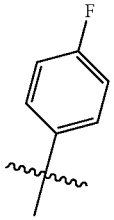 | H | H | 149.0-150.0 | |
| 67 | H | H | Me | 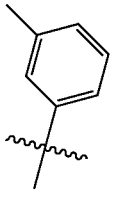 | H | H | 136.0-137.0 | |
| 68 | H | H | 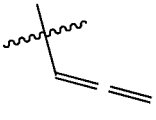 | H | H | H | 110.0-111.0 | |
| 69 | H | H | 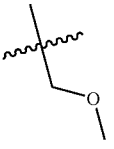 | H | H | H | 106.0-107.0 | |

-continued

| Compound Number | R1 | R2 | R3 | R4 | R7 | R8 | Melting point ° | Mass (ES+) |
|---|---|---|---|---|---|---|---|---|
| 70 | H | H | (allyl-methyl group) | H | H | H | 108.0-109.0 | |
| 71 | H | H | (2-fluoroethyl-methyl group) | H | H | H | 119.0-120.0 | |
| 72 | H | H | (CH(CH$_3$)COOH) | 4-F-phenyl | H | H | 250.0-250.0 | |
| 73 | H | H | (1-hydroxycyclopropyl-methyl) | 4-F-phenyl | H | H | | 374 |
| 74 | H | H | (CH(CH$_3$)CH$_2$OH with methyl) | 4-F-phenyl | H | H | | 348 |
| 75 | H | H | (methyl (E)-4-methylpent-2-enoate group) | 4-F-phenyl | H | H | | 402 |
| 76 | H | H | (CH(CH$_3$)CH(SMe)COOMe) | 4-F-phenyl | H | H | 161.0-162.0 | |

-continued

| Compound Number | R1 | R2 | R3 | R4 | R7 | R8 | Melting point ° | Mass (ES+ |
|---|---|---|---|---|---|---|---|---|
| 77 | H | H | -CH(CH₃)CH₂CH₂OCH₃ | 4-F-C₆H₄- | H | H | 133.0-134.0 | |
| 78 | H | H | -CH(CH₃)CH(CH₃)CH₂F | 4-F-C₆H₄- | H | H | 166.0-167.0 | |
| 79 | H | H | -CH(CH₃)SO₂N(CH₃)₂ | 4-F-C₆H₄- | H | H | 205.0-206.0 | |
| 80 | H | H | -CH(CH₃)SO₂-(4-F-C₆H₄) | 4-F-C₆H₄- | H | H | 189.0-190.0 | |
| 81 | H | H | -CH(CH₃)SO₂CH(CH₃)₂ | 4-F-C₆H₄- | H | H | 212.0-212.0 | |
| 82 | H | H | H | 4-F-C₆H₄- | H | Cl | 250.0-250.0 | |

-continued

| Compound Number | R1 | R2 | R3 | R4 | R7 | R8 | Melting point ° | Mass (ES+ |
|---|---|---|---|---|---|---|---|---|
| 83 | H | H | (allyl) | 4-F-phenyl | H | Cl | 180.0-181.0 | |
| 84 | H | H | (3-fluoropropyl) | 4-F-phenyl | H | Cl | 197.0-198.0 | |
| 85 | H | H | (1-methylallyl) | 4-F-phenyl | H | Cl | 245.0-246.0 | |
| 86 | H | H | RAC (allenyl-methyl) | 4-F-phenyl | H | Cl | 220.0-221.0 | |
| 87 | H | H | (allyl) | 4-F-phenyl | H | (1-methoxypropan-2-yl)amino | 159.0-160.0 | |
| 88 | H | H | (allyl) | 4-F-phenyl | H | (1-phenylethyl)amino | 197.0-198.0 | |

-continued

| Compound Number | R1 | R2 | R3 | R4 | R7 | R8 | Melting point ° | Mass (ES+ |
|---|---|---|---|---|---|---|---|---|
| 89 | H | H | CH(CH3)CH2C(O)OCH3 | 4-F-phenyl | H | H | 166.0-167.0 | |
| 90 | H | H | OH | 4-F-phenyl | H | Me | 222.0-223.0 | |
| 91 | H | H | OCH2CH2F | 4-F-phenyl | H | Me | 165.0-166.0 | |
| 92 | H | H | OCH2C≡CH | 4-F-phenyl | H | Me | 151.0-152.0 | |
| 93 | H | H | CH2CH2C≡CH | 4-F-phenyl | H | Me | | 342 |
| 94 | H | H | OCH2OCH3 | 4-F-phenyl | H | Me | 143.0-144.0 | |

-continued

| Compound Number | R1 | R2 | R3 | R4 | R7 | R8 | Melting point ° | Mass (ES+) |
|---|---|---|---|---|---|---|---|---|
| 95 | H | H | -O-CH₂-C(=CH₂)-CH₃ | 4-F-C₆H₄- | H | Me | — | 374 |
| 96 | Cl | H | -CH(CH₃)-CH=CH₂ | 4-F-C₆H₄- | H | H | 140.0-142.0 | |
| 97 | H | H | -O-CH₂-CH=CH-CH₃ | 4-F-C₆H₄- | H | H | 126.0-127.0 | |
| 98 | H | H | -O-CH₂-CN | 4-F-C₆H₄- | H | H | 154.0-155.0 | |
| 99 | H | H | -O-CH₂-cyclopropyl | 4-F-C₆H₄- | H | H | 111.0-112.0 | |
| 100 | H | H | -O-CH₂-CH₂-CH₃ | 4-F-C₆H₄- | H | H | 107.0-108.0 | |

-continued

| Compound Number | R1 | R2 | R3 | R4 | R7 | R8 | Melting point ° | Mass (ES+ |
|---|---|---|---|---|---|---|---|---|
| 101 | H | H | -O-C(CH₃)(CN)- | 4-F-phenyl | H | H | 155.0-156.0 | |
| 102 | H | H | -O-CH₂-C≡C-CH₃ | 4-F-phenyl | H | H | 178.0-180.0 | |
| 103 | H | H | -O-CH₂-C(CH₃)=CH₂ | 4-F-phenyl | H | H | 98.0-99.0 | |
| 104 | H | H | -O-CH₂-C≡C-CH₂CH₃ | 4-F-phenyl | H | H | 163.0-164.0 | |
| 105 | H | H | -O-CH₂-CH=C(CH₃)₂ | 4-F-phenyl | H | H | 126.0-127.0 | |
| 106 | H | H | -O-CH₂-C(=O)-CH₃ | 4-F-phenyl | H | H | — | 362 |

-continued
| Compound Number | R1 | R2 | R3 | R4 | R7 | R8 | Melting point ° | Mass (ES+ |
|---|---|---|---|---|---|---|---|---|
| 107 | H | H | 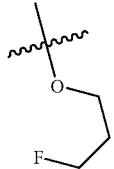 | 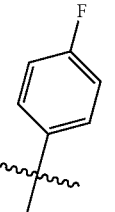 | H | H | 93.0-94.0 | |
| 108 | H | H | 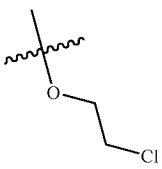 | 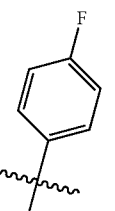 | H | H | 150.0-151.0 | |
| 109 | H | H | 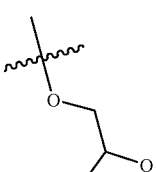 | 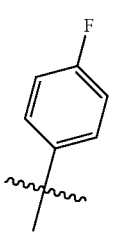 | H | H | 123.0-124.0 | |
| 110 | H | H | 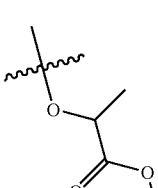 | 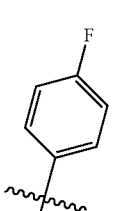 | H | H | 119.0-120.0 | |
| 111 | H | H | 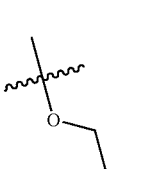 | 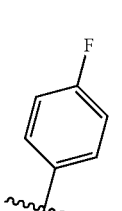 | H | H | 192.0-193.0 | |
| 112 | H | H | 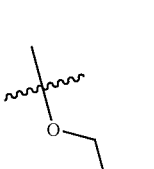 | 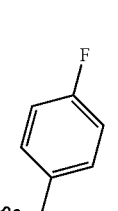 | H | H | 98.0-99.0 | |

-continued

| Compound Number | R1 | R2 | R3 | R4 | R7 | R8 | Melting point ° | Mass (ES+_ |
|---|---|---|---|---|---|---|---|---|
| 113 | H | H | *methyl 2-oxybutanoate* | *4-F-phenyl* | H | H | 126.0-127.0 | |
| 114 | H | H | *methyl 2-oxyacrylate* | *4-F-phenyl* | H | H | 148.0-149.0 | |
| 115 | H | H | *methyl 2-oxy-3-methylbutanoate* | *4-F-phenyl* | H | H | 144.0-145.0 | |
| 116 | H | H | *2-oxy-3-methylbutanoic acid* | *4-F-phenyl* | H | H | 188.0-189.0 | |
| 117 | H | H | *2-oxypropanoic acid* | *4-F-phenyl* | H | H | 197.0-198.0 | |
| 118 | H | H | *2-ethylbutanoate ester* | *4-F-phenyl* | H | H | 124.0-125.0 | |

-continued

| Compound Number | R1 | R2 | R3 | R4 | R7 | R8 | Melting point ° | Mass (ES+ |
|---|---|---|---|---|---|---|---|---|
| 119 | H | H | isovaleryloxy (CH(CH₃)₂CH₂C(=O)O-) | 4-F-C₆H₄- | H | H | 130.0-131.0 | |
| 120 | H | H | (3-chloro-2,2-dimethylpropanoyloxy) ClCH₂C(CH₃)₂C(=O)O- | 4-F-C₆H₄- | H | H | 146.0-147.0 | |
| 121 | H | H | (1-fluoropropan-2-yl)oxy | 4-F-C₆H₄- | H | H | 121.0-121.0 | |
| 122 | H | H | (1-methoxypropan-2-yl)oxy | 4-F-C₆H₄- | H | H | 121.0-122.0 | |
| 123 | H | H | allyloxy | 4-F-C₆H₄- | H | Me | 120.0-121.0 | |
| 124 | H | Me | OH | 4-F-C₆H₄- | H | H | 197.0-204.0 | |

-continued

| Compound Number | R1 | R2 | R3 | R4 | R7 | R8 | Melting point ° | Mass (ES+ |
|---|---|---|---|---|---|---|---|---|
| 125 | H | Me | -OCH₂CH₂F | 4-F-C₆H₄ | H | H | 167.0-168.0 | |
| 126 | H | Me | -OCH₂C≡CH | 4-F-C₆H₄ | H | H | 169.0-170.0 | |
| 127 | H | Me | -CH₂C≡CH | 4-F-C₆H₄ | H | H | 147.0-148.0 | |
| 128 | H | H | -CH₂C≡CCH₂CH₃ | 4-F-C₆H₄ | H | H | 147.0-148.0 | |
| 129 | H | H | -OCH₂C≡CCH₂OH | 4-F-C₆H₄ | H | H | 172.0-173.0 | |
| 130 | H | H | -CH₂C≡CCH₂OH | 4-F-C₆H₄ | H | H | 124.0-126.0 | |

-continued
| Compound Number | R1 | R2 | R3 | R4 | R7 | R8 | Melting point ° | Mass (ES+__ |
|---|---|---|---|---|---|---|---|---|
| 131 | H | H | H | 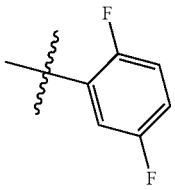 | H | H | 130.0-130.0 | |
| 132 | H | H | H | 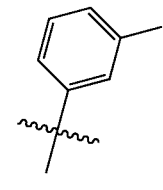 | H | H | 250.0-260.0 | |
| 133 | H | H | 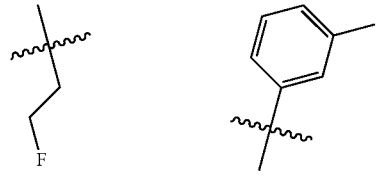 | 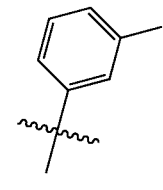 | H | H | — | 332 |
| 134 | H | H | 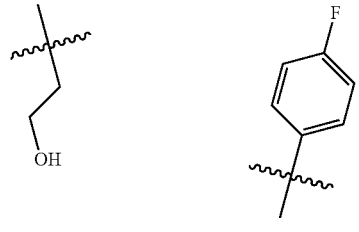 | 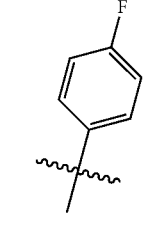 | H | H | 220.0-222.0 | |
| 135 | H | H | 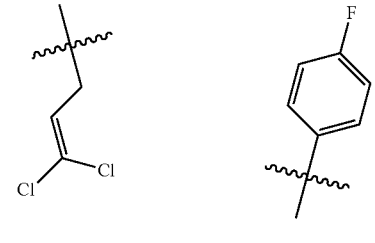 | 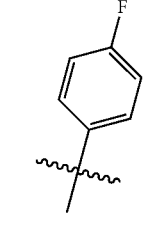 | H | H | 239.0-240.0 | |
| 136 | H | H | 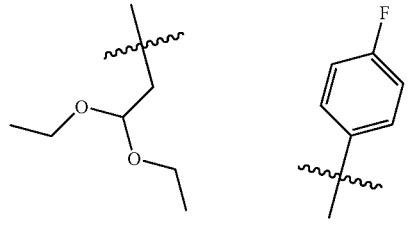 | 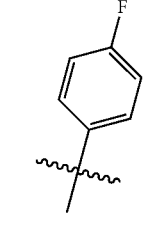 | H | H | 136.0-137.0 | |
| 137 | H | H |  | 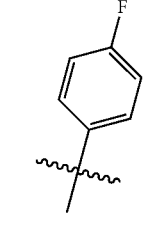 | H | H | 129.0-130.0 | |

-continued

| Compound Number | R1 | R2 | R3 | R4 | R7 | R8 | Melting point ° | Mass (ES+_ |
|---|---|---|---|---|---|---|---|---|
| 138 | H | H | (CH₂CH₂I with gem-dimethyl) | 4-F-C₆H₄ | H | H | 164.0-169.0 | |
| 139 | H | H | CH₂CH(OH)(CN) | 4-F-C₆H₄ | H | H | 215.0-217.0 | |
| 140 | H | H | CH₂CH(F)(OMe) | 4-F-C₆H₄ | H | H | 184.0-185.0 | |
| 141 | H | H | CH(CH₃)C(O)CH₃ | 4-F-C₆H₄ | H | H | 215.0-216.0 | |
| 142 | H | H | CH(CH₃)CF₂CH₃ | 4-F-C₆H₄ | H | H | — | 382 |
| 143 | H | H | CH(CH₃)CH=CH₂ | 4-F-C₆H₄ | H | H | — | 344 |

-continued

| Compound Number | R1 | R2 | R3 | R4 | R7 | R8 | Melting point ° | Mass (ES+ |
|---|---|---|---|---|---|---|---|---|
| 144 | H | H | (1-hydroxy-2-methylpropyl, sec-butyl with OH) | 4-fluorophenyl | H | H | 208.0-209.0 | |
| 145 | H | H | (2-methyl-2-(methoxycarbonyl)propan-2-yloxy) | 4-fluorophenyl | H | H | 177.0-178.0 | |
| 145 | H | H | (2-methyl-2-(methoxycarbonyl)propan-2-yloxy) | 4-fluorophenyl | H | H | 177.0-178.0 | |
| 146 | H | H | (1-fluoro-2-methylpropyl) | 4-fluorophenyl | H | H | | 364 |
| 147 | H | H | (enol ether group) | 4-fluorophenyl | H | H | 149.0-150.0 | |
| 148 | H | H | (2-methyl-2-((N,N-diethylsulfamoyl)oxymethyl)propan-2-yloxy) | 4-fluorophenyl | H | H | | 497 |

-continued
| Compound Number | R1 | R2 | R3 | R4 | R7 | R8 | Melting point ° | Mass (ES+_ |
|---|---|---|---|---|---|---|---|---|
| 149 | H | H | 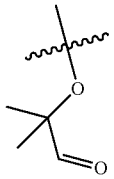 | 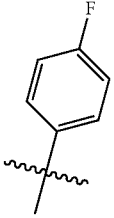 | H | H | | 376 |
| 150 | Me | H | 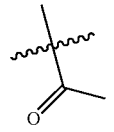 | 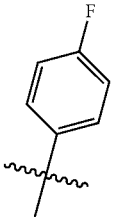 | H | H | 148.0-149.0 | |
| 151 | H | Me | H | 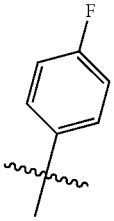 | H | H | 250.0-250.0 | |
| 152 | H | Me | 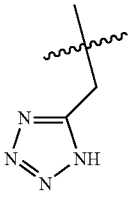 | 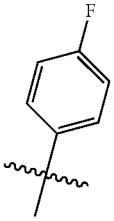 | H | H | 225.0-230.0 | |
| 153 | Br | Me | H | Br | H | H | 250.0-999.0 | |
| 154 | H | Me | 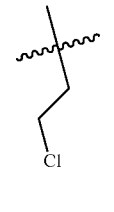 | 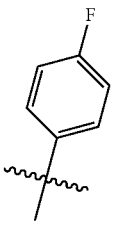 | H | H | 250.0-999.0 | |
| 155 | H | Me | 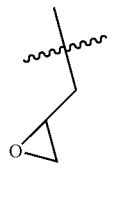 | 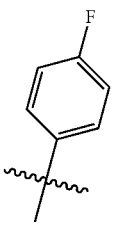 | H | H | 132.0-133.0 | |

-continued

| Compound Number | R1 | R2 | R3 | R4 | R7 | R8 | Melting point ° | Mass (ES+__ |
|---|---|---|---|---|---|---|---|---|
| 155 | H | Me | ![epoxide CH2-CH(O)CH2] | 4-F-phenyl | H | H | 132.0-133.0 | |
| 156 | Br | H | -O-iPr | 4-F-phenyl | H | H | 157.0-158.0 | |
| 157 | TMS-C≡C- | H | -O-iPr | 4-F-phenyl | H | H | 181.0-182.0 | |
| 158 | 2,5-dimethoxyphenyl-CH(Me)- | H | -O-iPr | 4-F-phenyl | H | H | 147.0-148.0 | |
| 159 | Br | H | H | 4-F-phenyl | H | H | 263.0-264.0 | |
| 160 | —CN | H | -O-iPr | 4-F-phenyl | H | H | 199.0-200.0 | |

-continued
| Compound Number | R1 | R2 | R3 | R4 | R7 | R8 | Melting point ° | Mass (ES+ |
|---|---|---|---|---|---|---|---|---|
| 161 | —CN | H | H | 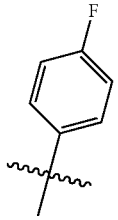 | H | H | 265.0-266.0 | |
| 162 | H | H | 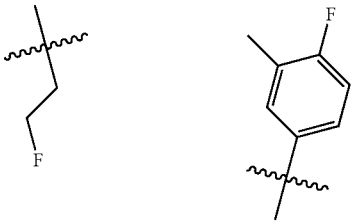 | 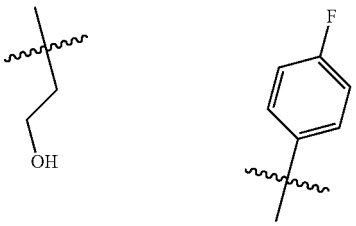 | H | H | | 350 |
| 163 | H | Me | 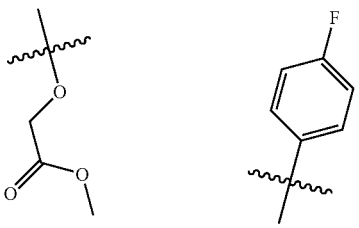 | 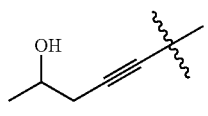 | H | H | 212.0-213.0 | |
| 164 | H | Me | 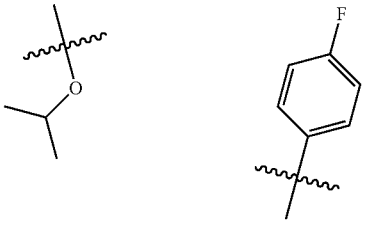 | 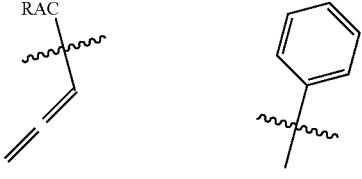 | H | H | 133.0-134.0 | |
| 165 | 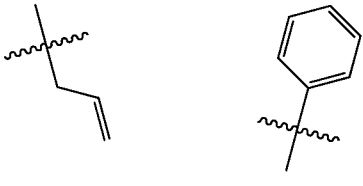 | H |  |  | H | H | — | 430 |
| 167 | H | H |  |  | H | H | 135.0-136.0 | |
| 168 | H | H |  |  | H | H | 151.0-152.0 | |

-continued

| Compound Number | R1 | R2 | R3 | R4 | R7 | R8 | Melting point ° | Mass (ES+ |
|---|---|---|---|---|---|---|---|---|
| 169 | H | H | CH₂OCH₃ | phenyl | H | H | 145.0-147.0 | |
| 170 | H | H | CH₂CH₂F | phenyl | H | H | 205.0-206.0 | |
| 171 | H | H | CH₂CN | phenyl | H | H | 174.0-175.0 | |
| 172 | H | H | CH₂-epoxide | phenyl | H | H | 180.0-181.0 | |
| 173 | acetyl | H | CH₂C≡CH | 4-F-phenyl | H | H | 185.0-186.0 | |
| 174 | acetyl | H | CH₂CH=CH₂ | 4-F-phenyl | H | H | 190.0-191.0 | |
| 175 | CH(OH)CH₃ | H | H | 4-F-phenyl | H | H | 217.0-219.0 | |

-continued

| Compound Number | R1 | R2 | R3 | R4 | R7 | R8 | Melting point ° | Mass (ES+_ |
|---|---|---|---|---|---|---|---|---|
| 176 | isopropyl ester-alkyl | H | isopropyl ester-alkyl | 4-fluorophenyl | H | H |  | 444 |
| 293 | H | H | but-3-ynyl | cyclohexyl | H | H | 123.0-124.0 |  |
| 294 | H | H | H | 4-methoxyphenyl | H | H | 258.0-259.0 |  |
| 295 | H | H | allyl | 4-methoxyphenyl | H | H |  | 342 |
| 296 | H | H | H | 3-methoxyphenyl | H | H | 236.0-237.0 |  |
| 297 | H | H | H | 2-methoxyphenyl | H | H | 296.0-299.0 |  |
| 298 | H | H | H | 3-(methoxycarbonyl)phenyl | H | H | 215.0-220.0 |  |

-continued

| Compound Number | R1 | R2 | R3 | R4 | R7 | R8 | Melting point ° | Mass (ES+) |
|---|---|---|---|---|---|---|---|---|
| 299 | H | H | CH₂-C≡CH | 3-methoxyphenyl | H | H | — | 340 |
| 300 | H | H | CH₂-C≡CH | 4-methoxyphenyl | H | H | 174.0-175.0 | |
| 301 | H | H | CH₂-C≡CH | 2-methoxyphenyl | H | H | — | 340 |
| 302 | H | H | CH₂-C≡CH | 3-(methoxycarbonyl)phenyl | H | H | 134.0-135.0 | |
| 303 | H | H | n-propyl | phenyl | H | H | 171.0-172.0 | |
| 304 | H | H | benzyl | n-butyl | H | H | — | 342 |
| 305 | H | H | H | n-butyl | H | H | 169.0-172.0 | |
| 306 | H | H | sec-butoxy | 4-fluorophenyl | H | H | 124.0-125.0 | |

-continued
| Compound Number | R1 | R2 | R3 | R4 | R7 | R8 | Melting point ° | Mass (ES+ |
|---|---|---|---|---|---|---|---|---|
| 307 | H | H | 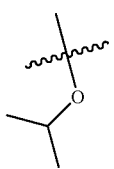 | 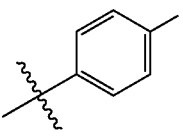 | H | H | 139.0-140.0 | |
| 308 | H | H |  | 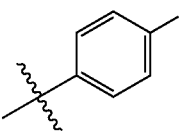 | H | H | 166.0-168.0 | |
| 309 | H | H | 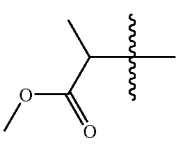 | 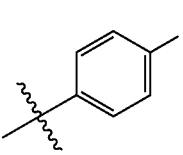 | H | H | 166.0-167.0 | |
| 310 | H | H |  | 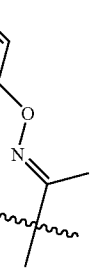 | H | H | — | 333 |
| 311 | H | H |  | 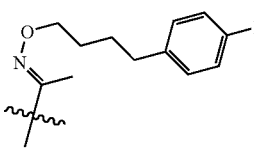 | H | H | 105.0-110.0 | |
| 312 | H | H |  | 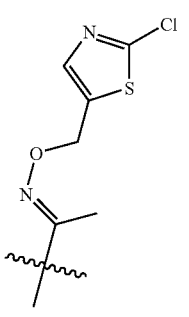 | H | H | 141.0-144.0 | |
| 313 | H | H |  | 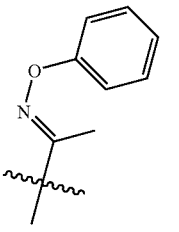 | H | H | 148.0-151.0 | |

-continued

| Compound Number | R1 | R2 | R3 | R4 | R7 | R8 | Melting point ° | Mass (ES+) |
|---|---|---|---|---|---|---|---|---|
| 314 | H | H | *CH2-C(CH3)(-)-CH2-CH=CH2* | C(=NOH)(CH3)- | H | H | — | 293 |
| 315 | H | H | *CH2-C(CH3)(-)-CH2-CH=CH2* | Br | H | H | 148-150 | |
| 316 | H | H | *CH2-C(CH3)(-)-CH2-CH=CH2* | C(=O)CH3 | H | H | — | 278 |
| 317 | H | H | *CH2-C(CH3)(-)-CH2-CH=CH2* | C(=N-O-CH2-CH=CHCl)(CH3)- | H | H | — | 367 |
| 318 | H | H | *CH2-C(CH3)(-)-CH2-CH=CH2* | C(=N-O-CH3)(CH3)- | H | H | — | 307 |
| 319 | H | H | *CH2-C(CH3)(-)-CH2-CH=CH2* | C(=N-O-CH3)(CH3)- | H | H | — | 307 |
| 320 | H | H | *CH2-C(CH3)(-)-CH2-CH=CH2* | C(=N-O-CH2CH3)(CH3)- | H | H | — | 379 |

-continued

| Compound Number | R1 | R2 | R3 | R4 | R7 | R8 | Melting point ° | Mass (ES+ |
|---|---|---|---|---|---|---|---|---|
| 321 | H | H | (but-3-en-1-yl branch) | CH₃-CH₂-O-N=C(CH₃)- | H | H | — | 379 |
| 322 | H | H | (but-3-en-1-yl branch) | PhCH₂-O-N=C(CH₃)- | H | H | — | 384 |
| 323 | H | H | (but-3-en-1-yl branch) | PhCH₂-O-N=C(CH₃)- | H | H | — | 384 |
| 324 | H | H | (but-3-en-1-yl branch) | Cl-CH=CH-CH₂-O-N=C(CH₃)- | H | H | — | 367 |
| 325 | H | H | (but-3-en-1-yl branch) | 4-(SMe)-C₆H₄-C(CH₃)- | H | H | — | 358 |
| 326 | H | H | (but-3-en-1-yl branch) | Me | H | H | — | 250 |
| 327 | H | H | (but-3-en-1-yl branch) | furan-3-yl-C(CH₃)- | H | H | — | 302 |

-continued

| Compound Number | R1 | R2 | R3 | R4 | R7 | R8 | Melting point ° | Mass (ES+) |
|---|---|---|---|---|---|---|---|---|
| 328 | H | H | but-3-enyl | 4-(ethoxycarbonyl)phenyl | H | H | — | 384 |
| 329 | H | H | but-3-enyl | thiophen-3-yl | H | H | — | 318 |
| 330 | H | H | but-3-enyl | hex-1-enyl | H | H | — | 318 |
| 331 | H | H | but-3-enyl | pyrimidin-5-yl | H | H | — | 314 |
| 332 | H | H | but-3-enyl | 5-formylfuran-2-yl | H | H | — | 330 |
| 333 | H | H | but-3-enyl | 2-formylthiophen-3-yl | H | H | — | 346 |
| 334 | H | H | but-3-enyl | pent-1-enyl | H | H | — | 304 |
| 335 | H | H | but-3-enyl | 2-chlorophenyl | H | H | — | 346 |

-continued

| Compound Number | R1 | R2 | R3 | R4 | R7 | R8 | Melting point ° | Mass (ES+) |
|---|---|---|---|---|---|---|---|---|
| 336 | H | H | (but-3-enyl) | 3-nitrophenyl | H | H | — | 357 |
| 337 | H | H | (but-3-enyl) | 2-methylphenyl | H | H | — | 362 |
| 338 | H | H | (but-3-enyl) | 4-formylphenyl | H | H | — | 340 |
| 339 | H | H | (but-3-enyl) | 3-formylphenyl | H | H | — | 340 |
| 340 | H | H | (but-3-enyl) | 3-acetylphenyl | H | H | — | 354 |
| 341 | H | H | (but-3-enyl) | 2,4-dichlorophenyl | H | H | — | 380 |
| 342 | H | H | (but-3-enyl) | 2-fluorophenyl | H | H | — | 330 |
| 343 | H | H | (but-3-enyl) | 2,4-difluorophenyl | H | H | — | 348 |

-continued

| Compound Number | R1 | R2 | R3 | R4 | R7 | R8 | Melting point ° | Mass (ES+_ |
|---|---|---|---|---|---|---|---|---|
| 344 | H | H | but-3-enyl | 2-acetylphenyl | H | H | — | 354 |
| 345 | H | H | but-3-enyl | 4-cyanophenyl | H | H | — | 337 |
| 346 | H | H | but-3-enyl | 2-ethylphenyl | H | H | — | 340 |
| 347 | H | H | but-3-enyl | pyridin-4-yl | H | H | — | 313 |
| 348 | H | H | but-3-enyl | 3-(hydroxymethyl)phenyl | H | H | — | 342 |
| 349 | H | H | but-3-enyl | cyclopropyl | H | H | — | 276 |
| 350 | H | H | but-3-enyl | 3-hydroxyphenyl | H | H | — | 328 |
| 351 | H | H | but-3-enyl | 3-cyanophenyl | H | H | — | 337 |

-continued
| Compound Number | R1 | R2 | R3 | R4 | R7 | R8 | Melting point ° | Mass (ES+_ |
|---|---|---|---|---|---|---|---|---|
| 352 | H | H | 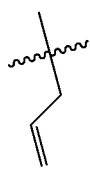 | 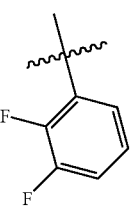 | H | H | — | 348 |
| 353 | H | H |  | 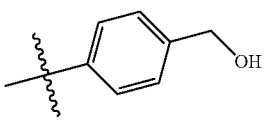 | H | H | — | 342 |
| 354 | H | H | 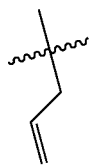 | 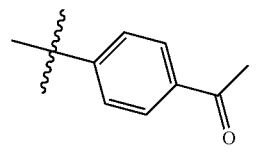 | H | H | — | 354 |
| 355 | H | H | 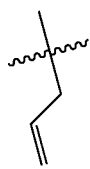 | 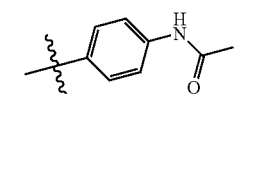 | H | H | — | 369 |
| 356 | H | H | 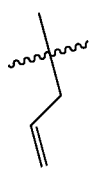 | 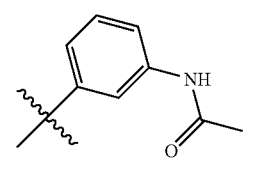 | H | H | — | 369 |
| 357 | H | H | 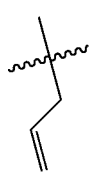 | 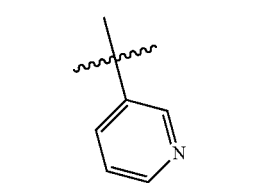 | H | H | — | 313 |
| 358 | H | H | 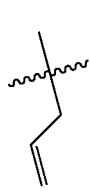 | 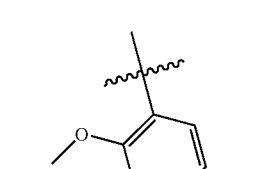 | H | H | — | 343 |
| 359 | H | H | 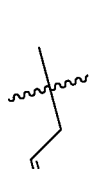 | 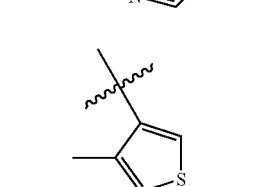 | H | H | — | 332 |

-continued

| Compound Number | R1 | R2 | R3 | R4 | R7 | R8 | Melting point ° | Mass (ES+_ |
|---|---|---|---|---|---|---|---|---|
| 360 | H | H | (but-3-enyl) | 3,5-difluorophenyl | H | H | — | 396 |
| 361 | H | H | (but-3-enyl) | 4-(trifluoromethoxy)phenyl | H | H | — | 396 |
| 362 | H | H | (but-3-enyl) | 3,4,5-trifluorophenyl | H | H | — | 366 |
| 363 | H | H | (but-3-enyl) | 6-fluoropyridin-3-yl | H | H | — | 331 |
| 364 | H | H | (but-3-enyl) | 2,4,5-trifluorophenyl | H | H | — | 366 |
| 365 | H | H | (but-3-enyl) | 4-fluoro-3-formylphenyl | H | H | — | 358 |
| 366 | H | H | (but-3-enyl) | 3-(cyanomethyl)phenyl | H | H | — | 351 |
| 367 | H | H | (but-3-enyl) | 3-(N-methylcarbamoyl)phenyl | H | H | — | 369 |

-continued

| Compound Number | R1 | R2 | R3 | R4 | R7 | R8 | Melting point ° | Mass (ES+) |
|---|---|---|---|---|---|---|---|---|
| 368 | H | H | but-3-enyl | 4-(N-methylcarbamoyl)phenyl | H | H | — | 369 |
| 369 | H | H | but-3-enyl | 3,4-difluorophenyl | H | H | — | 348 |
| 370 | H | H | but-3-enyl | 2-fluoro-6-methoxyphenyl | H | H | — | 360 |
| 371 | H | H | but-3-enyl | 5-bromopyridin-3-yl | H | H | — | 391 |
| 372 | H | H | but-3-enyl | 5-acetylthiophen-2-yl | H | H | — | 360 |
| 373 | H | H | but-3-enyl | 2,5-difluorophenyl | H | H | — | 348 |
| 374 | H | H | but-3-ynyl | butyl | H | H | — | 290 |
| 375 | H | H | but-3-enyl | butyl | H | H | — | 292 |

-continued

| Compound Number | R1 | R2 | R3 | R4 | R7 | R8 | Melting point ° | Mass (ES+) |
|---|---|---|---|---|---|---|---|---|
| 376 | H | H | (CH2CH2F group) | (pentyl group) | H | H | 260.0-999.0 | |
| 377 | H | H | (CH2OCH3 group) | (pentyl group) | H | H | 289.0-291.0 | |
| 378 | Me | H | H | (phenyl group) | H | H | | 286 |
| 379 | H | H | H | (SPh group) | H | H | 289-291 | |
| 380 | H | H | (allyl group) | (SPh group) | H | H | >260 | |
| 381 | H | H | (allyl group) | (SO2Ph group) | H | H | | 376 |
| 382 | H | H | (benzyl group) | (isopropyl group) | H | H | | 328 |

TABLE 1a

HPLC Retention Times of Certain Compounds of Table 1

| Compound Number | Retention Time (Min) | Method |
|---|---|---|
| 325 | 0.93 | B |
| 326 | 0.18 | B |
| 327 | 0.39 | B |
| 328 | 1.08 | B |
| 329 | 0.46 | B |
| 330 | 1.21 | B |
| 331 | 0.28 | B |
| 332 | 0.55 | B |

TABLE 1a-continued

HPLC Retention Times of Certain Compounds of Table 1

| Compound Number | Retention Time (Min) | Method |
|---|---|---|
| 333 | 0.48 | B |
| 334 | 1.01 | B |
| 335 | 0.69 | B |
| 336 | 0.94 | B |
| 337 | 0.58 | B |
| 338 | 0.58 | B |
| 339 | 0.51 | B |
| 340 | 0.6 | B |
| 341 | 1.04 | B |
| 342 | 0.52 | B |
| 343 | 0.73 | B |
| 344 | 0.44 | B |
| 345 | 0.8 | B |
| 346 | 0.84 | B |
| 347 | 0.31 | B |
| 348 | 0.29 | B |
| 349 | 0.26 | B |
| 350 | 0.23 | A |
| 351 | 0.46 | A |
| 352 | 0.34 | A |
| 353 | 0.16 | A |
| 354 | 0.29 | A |
| 355 | 0.17 | A |
| 356 | 0.17 | A |
| 357 | 0.18 | A |
| 358 | 0.17 | A |
| 359 | 0.26 | A |
| 360 | 0.76 | A |
| 361 | 0.98 | A |
| 362 | 0.94 | A |
| 363 | 0.22 | A |
| 364 | 0.57 | A |
| 365 | 0.3 | A |
| 366 | 0.22 | A |
| 367 | 0.17 | A |
| 368 | 0.19 | A |
| 369 | 0.65 | A |
| 370 | 0.25 | A |
| 371 | 0.57 | A |
| 372 | 0.8 | A |
| 373 | 0.34 | A |

Method: see under "Examples" for details of Method A and Method B

TABLE 2

| Compound Number | R1 | R2 | R3 | R4 | R6 | R7 | R8 | Melting Point ° | Mass (ES+_ |
|---|---|---|---|---|---|---|---|---|---|
| 177 | H | H | H | 4-F-phenyl | Cl | H | H | 260-260 | |
| 178 | H | H | propargyl | 4-F-phenyl | Cl | H | H | 175-176 | |
| 179 | H | H | acetonyl (CH2C(O)CH3) | 4-F-phenyl | Cl | H | H | 190-191 | |
| 180 | H | H | 2-methoxyethyl | 4-F-phenyl | Cl | H | H | 166-167 | |

TABLE 2-continued

| Compound Number | R1 | R2 | R3 | R4 | R6 | R7 | R8 | Melting Point ° | Mass (ES+ |
|---|---|---|---|---|---|---|---|---|---|
| 181 | H | H | (allyl) | 4-F-phenyl | Cl | H | H | 164-165 | |
| 182 | H | H | (methoxymethyl) | 4-F-phenyl | (NH-CH(CH3)-CH2-OMe) | H | H | | 421 |
| 183 | H | H | (2-fluoroethyl) | 4-F-phenyl | Cl | H | H | 160-161 | |
| 184 | H | H | (3-fluoropropyl) | 4-F-phenyl | (NH-CH(CH3)-CH2-OMe) | H | H | | 423 |
| 185 | H | H | (allyl) | 4-F-phenyl | (NH-CH2-tetrahydrofuran-2-yl) | H | H | | 415 |
| 186 | H | H | (3-fluoropropyl) | 4-F-phenyl | (NH-3-F-phenyl) | H | H | 226-227 | |

TABLE 2-continued

| Compound Number | R1 | R2 | R3 | R4 | R6 | R7 | R8 | Melting Point ° | Mass (ES+) |
|---|---|---|---|---|---|---|---|---|---|
| 187 | H | H | allyl | 4-F-C6H4 | -NH-CH(CH3)-CH2-OCH3 | H | H | | 399 |
| 188 | Cl | H | H | 4-F-C6H4 | Cl | H | H | 210-211 | |
| 189 | Cl | H | RAC (allenyl) | 4-F-C6H4 | Cl | H | H | 184-185 | |
| 190 | Cl | H | allyl | 4-F-C6H4 | -NH-(3-F-C6H4) | H | H | 168-169 | |
| 191 | Cl | H | propargyl | 4-F-C6H4 | Cl | H | H | 143-144 | |
| 192 | Cl | H | allyl | 4-F-C6H4 | -NH-CH(CH3)-CH2-OCH3 | H | H | | 451/453 |

TABLE 2-continued

| Compound Number | R1 | R2 | R3 | R4 | R6 | R7 | R8 | Melting Point ° | Mass (ES+_ |
|---|---|---|---|---|---|---|---|---|---|
| 193 | Cl | H | allyl | 4-F-phenyl | N-allyl-N-(pyridin-3-yl) | H | H | | 396/398 |
| 194 | Cl | H | allyl | 4-F-phenyl | NH-(pyridin-3-yl) | H | H | 140-142 | |
| 195 | Cl | H | allyl | 4-F-phenyl | NH-CH(CH3)-CH2-OH | H | H | 86-90 | |
| 196 | Cl | H | allyl | 4-F-phenyl | NH-CH(CH3)-CH2OH | H | H | — | 437/439 |
| 197 | Cl | H | allyl | 4-F-phenyl | NH-C(CH3)2-C≡CH | H | H | — | 445 |
| 198 | H | H | 3-fluoropropyl | 4-F-phenyl | RAC NH-CH(CF3)-CH2CH3 | H | H | — | 461 |

TABLE 2-continued

| Compound Number | R1 | R2 | R3 | R4 | R6 | R7 | R8 | Melting Point ° | Mass (ES+ |
|---|---|---|---|---|---|---|---|---|---|
| 199 | H | H | 3-fluoropropyl | 4-F-phenyl | RAC 1,1,1-trifluoro-2-propylamino | H | H | 89-90 | |
| 200 | H | H | trimethylsilylmethyl | 4-F-phenyl | Cl | H | H | 89-90 | |
| 201 | H | H | allyl/methylallyl | 4-F-phenyl | allylamino | H | H | 150-151 | |
| 202 | Cl | H | RAC isopropenyl-methyl | 4-F-phenyl | Cl | H | H | 146-147 | |
| 203 | H | H | H | 4-F-phenyl | NH$_2$ | H | H | 146-147 | |
| 204 | H | H | H | 4-F-phenyl | chloroacetamido | H | H | 250-250 | |

TABLE 2-continued
| Compound Number | R1 | R2 | R3 | R4 | R6 | R7 | R8 | Melting Point ° | Mass (ES+_ |
|---|---|---|---|---|---|---|---|---|---|
| 205 | H | H | 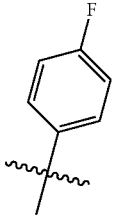 | 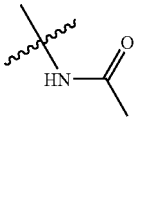 | 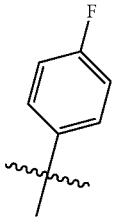 | H | H | 142-143 | |
| 206 | H | H | 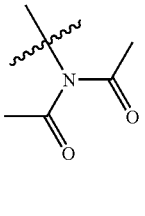 | 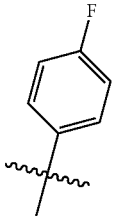 | 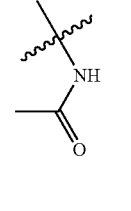 | H | H | 140-141 | |
| 207 | H | H | H | 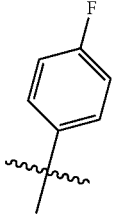 | 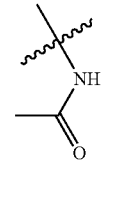 | H | H | 210-212 | |
| 208 | H | H | 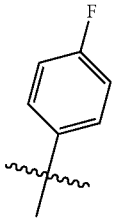 | 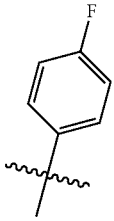 | 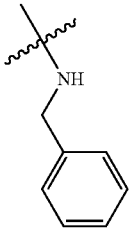 | H | H | 200-201 | |
| 209 | Me | H |  |  | Cl | H | H | 149-150 | |
| 210 | Me | H | H |  |  | H | H | 230-231 | |

TABLE 2-continued
| Compound Number | R1 | R2 | R3 | R4 | R6 | R7 | R8 | Melting Point ° | Mass (ES+_ |
|---|---|---|---|---|---|---|---|---|---|
| 211 | H | H | 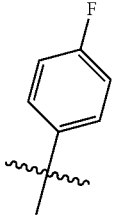 | 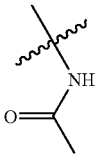 | 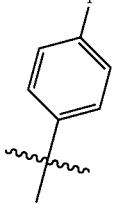 | H | H | 155-156 | |
| 212 | H | H | 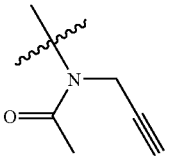 | 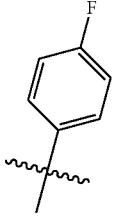 | 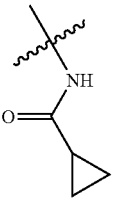 | H | H | 251-252 | |
| 213 | H | H | H | 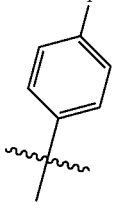 | 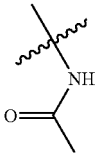 | H | H | 244-245 | |
| 214 | H | H | 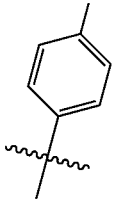 | 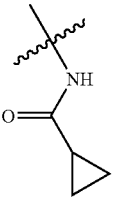 | 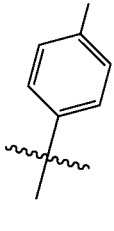 | H | H | — | 387 |
| 215 | H | H | 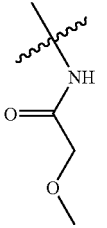 | | | H | H | 260-260 | |
| 216 | H | H | H | | | H | H | 250-251 | |

TABLE 2-continued
| Compound Number | R1 | R2 | R3 | R4 | R6 | R7 | R8 | Melting Point ° | Mass (ES+ |
|---|---|---|---|---|---|---|---|---|---|
| 217 | H | H | H | 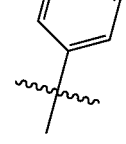 | 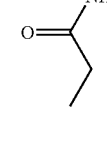 | H | H | 198-199 | |
| 218 | H | H | 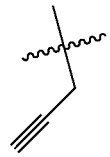 | 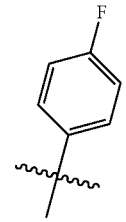 | 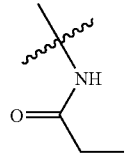 | H | H | 195-196 | |
| 219 | H | H | H | 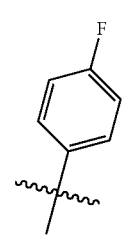 | 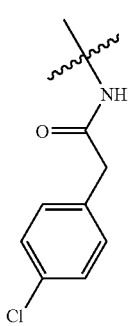 | H | H | 149-150 | |
| 220 | H | H | H | 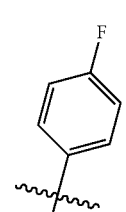 | 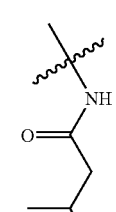 | H | H | 215-216 | |
| 221 | H | H | 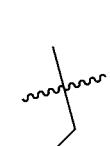 | 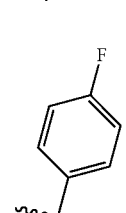 | 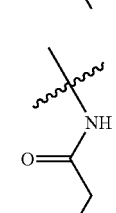 | H | H | 250-250 | |
| 222 | H | H | H | 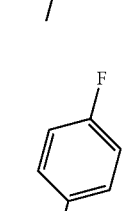 | 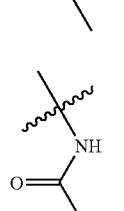 | H | H | 250-250 | |

TABLE 2-continued
| Compound Number | R1 | R2 | R3 | R4 | R6 | R7 | R8 | Melting Point ° | Mass (ES+ |
|---|---|---|---|---|---|---|---|---|---|
| 223 | H | H | H | 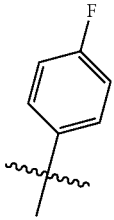 | 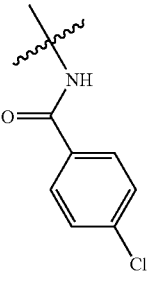 | H | H | 208-209 | |
| 224 | H | H | RAC 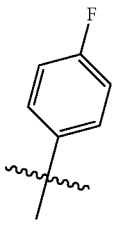 | 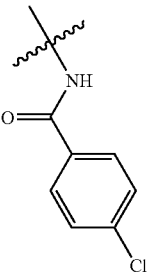 | 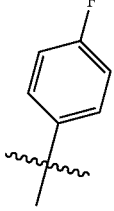 | H | H | 203-204 | |
| 225 | H | H | H | 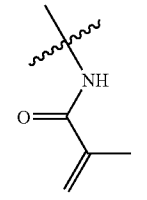 | 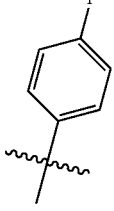 | H | H | 250-250 | |
| 226 | Me | H | H | 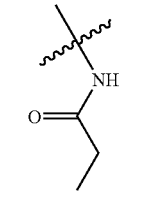 | 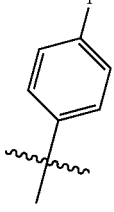 | H | H | 107-109 | |
| 227 | Me | H | 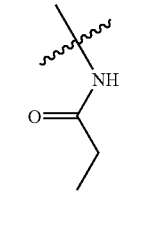 | | | H | H | 207-208 | |
| 228 | H | H | 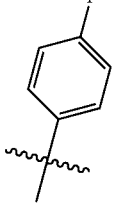 | | 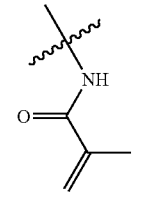 | H | H | 233-234 | |

TABLE 2-continued
| Compound Number | R1 | R2 | R3 | R4 | R6 | R7 | R8 | Melting Point ° | Mass (ES+) |
|---|---|---|---|---|---|---|---|---|---|
| 229 | H | H |  | 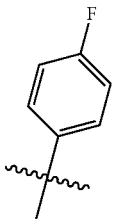 | 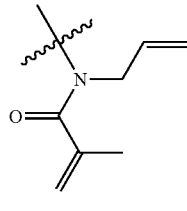 | H | H | 218-219 | |
| 230 | Me | H | H | 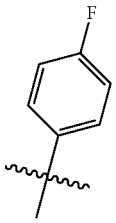 | 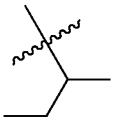 | H | H | — | 360 |
| 231 | Me | H |  | 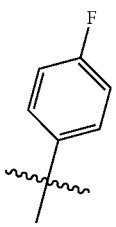 | 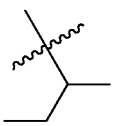 | H | H | — | 406 |
| 232 | H | H |  | 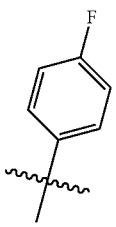 | 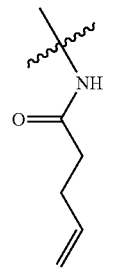 | H | H | 260-260 | |
| 233 | H | H |  | 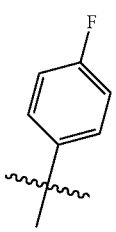 | 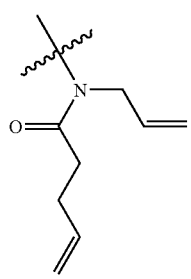 | H | H | | 467 |
| 234 | H | H | H | 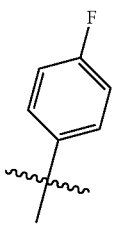 | 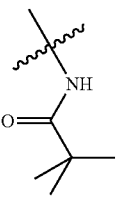 | H | H | 162-163 | |

TABLE 2-continued
| Compound Number | R1 | R2 | R3 | R4 | R6 | R7 | R8 | Melting Point ° | Mass (ES+) |
|---|---|---|---|---|---|---|---|---|---|
| 235 | H | H | H | 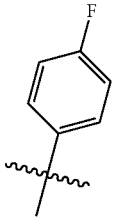 4-F-phenyl | 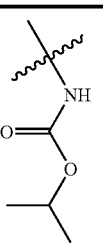 NHC(O)O-iPr | H | H | | 391 |
| 236 | H | H | H | 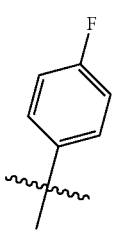 4-F-phenyl | 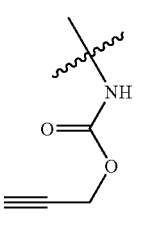 NHC(O)O-CH₂C≡CH | H | H | >250 | |
| 237 | H | H | H | 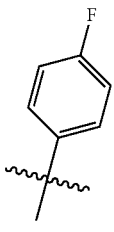 4-F-phenyl | 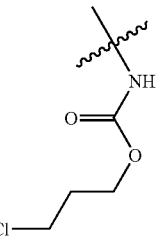 NHC(O)O-(CH₂)₃Cl | H | H | >250 | |
| 238 | H | H | H | 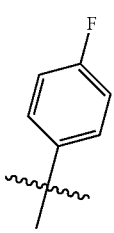 4-F-phenyl | 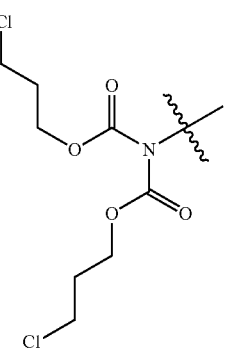 N[C(O)O-(CH₂)₃Cl]₂ | H | H | 233-234 | |
| 239 | H | H | H | 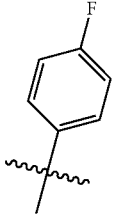 4-F-phenyl | 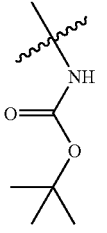 NHC(O)O-tBu | H | H | 226-227 | |
| 240 | H | H | 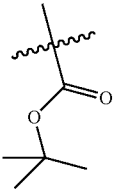 C(O)O-tBu | 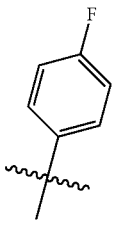 4-F-phenyl | 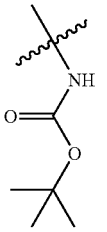 NHC(O)O-tBu | H | H | 146-147 | |

TABLE 2-continued

| Compound Number | R1 | R2 | R3 | R4 | R6 | R7 | R8 | Melting Point ° | Mass (ES+ |
|---|---|---|---|---|---|---|---|---|---|
| 241 | H | H | *tert-butyl ester* | 4-fluorophenyl | NH₂ | H | H | >250 | |
| 242 | H | H | *ethyl ester (CH₂CO₂Et)* | 4-fluorophenyl | *NH-C(O)-O-CH₂CH₂CH₂-Cl carbamate* | H | H | 181-182 | |
| 243 | H | H | *ethyl ester (CH₂CO₂Et)* | 4-fluorophenyl | *1,3-oxazinan-2-one (N-linked)* | H | H | 250-250 | |
| 244 | Me | H | H | 4-fluorophenyl | NH₂ | H | H | | 319 |
| 245 | H | H | H | 4-fluorophenyl | *NH-C(O)-CF(Cl)-CF₃* | H | H | | 449 |
| 246 | H | H | H | 4-fluorophenyl | *NH-C(O)-CH₂-CF₃* | H | H | >250 | |

TABLE 2-continued

| Compound Number | R1 | R2 | R3 | R4 | R6 | R7 | R8 | Melting Point ° | Mass (ES+) |
|---|---|---|---|---|---|---|---|---|---|
| 247 | H | H | H | 4-F-phenyl | -NHC(O)C(F)(F)C(F)(F)CF3 | H | H | 210-211 | |
| 248 | H | H | H | 4-F-phenyl | -NHC(O)-cyclopropyl | H | H | | 387 |
| 249 | H | H | C(O)-cyclopropyl | 4-F-phenyl | -NHC(O)-cyclopropyl | H | H | >255 | |
| 250 | H | H | H | 4-F-phenyl | -NHC(O)-(1-cyano-cyclopropyl) | H | H | >250 | |
| 251 | H | H | H | 4-F-phenyl | -NHC(O)-(1-methyl-cyclopropyl) | H | H | 233-234 | |
| 252 | H | H | H | 4-F-phenyl | ABS -NHC(O)-(2-fluoro-cyclopropyl) | H | H | 139 | |

TABLE 2-continued
| Compound Number | R1 | R2 | R3 | R4 | R6 | R7 | R8 | Melting Point ° | Mass (ES+ |
|---|---|---|---|---|---|---|---|---|---|
| 253 | H | H | H | 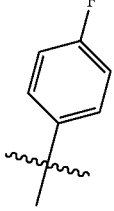 | 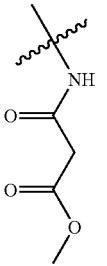 | H | H | >255 | |
| 254 | H | H | H | 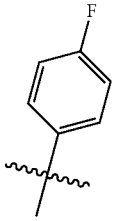 | —CN | H | H | 139-140 | |
| 255 | H | H | H | 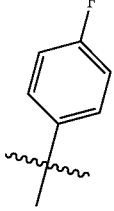 | 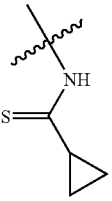 | H | H | 199-200 | |
| 256 | H | H | H | 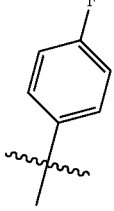 | 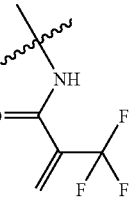 | H | H | >260 | |
| 257 | H | H | 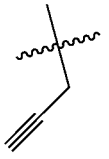 | 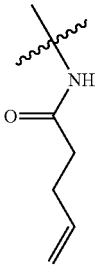 | 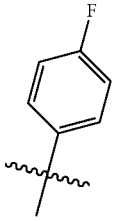 | H | H | 218-220 | |
| 258 | H | H | H | 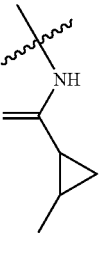 | | H | H | — | 403 |

TABLE 2-continued
| Compound Number | R1 | R2 | R3 | R4 | R6 | R7 | R8 | Melting Point ° | Mass (ES+ |
|---|---|---|---|---|---|---|---|---|---|
| 259 | Me | H | H | 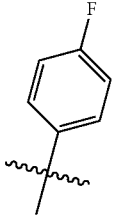 | 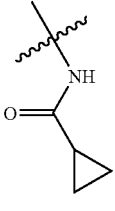 | H | H | — | 387 |
| 260 | Me | H | H | 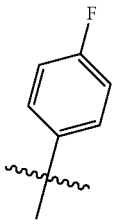 | 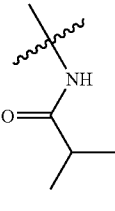 | H | H | — | 389 |
| 261 | Me | H | H | 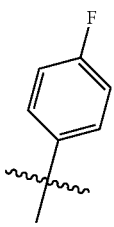 | 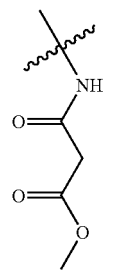 | H | H | 221-222 | |
| 262 | H | H | H | 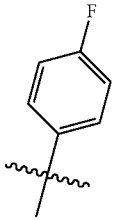 | 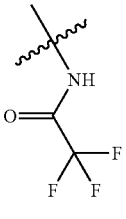 | H | H | 253-254 | |
| 263 | H | H | H | 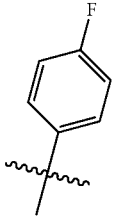 | 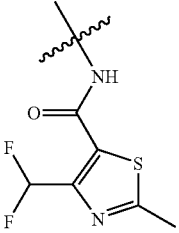 | H | H | 150-152 | |
| 264 | H | H | H | 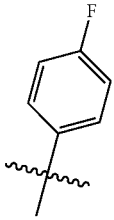 | 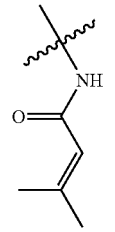 | H | H | 204-206 | |

TABLE 2-continued
| Compound Number | R1 | R2 | R3 | R4 | R6 | R7 | R8 | Melting Point ° | Mass (ES+ |
|---|---|---|---|---|---|---|---|---|---|
| 265 | H | H | H | 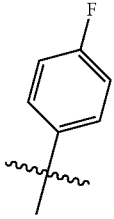 | 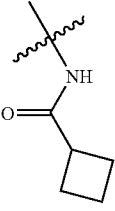 | H | H | 121-122 | |
| 266 | H | H | H | 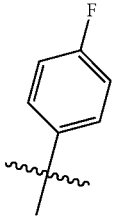 | 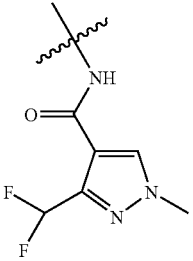 | H | H | 227-230 | |
| 267 | Me | H | H | 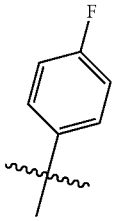 | 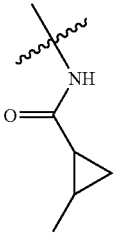 | H | H | >250 | |
| 268 | Me | H | 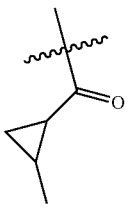 | 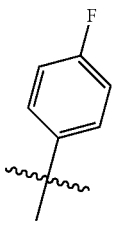 | 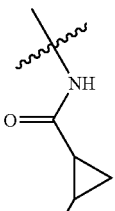 | H | H | >250 | |
| 268 | Me | H | 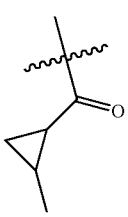 | 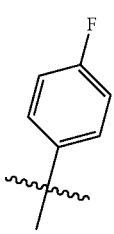 | 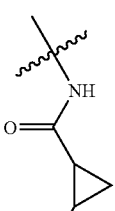 | H | H | >250 | |
| 269 | Me | H | 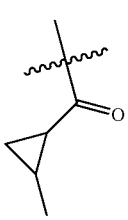 | 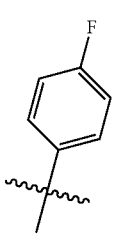 | 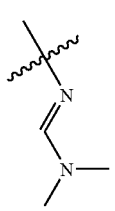 | H | H | — | 401 |

TABLE 2-continued
| Compound Number | R1 | R2 | R3 | R4 | R6 | R7 | R8 | Melting Point ° | Mass (ES+_ |
|---|---|---|---|---|---|---|---|---|---|
| 270 | H | H | H | 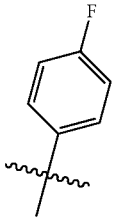 | 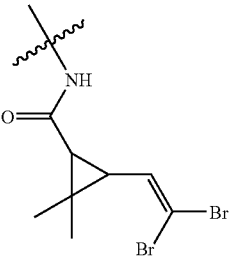 | H | H | 204-205 | |
| 271 | H | H | H | 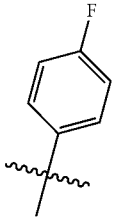 | 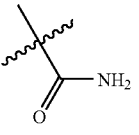 | H | H | 140-141 | |
| 272 | H | H | 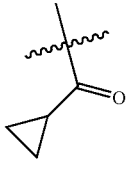 | 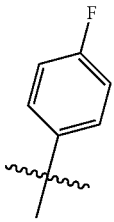 | 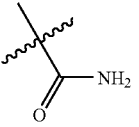 | H | H | 123-125 | |
| 273 | H | H | H | 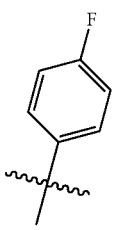 | 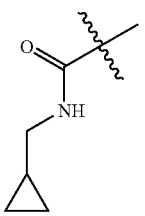 | H | H | >260 | |
| 274 | H | H | H | 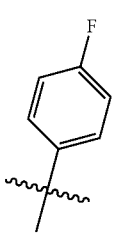 | 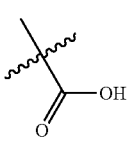 | H | H | 242-243 | |
| 275 | H | H | H | 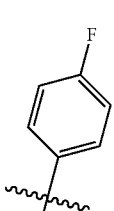 | 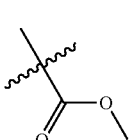 | H | H | 220-222 | |

TABLE 2-continued
| Compound Number | R1 | R2 | R3 | R4 | R6 | R7 | R8 | Melting Point ° | Mass (ES+ |
|---|---|---|---|---|---|---|---|---|---|
| 383 | H | H | H | 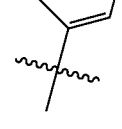 | 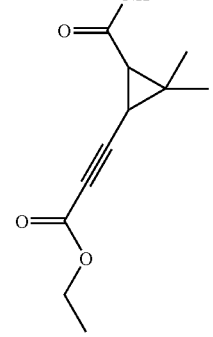 | H | H | 175-177 | |
| 384 | H | H | 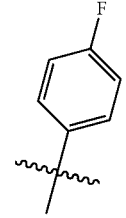 | 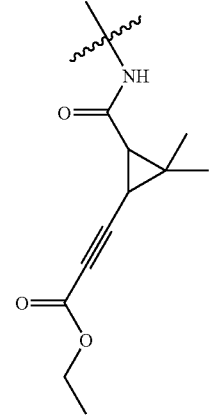 | 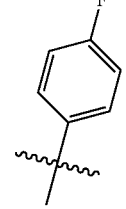 | H | H | 240-244 | |
| 385 | H | H | H | 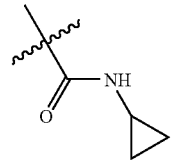 | 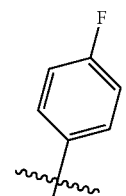 | H | H | — | 373 |
| 386 | H | H | 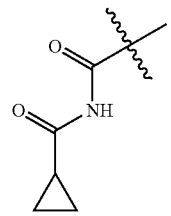 | 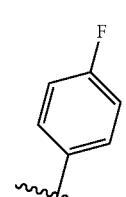 | 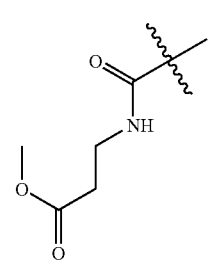 | H | H | — | 401 |
| 387 | H | H | H |  |  | H | H | 247-250 | |

TABLE 2-continued

| Compound Number | R1 | R2 | R3 | R4 | R6 | R7 | R8 | Melting Point ° | Mass (ES+ |
|---|---|---|---|---|---|---|---|---|---|
| 388 | H | H | H | 4-fluorophenyl | -C(CH3)(-)C(O)NHCH2CF3 | H | H | 184-191 | |
| 389 | H | H | H | 4-fluorophenyl | -C(CH3)(-)C(O)NHCH2CH2OCH3 | H | H | 229-231 | |
| 390 | H | H | H | 4-fluorophenyl | -C(CH3)(-)C(=NH)NHN=C(CH3)2 | H | H | 226-233 | |
| 391 | H | H | H | 4-fluorophenyl | -C(CH3)(-)C(O)NHOCH2CH(CH3)2 | H | H | 185-189 | |
| 392 | H | H | H | 4-fluorophenyl | -C(CH3)(-)(2H-tetrazol-5-yl) | H | H | 230-236 | |
| 393 | H | H | H | 4-fluorophenyl | -C(CH3)(-)C(O)NH(3-chlorophenyl) | H | H | 157-161 | |

TABLE 2-continued
| Compound Number | R1 | R2 | R3 | R4 | R6 | R7 | R8 | Melting Point ° | Mass (ES+ |
|---|---|---|---|---|---|---|---|---|---|
| 394 | H | H | H | 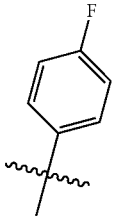 | 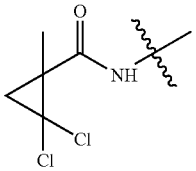 | H | H | >250 | |
| 395 | H | H | H | 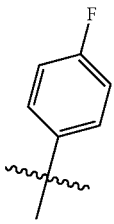 | 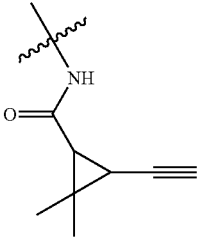 | H | H | >250 | |
| 396 | H | H | H | 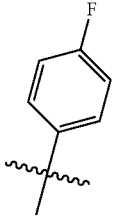 | 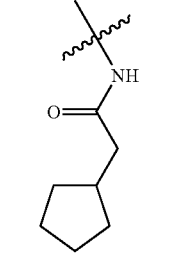 | H | H | >260 | |
| 397 | H | H | H | 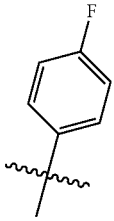 | 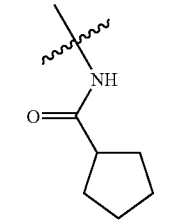 | H | H | 266-268 | |
| 398 | H | H | H | 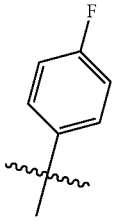 | 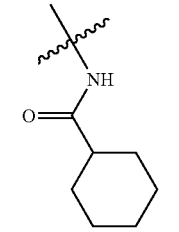 | H | H | 138-140 | |
| 399 | H | H | H | 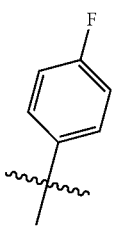 | 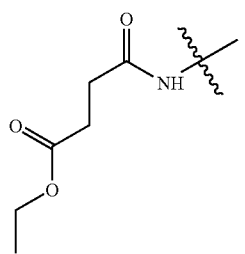 | H | H | >260 | |

TABLE 2-continued
| Compound Number | R1 | R2 | R3 | R4 | R6 | R7 | R8 | Melting Point ° | Mass (ES+ |
|---|---|---|---|---|---|---|---|---|---|
| 400 | H | H | H | 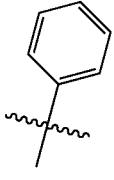 | 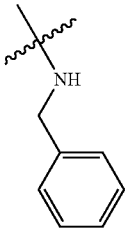 | H | H | >250 | |
| 401 | H | H | H | 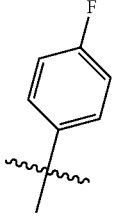 | 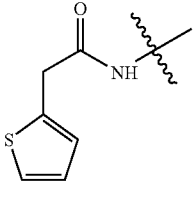 | H | H | >250 | |
| 401 | H | H | H | 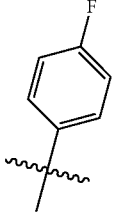 | 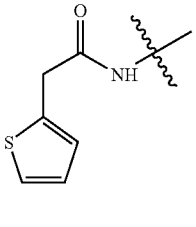 | H | H | >250 | |
| 402 | H | H | H | 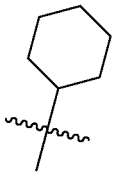 | Cl | H | H | 233-234 | |
| 403 | H | H | H | 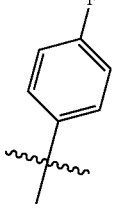 | 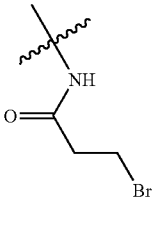 | H | H | 168-169 | |
| 404 | H | H | H | 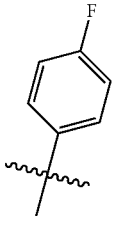 | 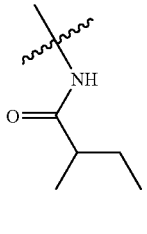 | H | H | 242-243 | |
| 405 | H | H | H | 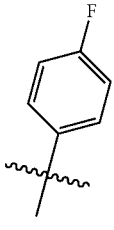 | 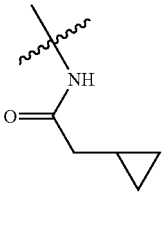 | H | H | 248-250 | |

TABLE 2-continued
| Compound Number | R1 | R2 | R3 | R4 | R6 | R7 | R8 | Melting Point ° | Mass (ES+) |
|---|---|---|---|---|---|---|---|---|---|
| 406 | H | H | H | 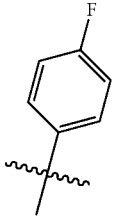 | 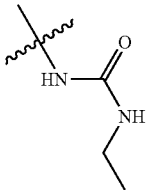 | H | H | 242-243 | |
| 407 | H | H | H | 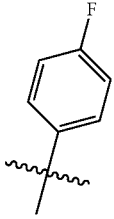 | 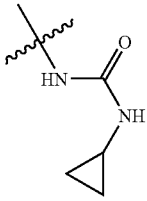 | H | H | 140-150 | |
| 408 | H | H | H | 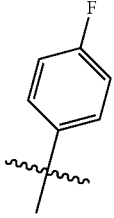 | 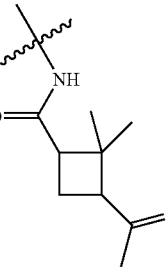 | H | H | 85-88 | |
| 409 | H | H | H | 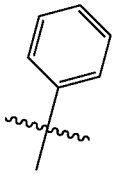 | 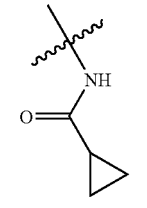 | H | H | 73-76 | |
| 410 | H | H | H | 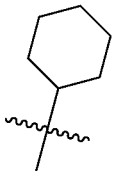 | 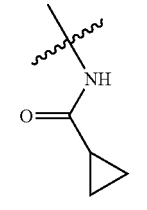 | H | H | 94-95 | |
| 411 | H | H | H | 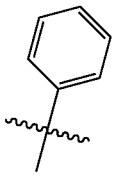 | 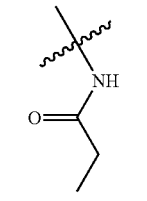 | H | H | >250 | |

TABLE 2-continued
| Compound Number | R1 | R2 | R3 | R4 | R6 | R7 | R8 | Melting Point ° | Mass (ES+ |
|---|---|---|---|---|---|---|---|---|---|
| 412 | H | H | H | 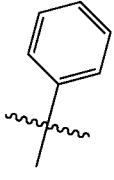 | 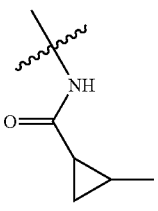 | H | H | 259-260 | |
| 413 | H | H | H | 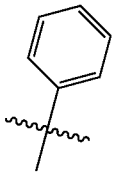 | 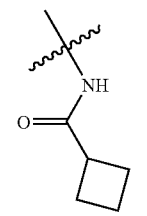 | H | H | 239-240 | |
| 414 | H | H | 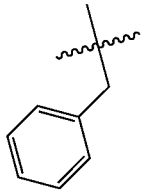 | 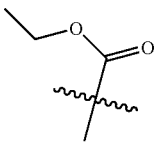 | F | H | H | >260 | |
| 415 | H | H | 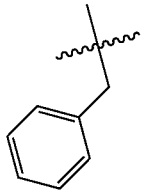 | 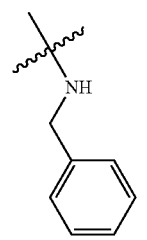 | 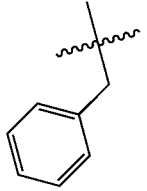 | H | H | >260 | |
| 416 | H | H | 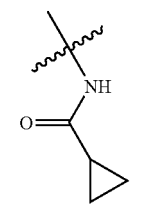 | 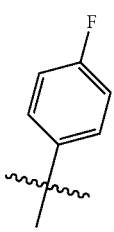 | 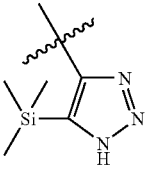 | H | H | 201-202 | |
| 417 | H | H | H | 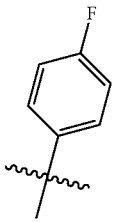 | 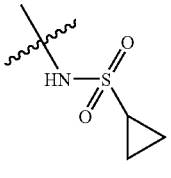 | H | H | 180-182 | |
| 418 | H | H | H |  |  | H | H | 237-239 | |

TABLE 2-continued
| Compound Number | R1 | R2 | R3 | R4 | R6 | R7 | R8 | Melting Point ° | Mass (ES+_ |
|---|---|---|---|---|---|---|---|---|---|
| 419 | H | H | H | 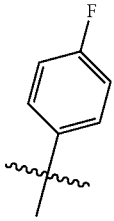 | 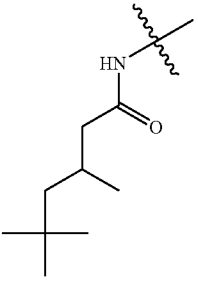 | H | H | — | 445.2 |
| 420 | H | H | H | 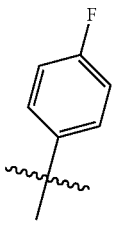 | 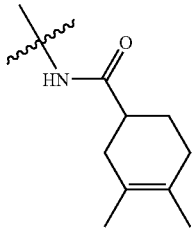 | H | H | 283-285 | |
| 421 | H | H | H | 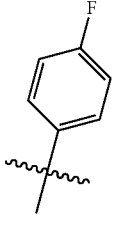 | 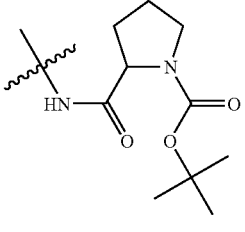 | H | H | — | 502 |
| 422 | H | H | H | 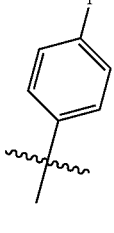 | 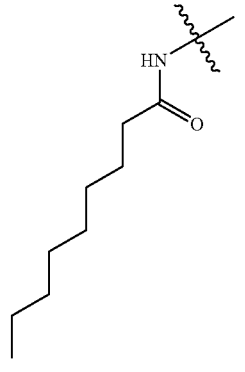 | H | H | — | 445 |
| 423 | H | H | H | 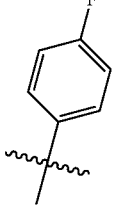 | 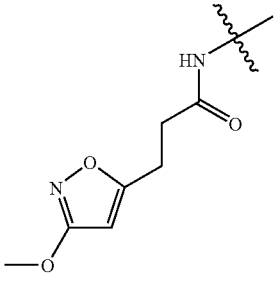 | H | H | — | 458 |

TABLE 2-continued
| Compound Number | R1 | R2 | R3 | R4 | R6 | R7 | R8 | Melting Point ° | Mass (ES+_ |
|---|---|---|---|---|---|---|---|---|---|
| 424 | H | H | H | 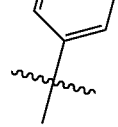 | 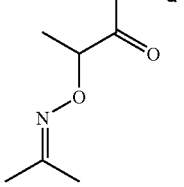 | H | H | — | 432 |
| 425 | H | H | H | 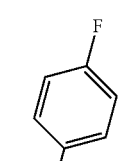 | 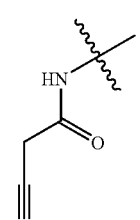 | H | H | — | 372 |
| 426 | H | H | H | 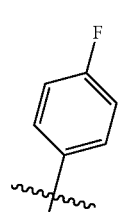 | 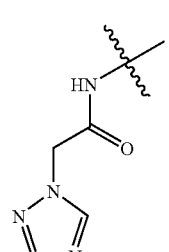 | H | H | — | 414 |
| 427 | H | H | H | 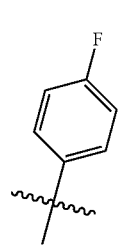 | 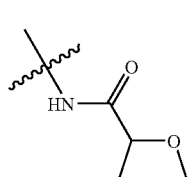 | H | H | — | 403 |
| 428 | H | H | H | 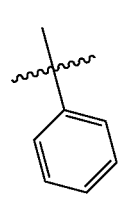 | 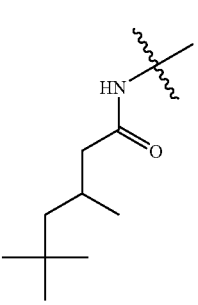 | H | H | — | 427 |
| 429 | H | H | H | 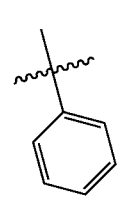 | 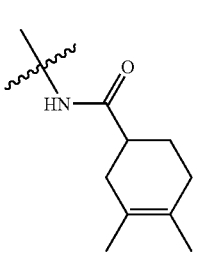 | H | H | — | 423 |

TABLE 2-continued

| Compound Number | R1 | R2 | R3 | R4 | R6 | R7 | R8 | Melting Point ° | Mass (ES+_ |
|---|---|---|---|---|---|---|---|---|---|
| 430 | H | H | H | phenyl | N-Boc-prolinamide | H | H | — | 484 |
| 431 | H | H | H | phenyl | nonanamide | H | H | — | 427 |
| 432 | H | H | H | phenyl | 3-(3-methoxyisoxazol-5-yl)propanamide | H | H | — | 440 |
| 433 | H | H | H | phenyl | 2-((propan-2-ylideneamino)oxy)propanamide | H | H | — | 414 |
| 434 | H | H | H | phenyl | 2-cyanoacetamide | H | H | — | 354 |

TABLE 2-continued
| Compound Number | R1 | R2 | R3 | R4 | R6 | R7 | R8 | Melting Point ° | Mass (ES+_ |
|---|---|---|---|---|---|---|---|---|---|
| 435 | H | H | H | 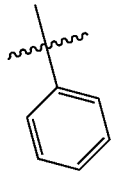 | 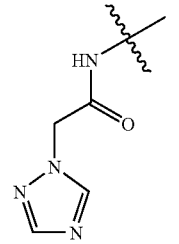 | H | H | — | 396 |
| 436 | H | H | H | 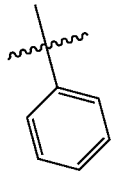 | 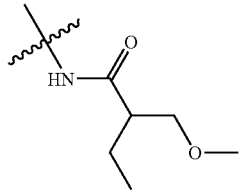 | H | H | — | 401 |
| 437 | H | H | H | 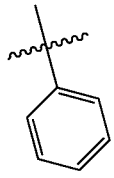 | 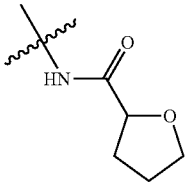 | H | H | — | 385 |
| 438 | H | H | 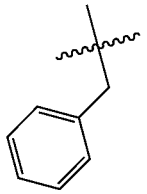 | 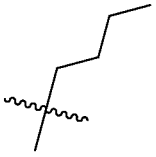 | F | H | H | — | 360 |
| 439 | H | H | H | 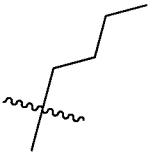 | NH$_2$ | H | H | 235-240 | |
| 440 | H | H | H | 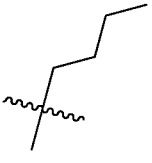 | 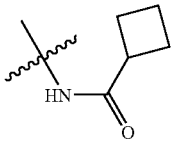 | H | H | — | 349 |
| 441 | H | H | H | 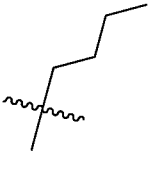 | F | H | H | 235-240 | |
| 442 | H | H | H | 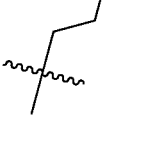 | 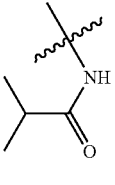 | H | H | 102-104 | |

TABLE 2-continued

| Compound Number | R1 | R2 | R3 | R4 | R6 | R7 | R8 | Melting Point ° | Mass (ES+ |
|---|---|---|---|---|---|---|---|---|---|
| 443 | H | H | H | pentyl | cyclopropylcarbonyl-NH- | H | H | 158-160 | |
| 444 | H | H | H | pentyl | propanoyl-NH- | H | H | 102-104 | |
| 445 | Me | H | H | phenyl | NH$_2$ | H | H | 149-151 | |
| 446 | H | H | H | 4-fluorophenyl | pyridine-2-carbonyl-NH- | H | H | 149-152 | |
| 447 | Me | H | H | phenyl | isobutyryl-NH- | H | H | >260 | |
| 448 | Me | H | H | phenyl | propanoyl-NH- | H | H | 260-999 | |
| 449 | Me | H | H | phenyl | cyclopentylcarbonyl-NH- | H | H | 206-207 | |
| 450 | Me | H | H | phenyl | 3-methylbutanoyl-NH- | H | H | 260-999 | |

TABLE 2-continued
| Compound Number | R1 | R2 | R3 | R4 | R6 | R7 | R8 | Melting Point ° | Mass (ES+) |
|---|---|---|---|---|---|---|---|---|---|
| 451 | Me | H | H | 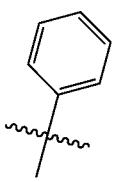 | 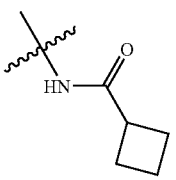 | H | H | 152-153 | |
| 452 | Me | H | H | 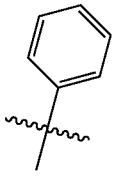 | 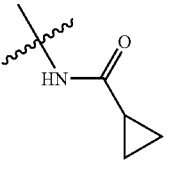 | H | H | 182-183 | |
| 453 | H | H | H | 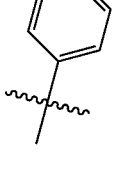 | 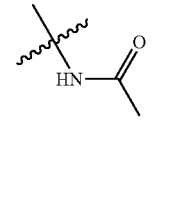 | H | H | 168-169 | |
| 454 | H | H | H | 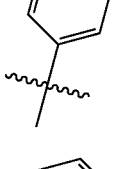 | 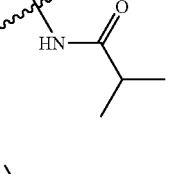 | H | H | 168-169 | |
| 455 | H | H | H | 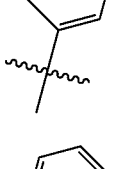 | 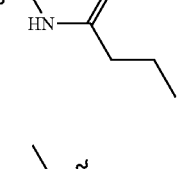 | H | H | — | 357 |
| 456 | Me | H | H | 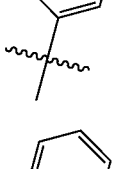 | 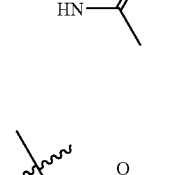 | H | H | — | 343 |
| 457 | H | H | H |  | 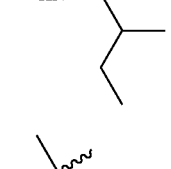 | H | H | — | 371 |
| 458 | H | H | 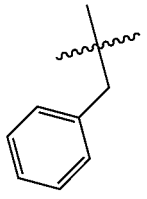 | 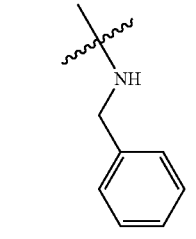 | | H | H | 178-180 | |

TABLE 2-continued

| Compound Number | R1 | R2 | R3 | R4 | R6 | R7 | R8 | Melting Point ° | Mass (ES+) |
|---|---|---|---|---|---|---|---|---|---|
| 459 | H | H | benzyl (CH₂-phenyl) | isopropyl-like (CH(CH₃)-CH(CH₃)₂) | Cl | H | H | 252-253 | |
| 460 | H | H | H | 2,6-difluorophenyl-CH(CH₃)- | NH₂ | H | H | >260 | 323 |
| 461 | H | H | H | 2-(benzylamino)-3-fluorophenyl-CH(CH₃)- | NH₂ | H | H | — | 410 |

TABLE 2a

HPLC Retention Times of Certain Compounds of Table 2

| Compound Number | Retention Time (Min) | Method |
|---|---|---|
| 419 | 1.76 | A |
| 421 | 1.49 | A |
| 422 | 1.8 | A |
| 423 | 1.36 | A |
| 424 | 1.45 | A |
| 425 | 1.22 | A |
| 426 | 1.15 | A |
| 427 | 1.33 | A |
| 428 | 1.72 | A |
| 429 | 1.65 | A |
| 430 | 1.46 | A |
| 431 | 1.77 | A |
| 432 | 1.33 | A |
| 433 | 1.41 | A |
| 434 | 1.2 | A |
| 435 | 1.08 | A |
| 436 | 1.4 | A |
| 437 | 1.3 | A |

Method: see under "Examples" for details of Method A and Method B

TABLE 3

| Compound number | R1 | R2 | R3 | R4 | R6 | R7 | R8 | Melting point (° C.) | Mass Spectrum (ES+) |
|---|---|---|---|---|---|---|---|---|---|
| 276 | H | H | H | 4-fluorophenyl | H | H | H | 255-260 | |

TABLE 3-continued

| Compound number | R1 | R2 | R3 | R4 | R6 | R7 | R8 | Melting point (° C.) | Mass Spectrum (ES+) |
|---|---|---|---|---|---|---|---|---|---|
| 277 | —H | —H | RAC (allyl) | 4-F-phenyl | —H | —H | —H | 185-187 | |
| 278 | —H | —H | CH₂CH₂F | 4-F-phenyl | —H | —H | —H | 122-124 | |
| 279 | —H | —H | vinyl | 4-F-phenyl | —H | —H | —H | — | 317 |
| 280 | —H | —H | CH₂OCH₃ | 4-F-phenyl | —S—CH₃ | —H | —H | 137-138 | |
| 281 | —H | —H | CH₂OCH₃ | 4-F-phenyl | —NH—CH(CH₃)CH₂OCH₃ | —H | —H | — | 422 |
| 282 | —H | —H | —H | 4-F-phenyl | —NH₂ | —H | —H | 255-255 | |

TABLE 3-continued

| Compound number | R1 | R2 | R3 | R4 | R6 | R7 | R8 | Melting point (° C.) | Mass Spectrum (ES+) |
|---|---|---|---|---|---|---|---|---|---|
| 283 | —H | —H | —H | 4-F-phenyl | —NHC(O)CH₃ | —H | —H | — | 348 |
| 284 | —H | —H | —H | 4-F-phenyl | —NHC(O)CH₂CH(CH₃)₂ | —H | —H | 235-236 | |
| 285 | —H | —H | —CH₂C≡CH | 4-F-phenyl | —NHC(O)CH₂CH(CH₃)₂ | —H | —H | 188-189 | |
| 286 | —H | —H | —CH₂C≡CH | 4-F-phenyl | —N(CH₂C≡CH)C(O)CH₂CH(CH₃)₂ | —H | —H | — | 466 |
| 287 | —H | —H | —H | 4-F-phenyl | —NHC(O)-cyclopropyl | —H | —H | 214-215 | |
| 288 | —H | —H | —H | 4-F-phenyl | —NHC(O)CH(CH₃)₂ | —H | —H | 221-222 | |

TABLE 3-continued

| Compound number | R1 | R2 | R3 | R4 | R6 | R7 | R8 | Melting point (° C.) | Mass Spectrum (ES+) |
|---|---|---|---|---|---|---|---|---|---|
| 289 | H | H | H | 4-F-phenyl | NHC(O)CH2CH3 | H | H | 235-236 | |
| 290 | H | H | H | 4-F-phenyl | NHC(O)C(CH3)3 | H | H | 236-237 | |
| 291 | H | H | H | 4-F-phenyl | NHC(O)OCH(CH3)2 | H | H | 245-246 | |
| 292 | H | H | H | 4-F-phenyl | NHC(S)CH(CH3)2 | H | H | 240-241 | |

The present invention also provides a compound of formula (I) as defined above with the provisos that (i) when $X^1$ is CH, $X^2$ is $CR^5$ and $R^5$ and $R^6$ are both H, $R^4$ is not 4-fluorophenyl and (ii) the compound of formula (I) is not:

3-phenyl-2-pyridin-4-yl-1H-pyrrolo[3,2-b]pyridine 3-(3-chloro-4-fluoro-phenyl)-2-pyridin-4-yl-1H-pyrrolo[3,2-b]pyridine 3-(3-chloro-phenyl)-2-pyridin-4-yl-1H-pyrrolo[3,2-b]pyridine 3-(3-trifluoro-phenyl)-2-pyridin-4-yl-1H-pyrrolo[3,2-b]pyridine 3-(3-methoxy-phenyl)-2-pyridin-4-yl-1H-pyrrolo[3,2-b]pyridine 3-(2-methylphenyl)-2-pyridin-4-yl-1H-pyrrolo[3,2-b]pyridine 3-(2-methoxyphenyl)-2-pyridin-4-yl-1H-pyrrolo[3,2-b]pyridine 1-methyl-2-pyridin-4-yl-3-(3-trifluoromethyl-phenyl)-1H-pyrrolo[3,2-b]pyridine 1-methyl-3-(3-chloro-4-fluoro-phenyl)-2-pyridin-4-yl-1H-pyrrolo[3,2-b]pyridine 3-(4-fluorophenyl)-2-(2-(2-hydroxyethyl-amino)-pyridin-4-yl)-1H-pyrrolo[3,2-b]pyridine, 3-(4-fluorophenyl)-2-(2-[HO(CH2)2O(CH2)2NH]-pyridin-4-yl)-1H-pyrrolo[3,2-b]pyridine, 3-(4-fluorophenyl)-2-(2-(2-methylamino-ethylamino)-pyridin-4-yl)-1H-pyrrolo[3,2-b]pyridine, 3-(4-fluorophenyl)-2-(2-(3-methoxy-propyl-amino)-pyridin-4-yl)-1H-pyrrolo[3,2-b]pyridine, 3-(4-fluorophenyl)-2-(2-n-propylamino-pyridin-4-yl)-1H-pyrrolo[3,2-b]pyridine, 3-(4-fluorophenyl)-2-(2-(3-hydroxy-propyl-amino)-pyridin-4-yl)-1H-pyrrolo[3,2-b]pyridine, 3-(4-fluorophenyl)-2-(2-methylamino-pyridin-4-yl)-1H-pyrrolo[3,2-b]pyridine or 3-(4-fluorophenyl)-2-(2-acetylamino pyridin-4-yl)-1H-pyrrolo[3,2-b]pyridine.

In a further aspect, the invention relates to a process for the preparation of a compound of formula (I) as claimed in claim 1, comprising:

a) reacting a ketone of formula (D)

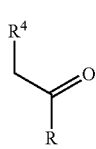

wherein R⁴ is as defined in claim 1, and R is a group of formula

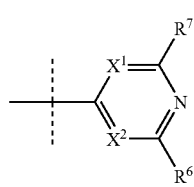

wherein X¹, X², R⁶ and R⁷ are as defined in claim 1, with an aminopyridine of formula (E)

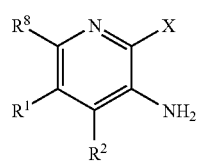

wherein R¹, R² and R⁸ are as defined in claim 1, and X is a halogen, to give an enamine of formula (F),

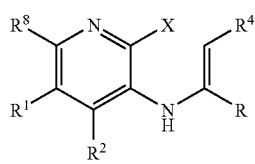

cyclising to give an azaindole of formula (G),

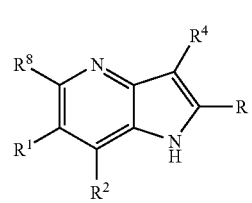

and optionally alkylating to give a compound of formula (I) as defined in claim 1; or b) reacting an azaindole of formula (K)

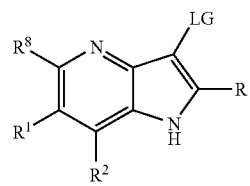

wherein R¹, R² and R⁸ are as defined in claim 1, R is as defined above, and LG is a leaving group with a compound of formula R⁴—B(OH)₂ wherein R⁴ is as defined in claim 1, to give a compound of formula (G) as defined above, and optionally alkylating to give a compound of formula (I) as defined in claim 1;

c) reacting a compound of formula (G) above with a compound of formula R³-LG wherein LG is a leaving group to give a compound of formula (I) as defined in claim 1;

d) reacting a compound of formula (S)

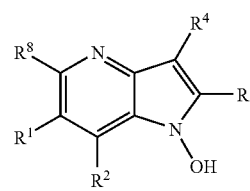

wherein R¹, R², R⁴, and R⁸ are defined in claim 1, and R is as defined above, with a compound of formula R¹²-LG wherein R¹² is as defined in claim 1 and LG is a leaving group, to give a compound of formula (T)

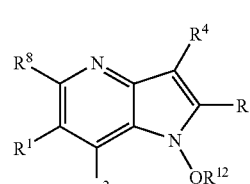

wherein R¹, R², R⁴, R⁸, and R¹² are defined in claim 1, and R is as defined above, or e) converting a compound of formula (I) as defined in claim 1 to a salt of N-oxide thereof. Obviously, the skilled person will appreciate that the compounds of the invention can be made by various other methods.

Compounds of the invention and for use in the methods of the invention can be made, for example, by following the reaction scheme and the methods detailed below. The starting materials used for the preparation of the compounds of the invention may be purchased from usual commercial suppliers. The starting materials as well as the intermediates may be purified before use in the next step by state of the art methodologies such as chromatography, crystallization, distillation and filtration.

The schemes listed below to exemplify the possible preparation methods for the compounds of general formula I are suggestions that might be modified by those skilled in the art to reach the disclosed compounds. Many of the steps detailed below can be found in *J. Med. Chem.* 2003, 46, 4702-4713.

Compounds of general formula (I) previously described and listed in the tables above may be prepared following the procedure described in scheme 1:

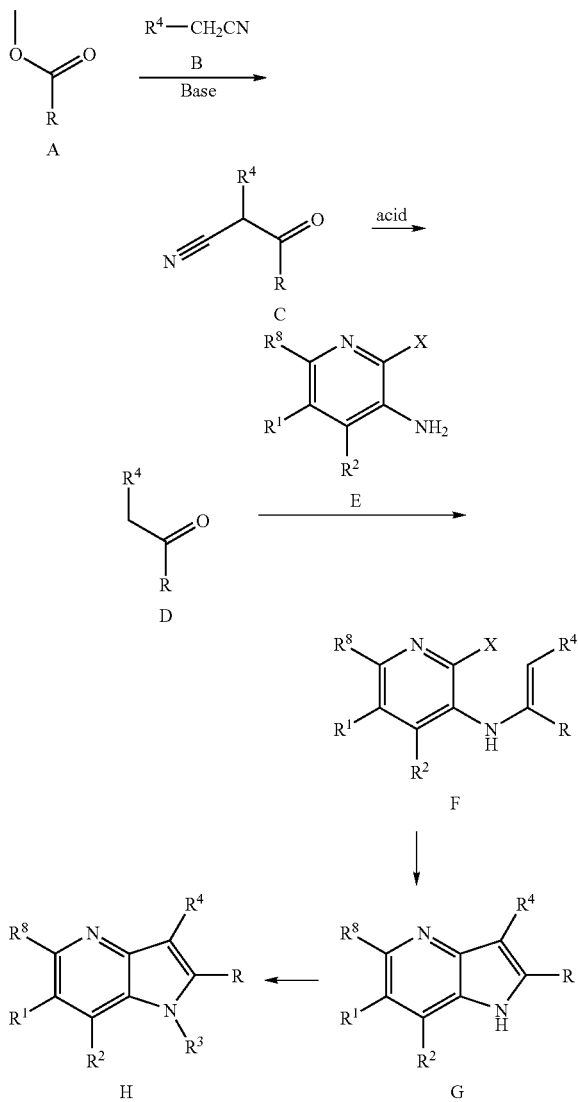

wherein R is:

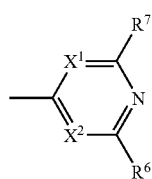

and $X^1$ and $X^2$, $R^1$ to $R^8$ are as defined above and X is halogen.

Compounds of formula C can be obtained by reaction between an ester of formula A and an acetonitrile derivative of formula B in the presence of a base such as sodium methoxide or potassium t-butoxide in suitable alcoholic solvent. (see *J. Med. Chem.* 2003, 46, 4702-4713).

Compounds of formula A are generally commercially available but might be prepared by state of the art procedures from the corresponding acid, nitrile, or methyl derivative by esterification, hydrolysis or oxidation reactions, respectively.

Compounds of formula B, such as phenyl acetonitrile, 4-fluorophenyl acetonitrile or 3-methylphenyl acetonitrile and related compounds are commercially available.

Acidic treatment of compounds of formula C in suitable aqueous acid such as hydrobromic acid results in hydrolysis and decarboxylation leading to compound of formula D.

Further condensation of D with a 3-amino pyridine of formula E results in a formation of an enamine of formula F where X is a halogen such as bromo, chloro or iodo. The reaction may be performed in an aromatic solvent such as benzene, toluene or xylene in the presence of a catalytic amount of acid such as p-toluene sulfonic acid.

Alternatively, compound F may exist as its enamine-imine equilibrium; both compounds might be separated under state of the art purification condition such as chromatography.

Pyridines of formula E, such as 2-chloro-3-amino pyridine, 2-chloro-5-methyl pyridine or 2,5-dichloro-3-amino pyridine, may be commercially available or may be prepared by known methodologies. For example, by reduction of the corresponding nitro derivative (see *J. Chem. Soc.*, 1952, 2042). As a further example, (2,6-Dichloro-3-nitro-pyridin-4-yl)-acetic acid methyl ester can be prepared by vicarious nucleophilic substitution on the parent 2,6-Dichloro-3-nitro-pyridine (see *Liebigs Ann.* 1997, 1805-1816) followed by reduction of the nitro group.

The azaindole (1H-Pyrrolo[3,2-b]pyridine) of formula G is obtained by cyclisation of the enamine F in the presence of a tertiary amine base such as DABCO and a palladium catalyst such as palladium acetate (II) or dichlorobis(triphenylphosphine) palladium (II) in an inert solvent such as dimethylformamide or dimethylacetamide (see *J. Org. Chem.* 1997, 62, 2676-2677).

Compounds of formula H, where $R^3$ is not hydrogen may be obtained by alkylation or acylation of compounds of formula G. This alkylation can be realized with an alkylating agent of formula $R^3$—Y (where Y is a leaving group such as halogen, triflate, mesylate and the like) in the presence of a base such as sodium hydride or lithium hexamethyldisilazane in an aprotic solvent such as dimethylformamide or tetrahydrofuran. Compounds of formula G may also be obtained by acylation in the presence of an acylating agent such as $R^3$COX (where X is a halogen) in the presence of a base such as sodium hydride or lithium hexamethyldisilazane in an aprotic solvent such as dimethylformamide or tetrahydrofuran.

Scheme 2 describes an alternative method for the preparation of compound of formula (I):

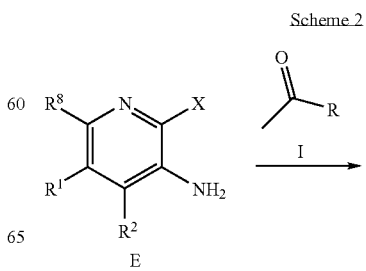

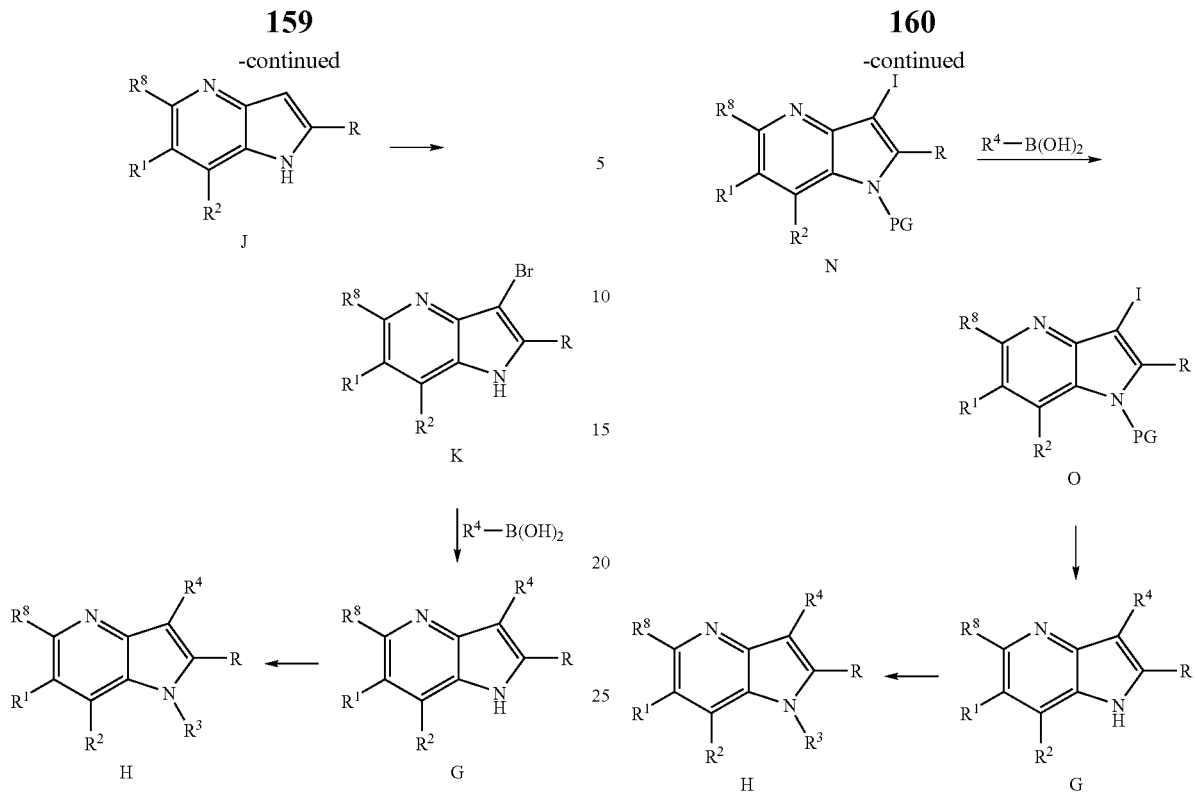

Compounds of formula J may be obtained in a single step condensation-cyclisation of a compound of formula E and compound of formula I. The reaction is carried out in the presence of a base such as potassium phosphate or potassium carbonate, a dehydrating agent such as magnesium or sodium sulphate and a palladium catalyst preferably (di-t-butylphoshino) palladium in an inert solvent such as dimethylformamide or dimethylacetamide under an inert atmosphere in a closed vessel. (see: *Angew. Chem. Int. Ed. Eng.* 2004, 4526-4528).

Compounds of formula J can regioselectively be brominated in the presence of bromine or N-bromosuccinimide in a solvent such as carbon tetrachloride or DMF to give compound of formula K (see Synthesis 1982, 1096). Compounds of formula G can be obtained by further treatment of K in the presence of a boronic acid of formula $R^4B(OH)_2$ (where $R^4$ is as previously defined) under Suzuki cross coupling conditions (see: *Chem. Comm.*, 1979, 866) under thermal or microwave conditions.

Compounds of type H may then be obtained following the procedure described above for scheme 1.

Scheme 3 describes a further alternative method for the preparation of compound of formula (I).

Scheme 3

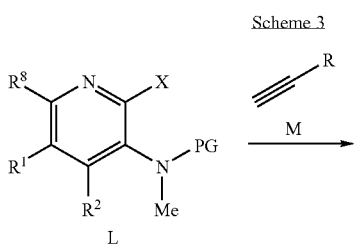

Compounds of formula L (where PG is a protective group such as methyl, acetate, benzyl, mesylate, tosylate and the like) may be obtained by sequential protection of the corresponding amino pyridine E (see "Protective groups in organic chemistry" Greene and Wuts $4^{th}$ edition, Wiley Interscience). Compounds of formula L can be coupled with compounds of formula M under Sonogashira coupling conditions (see: *Synthesis*, 1980 (8) 627-630) and subsequently treated with iodine in an inert solvent such as dichloromethane to undergo direct iodo cyclisation and formation of N (see *Org. Letters* 2004, 6(6)1037-1040).

Compounds of formula M can be prepared from the parent halogenated compound by reaction under Sonogashira conditions (see: *Synthesis,* 1980 (8) 627-630) with trimethylsilyl acetylene, followed by deprotection under basic conditions of the trimethyl silyl group. Compounds of formula M may also be prepared from the parent aldehyde under Corey-Fuchs reaction conditions (see *Tet. Lett.* 1972 (36), 3769).

Compounds of formula O may be obtained by treatment of N under the same conditions as the ones described above for K in scheme 2 in the presence of a boronic acid.

Compounds of formula G may be obtained by deprotection of compounds of formula O under state of the art methods depending on the nature of the protective group. As an example, acetate as protective group can be deprotected under acidic conditions such as HCl or basic conditions such as LiOH. It is to be noted that weak protecting groups may be deprotected during the course of reactions to generate compounds of formula N or O. It is also to be not noticed that PG and $R^3$ may be the same from the beginning of the preparation thus the sequence of deprotection is not required.

Compounds of formula H may be obtained following the procedure described above in scheme 1.

Scheme 4 describes an alternative method for the preparation of compound of formula (I) where $R^3$ is $OR^{12}$ as described previously:

Scheme 4

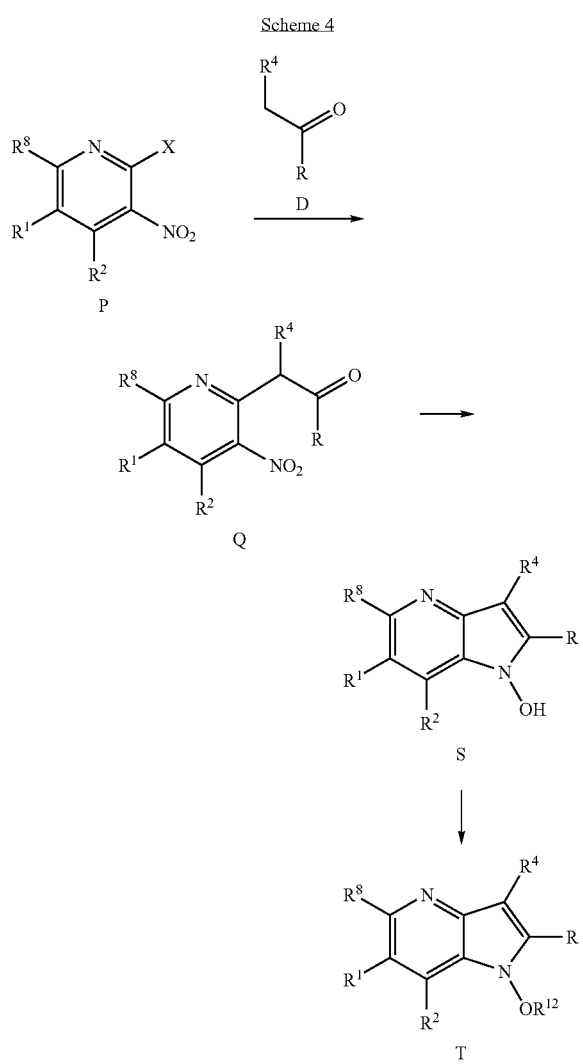

Reaction of a ketone of formula D (as already described) and a 3-nitropyridine of formula P in the presence of a base such as sodium hydride or potassium t-butoxide in an aprotic solvent such as dimethylformamide gives a compound of formula Q that may also exist as its enol form.

Compounds of formula P, where X is a halogen such as chlorine or bromine are either commercially available or might be prepared by known methods. Compounds such as 2-chloro-3-nitro-pyridine, 2-bromo-3-chloropyridine, 2-chloro-4-methyl-3-nitropyridine, 2-chloro-5-methyl-3-nitropyridine are commercially available. For the preparation of compounds of formula P, the person skilled in the art might like to follow example such as preparation of 2,5-dibromo-3-nitropyridine described in *Tet. Lett.* 59 (43) 8555-8570.

Compounds of formula Q can be selectively reduced at the nitro position under different condition to generate the 1-hydroxy-azaindole of formula S. For example, compounds of formula Q can be treated under Bechamp conditions in the presence of iron in an acidic aqueous media to give compounds of formula S. Under these conditions, the complete reduced form of the azaindole might also be formed. Compounds of formula Q can also be treated under catalytic hydrogenation condition, in the presence of hydrogen, with or without pressure, with a catalyst such as palladium on charcoal in an alcoholic solvent such as ethanol.

Compounds of formula S can then be treated under the same conditions as the ones disclosed for G in scheme 1 in order to generate compound of formula T where $R^{12}$ is as previously described.

Scheme 5 describes an alternative method for the preparation of compound of formula (I) where $R^6$ is not hydrogen.

Scheme 5

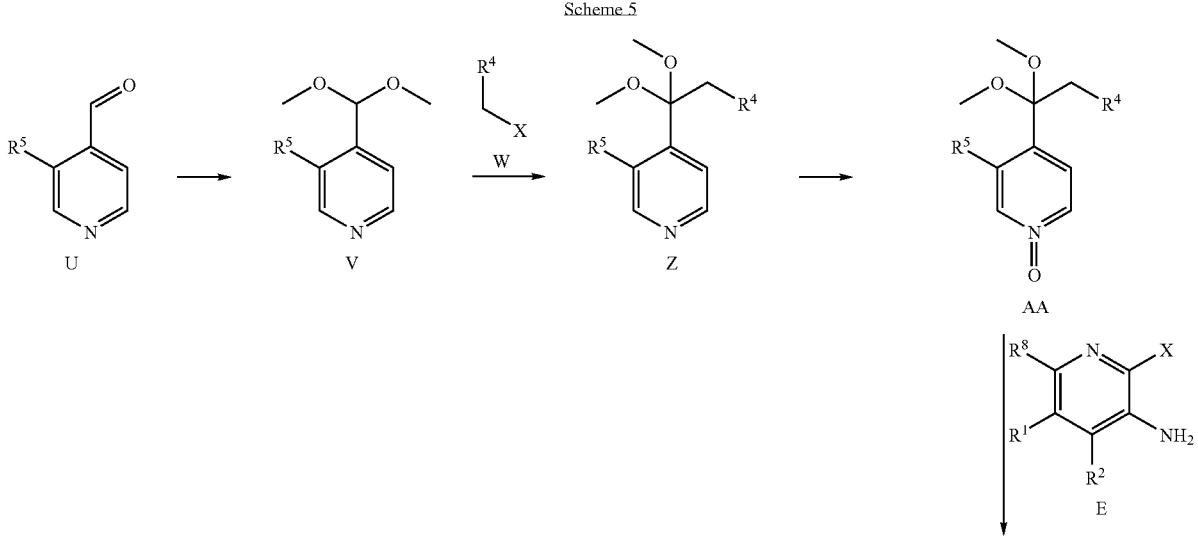

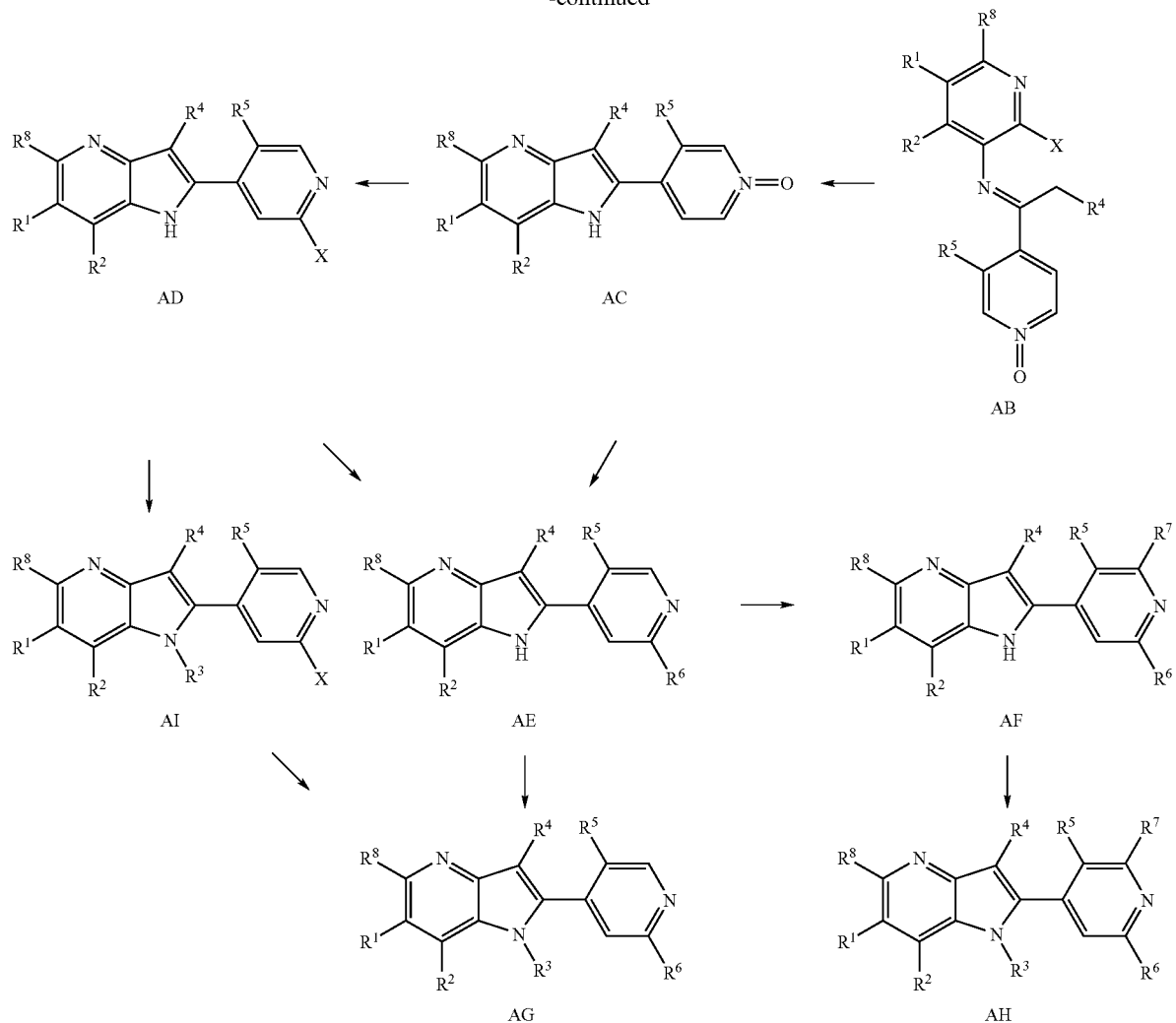

For this sequence, a pyridine of formula U where $R^5$ is as previously described can be transformed in its acetal V by treating the corresponding aldehyde in methanol or in suitable trialkyl ortho formate such as trimethylorthoformate (for the preparation of the dimethylacetal) in the presence of a catalytic amount of an acid such as sulfuric acid.

The compound of formula U may be commercially available for example 4-pyridine carboxaldehyde, 3-nitro isonicotinaldehyde and 3-chloro-4-pyridine carboxaldehyde but may also be prepared by state of the art methodology for example starting from the hydroxymethyl derivative by an oxidation procedure (see Aus. J. Chem 1993, 46(7) 987-993) but also by the reduction of the corresponding ester. The compound of formula U may also be prepared from the halogen or unsubstituted analogue by halogen-metal or hydrogen-metal exchange followed by treatment with a suitable electrophile such as dimethylformamide (see Synthesis 1999, 306-311).

Compounds of formula Z can be obtained by treating compounds of formula V with a suitable base such a n-butyl lithium, sodium hydride or lithium hexamethyldisilazane in an aprotic solvent such a tetrahydrofuran or diethyl ether preferably at low temperature followed by the treatment of the anion by a compound of formula W where X is a leaving group such as halogen (chlorine, bromine or iodide) or a mesylate and $R^4$ is as previously described.

Compounds of formula W are usually commercially available for example 4-fluorobenzyl chloride, 3-methyl benzyl chloride or benzyl bromide but may also be prepared by state of the art methodologies.

Compounds of formula Z can be oxidized to generate compounds of formula AA, for example in the presence of hydrogen peroxide in a solvent such as dichloromethane in the presence of a catalyst such as methyl trioxorhenium (see Tet. Lett. 1996, 37(6), 805-808) or in the presence of hydrogen peroxide-urea complex in a solvent such as dichloromethane (see Chem. Ber. 1992, 125(8), 1965-1966).

Compounds of formula AA can be treated by the previously described 3-amino pyridine of formula E under the conditions described for the preparation of F in scheme 1 to generate compound of formula AB. Alternatively AB can be obtained by reacting AA and E together in the absence of solvent at a temperature allowing the distillation of the alcohol formed (see Synthesis 1993, 12, 1227-1229).

As previously mentioned, compounds of formula AB can exists under its two isomers imine and enamine that may also be separated for example by chromatography.

Cyclisation of AB under the conditions described in scheme 1 for the formation of G allows the preparation of the azaindole AC.

Compounds of formula AD where X is halogen such as chlorine or bromine can be prepared by treating AC with $POCl_3$ or $POBr_3$ under conditions used in state of the art methodology such as chlorination of substituted pyridines in *Chem. and Pharm. Bull.* 1994, 42(9), 1841-1849.

Compounds of formula AE can be prepared from AD by Buchwald amination or amidation reaction in the presence a primary amide or amine, of a palladium (II) catalyst such as palladium diacetate, a ligand such as Xantphos®, a base such as potassium or cesium carbonate in an aprotic solvent such as dioxane or tetrahydrofuran under thermal or microwave conditions (see *Org. Let.* 2001, 3(21) 3417-3419).

Compounds of formula AE may also be prepared from AD by direct treatment with an amine such as benzyl amine under thermal or microwave conditions, followed by treatment with a strong acid such as concentrated sulphuric acid to generate the compound where $R^6$ is $NH_2$. Such an intermediate can be further treated by an appropriate non nucleophilic base such as pyridine in a solvent such as dimethylformamide or tetrahydrofuran and an acylating agent such as $R^{20}COX$ where X is chlorine or fluorine and $R^{20}$ is as previously described. It can also be treated with an alkylating agent, such as $R^{18}$—X where X is a leaving group such as halogen or a mesylate, under the same conditions. Another alkylation or acylation will provide, under the same conditions, compounds where $R^6$ is $NR^{18}R^{19}$, as previously described.

Compounds of formula AE where $R^6$ is neither an amine nor an amide can be prepared directly by treating compounds of formula AC with an activating agent followed by a nucleophile as described in the review from *Science of Synthesis* (2005), 15, 285-387 (Georg Thiem Verlag Publisher). For example, if $R^6$ is cyanide, compounds of formula AC are treated with an activator such as benzoyl chloride in the presence of a cyanide source such as trimethylsilyl-cyanide in an aprotic solvent such as dimethylformamide or tetrahydrofuran (See *J. Org. Chem.* 1983, 48, 1375-1377).

Compounds of formula AE where $R^6$ is cyanide can be further modified by state of the art methods to generate all the possible derivatives of the cyanide group: for example, reduction to the acid or ester, reduction to the amide or reduction to the amine, addition on cyanide by an alkyl or aryl Grignard to generate the ketone.

Compounds of formula AI can be prepared from AD following the methodology described in scheme 1 for the preparation of H from G.

Compounds of formula AG can be prepared from AE following the methodology used for the preparation of AI. Compounds of formula AG can also be prepared from AI following the methodologies used for the preparation of AE from AD.

Compounds of formula AF can be prepared from AE by the following treatment:
- oxidation of the pyridine following the preparation described for AA from Z direct reaction to introduce $R^7$ as described for the introduction of $R^6$ in the preparation of AE from AD
- $R^7$ may also be introduced by the methodologies described for the introduction of $R^6$ in the preparation of AE from AC via AD.

Compounds of formula AH may be prepared from compound of formula AF following the treatment described for the preparation of H in scheme 1.

Further steps may be realized that are not disclosed in the scheme 5 from compound AC, AD, AI, AE, AF, AG and AI1. These reactions may result in further transformation of $R^1$ to $R^8$, for example, cyclisation between $R^6$ and $R^3$ or between $R^1$ and $R^2$.

Scheme 6 describes an alternative method for the preparation of compounds of formula (I) where $X^1$ is CH and $X^2$ is N (compounds of formula (Ic), for example, those compounds listed in Table 3).

Scheme 6

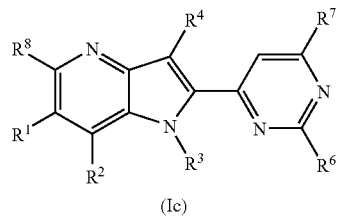

(Ic)

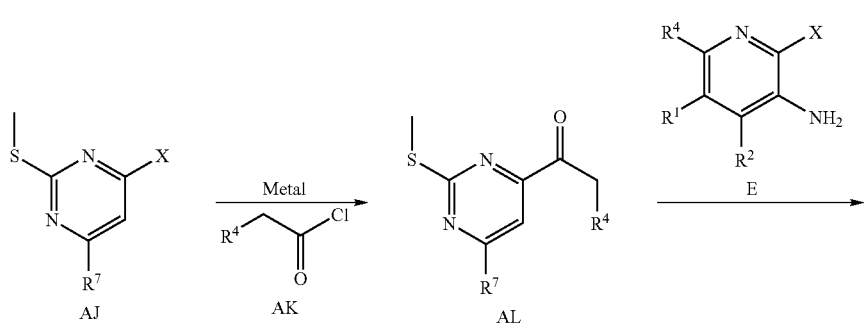

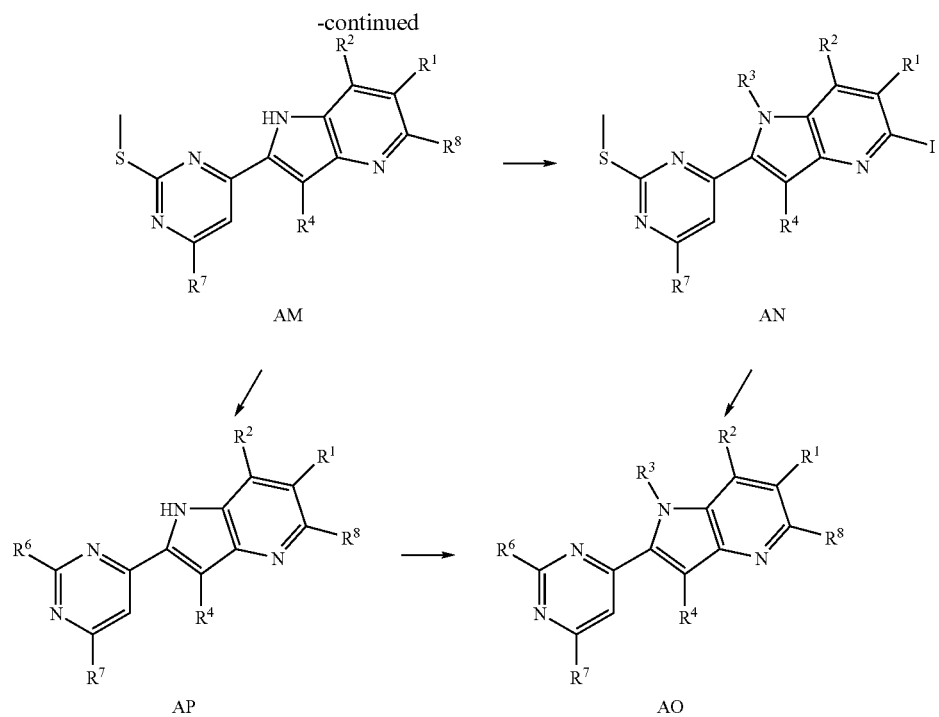

Compounds of formula AL can be prepared by treatment of pyrimidine of formula AJ where X is a halogen such as bromine, chlorine or iodide and $R^7$ as previously described in the presence of a suitable base to realize the metal halogen exchange. n-butyl lithium, s-butyl lithium may be used in an aprotic solvent such as tetrahydrofuran preferably at low temperature. The acyl chloride of formula AK can then react with the previously formed anion of the pyrimidine to give compounds of formula AL.

Compounds of formula AJ may be commercially available such as the 4-iodo-2-methylthio-pyrimidine or obtained by state of the art methods (see for examples Tet. Lett. 2001, 42(2), 311-313).

Compounds of formula AK are usually commercially available, for example phenylacetyl chloride, m-tosylacetyl chloride or 4-fluoro benzeneacetyl chloride but might also be prepared from the corresponding acid.

Compounds of formula AM can be prepared from the condensation between compounds of formula E and AL under the conditions described for the formation of compound F in scheme 1, followed by the cyclisation of the imine or enamine obtained under the conditions described in scheme 1 for the formation of compound G.

Compound E is as previously described.

The oxidation of the pyrimidine of compounds of formula AM in the presence of an oxidant such as m-chloroperbenzoique acid in a solvent such as dichloromethane results in the formation of the sulfoxide intermediate. Further treatment of this intermediate with an amine such as benzyl amine followed by treatment in concentrated sulphuric acid results in the formation of a compound of formula AP where $R^6$ is $NH_2$. Further treatment as previously described for the formation of compound AE in scheme 5 results in the formation of AP with $R^6$ as previously described.

Compounds of formula AN may be obtained by treatment of compounds of formula AM following the same procedure as the one previously described for the formation of compounds of formula H from compound of formula G.

Compounds of formula AO can be prepared from compounds of formula AN as previously described for the preparation of compounds of formula AP from compounds of formula AM.

Compounds of formula AO may also be prepared by the direct introduction of $R^3$ at the indole ring of the compounds of formula AP following the procedure previously described for the formation of compounds of formula H from compounds of formula G in scheme 1.

Scheme 7 describes an alternative method for the preparation of compound of formula (I).

Scheme 7

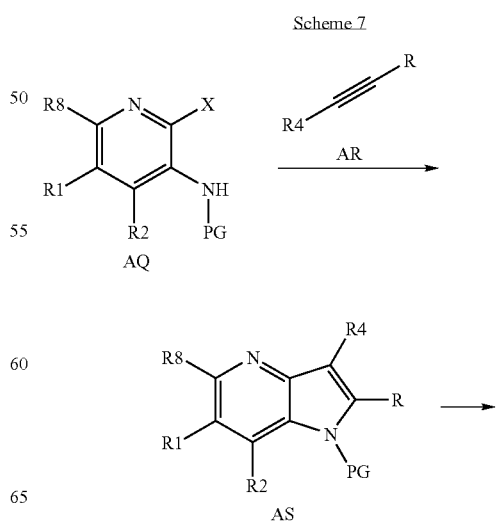

-continued

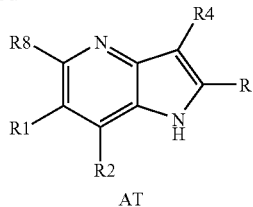

AT

Compounds of formula AQ (where PG is a protective group such as benzyl, acetate, trifluoroacetate) may be obtained by protection of the corresponding aminopyridine E (see "Protective groups in organic chemistry", Greene and Wuts 4$^{th}$ edition, Wiley Interscience). Compounds of formula AQ can then be coupled with compounds of formula AR (where R$^4$ is neither a phenyl nor a 4-fluorophenyl) under palladium-catalyzed indolization conditions (see Org. Letters 2004, 6 (22), 4129-4132) to afford compounds AS. The latter can then be deprotected according to known procedures, for instance benzyl groups can be removed by catalytic hydrogenation.

The previously described processes will enable those skilled in the art to understand the general conditions and techniques to be used in this invention. Further modification of groups R$^1$ to R$^8$ to allow the preparation of compounds disclosed in this invention might be necessary to realize for example the formation of cyclic structure between R$^1$ and R$^2$, R$^1$ and R$^3$, R$^2$ and R$^3$, R$^3$ and R$^5$ and R$^5$ and R$^6$. It will be recognized by those skilled in the art that these modifications might be realized by more than one step, involving for example reduction, oxidation, coupling reaction with or without catalyst, nucleophilic substitution, latonisation, lactamisation and the like.

As indicated above, it has now been found that the compounds of formula I are useful in controlling plant pathogenic fungi when they are applied to a plant or plant propagation material in a fungicidally effective amount.

By 'plant propagation material' is meant generative parts of a plant including seeds of all kinds (fruit, tubers, bulbs, grains etc), roots, rhizomes, cuttings, cut shoots and the like. Plant propagation material may also include plants and young plants which are to be transplanted after germination or after emergence from the soil.

The methods, compounds and compositions of the present invention are, for example, effective against the phytopathogenic fungi of the following classes: Fungi imperfecti (e.g. *Botrytis*, *Pyricularia*, *Helminthosporium*, *Fusarium*, *Septoria*, *Cercospora* and *Alternaria*), Basidiomycetes (e.g. *Rhizoctonia*, *Hemileia*, *Puccinia*), Ascomycetes (e.g. *Venturia* and *Erysiphe*, *Podosphaera*, *Monilinia*, *Uncinula* and *Pyrenophora*) and Oomycetes (e.g. *Phytophthora*, *Pythium*, *Plasmopara*). In particular, the methods, compounds and compositions of the present invention are effective against *Botrytis* spp., *Pyricularia* spp., *Fusarium* spp. *Septoria* spp., *Rhizoctonia* spp., *Puccinia* spp., *Erysiphe* spp., *Phytophthoria* spp., *Pythium* spp. and *Plasmopara* spp. Most particularly, the methods, compounds and compositions of the present invention are effective against *Botrytis cinerea*, *Pyricularia oryzae*, *Fusarium culmorum*, *Septoria nodurum* and *Septoria tritici*, *Rhizoctonia solani*, *Puccinia recondite*, *Erysiphe graminis*, *Pyrenophora teres*, *Phytophthora infestans*, *Pythium ultimum* and *Plasmopara viticola*.

The methods, compounds and compositions of the present invention are suitable for controlling such disease on a number of plants and their propagation material including, but not limited to the following target crops: cereals (wheat, barley, rye, oats, maize (including field corn, pop corn and sweet corn), rice, sorghum and related crops); beet (sugar beet and fodder beet); leguminous plants (beans, lentils, peas, soybeans); oil plants (rape, mustard, sunflowers); cucumber plants (marrows, cucumbers, melons); fibre plants (cotton, flax, hemp, jute); vegetables (spinach, lettuce, asparagus, cabbages, carrots, eggplants, onions, pepper, tomatoes, potatoes, paprika, okra); plantation crops (bananas, fruit trees, rubber trees, tree nurseries), ornamentals (flowers, shrubs, broad-leaved trees and evergreens, such as conifers); as well as other plants such as vines, bushberries (such as blueberries), caneberries, cranberries, peppermint, rhubarb, spearmint, sugar cane and turf grasses including, but not limited to, cool-season turf grasses (for example, bluegrasses (*Poa* L.), such as Kentucky bluegrass (*Poa pratensis* L.), rough bluegrass (*Poa trivialis* L.), Canada bluegrass (*Poa compressa* L.) and annual bluegrass (*Poa annua* L.); bentgrasses (*Agrostis* L.), such as creeping bentgrass (*Agrostis palustris* Huds.), colonial bentgrass (*Agrostis tenius* Sibth.), velvet bentgrass (*Agrostis canina* L.) and redtop (*Agrostis alba* L.); fescues (*Festuca* L.), such as tall fescue (*Festuca arundinacea* Schreb.), meadow fescue (*Festuca elatior* L.) and fine fescues such as creeping red fescue (*Festuca rubra* L.), chewings fescue (*Festuca rubra* var. *commutata* Gaud.), sheep fescue (*Festuca ovina* L.) and hard fescue (*Festuca longifolia*); and ryegrasses (*Lolium* L.), such as perennial ryegrass (*Lolium perenne* L.) and annual (Italian) ryegrass (*Lolium multiflorum* Lam.)) and warm-season turf grasses (for example, Bermudagrasses (*Cynodon* L. C. Rich), including hybrid and common Bermudagrass; Zoysiagrasses (*Zoysia Willd.*), St. Augustinegrass (*Stenotaphrum secundatum* (Walt.) Kuntze); and centipedegrass (*Eremochloa ophiuroides* (Munro.) Hack.)).

In addition 'crops' are to be understood to include those crops that have been made tolerant to pests and pesticides, including herbicides or classes of herbicides, as a result of conventional methods of breeding or genetic engineering. Tolerance to e.g. herbicides means a reduced susceptibility to damage caused by a particular herbicide compared to conventional crop breeds. Crops can be modified or bred so as to be tolerant, for example, to HPPD inhibitors such as mesotrione or EPSPS inhibitors such as glyphosate.

Furthermore, the compounds of formula I find general use as fungicides and may therefore also be used to control pathogenic fungi in related areas, for example in the protection of technical materials, including wood and wood related technical products, in food storage or in hygiene management. As such, the present invention further provides the use of a compound of formula I for controlling fungi.

When used in the methods of the invention, the compounds of formula I may be in unmodified form or, preferably, formulated together with carriers and adjuvants conventionally employed in the art of formulation.

The invention therefore also relates to a composition for the control of fungal infection comprising a compound of formula I as defined above and an agriculturally acceptable carrier or diluent.

The agrochemical composition will usually contain from 0.1 to 99% by weight, preferably from 0.1 to 95% by weight, of the compound of formula I, 99.9 to 1% by weight, preferably 99.8 to 5% by weight, of a solid or liquid adjuvant, and from 0 to 25% by weight, preferably from 0.1 to 25% by weight, of a surfactant.

Suitably, the agrochemical compositions and formulations of the present invention are applied prior to disease development. Rates and frequency of use of the formulations are those conventionally used in the art and will depend on the risk of infestation by the fungal pathogen, the developmental stage of the plant and on the location, timing and application method. Advantageous rates of application are normally from 5 g to 2 kg of active ingredient (a.i.) per hectare (ha), preferably from 10 g to 1 kg a.i./ha, most preferably from 20 g to 600 g a.i./ha. When used as seed drenching agent, convenient rates of application are from 10 mg to 1 g of active substance per kg of seeds.

In practice, as indicated above, the agrochemical compositions comprising compound of formula (I) are applied as a formulation containing the various adjuvants and carriers known to or used in the industry. They may thus be formulated as granules, as wettable or soluble powders, as emulsifiable concentrates, as coatable pastes, as dusts, as flowables, as solutions, as suspensions or emulsions, or as controlled release forms such as microcapsules. These formulations are described in more detail below and may contain as little as about 0.5% to as much as about 95% or more by weight of the active ingredient. The optimum amount will depend on formulation, application equipment and nature of the plant pathogenic fungi to be controlled.

Suspension concentrates are aqueous formulations in which finely divided solid particles of the active compound are suspended. Such formulations include anti-settling agents and dispersing agents and may further include a wetting agent to enhance activity as well an anti-foam and a crystal growth inhibitor. In use, these concentrates are diluted in water and normally applied as a spray to the area to be treated. The amount of active ingredient may range from about 0.5% to about 95% of the concentrate.

Wettable powders are in the form of finely divided particles which disperse readily in water or other liquid carriers. The particles contain the active ingredient retained in a solid matrix. Typical solid matrices include fuller's earth, kaolin clays, silicas and other readily wet organic or inorganic solids. Wettable powders normally contain about 5% to about 95% of the active ingredient plus a small amount of wetting, dispersing or emulsifying agent.

Emulsifiable concentrates are homogeneous liquid compositions dispersible in water or other liquid and may consist entirely of the active compound with a liquid or solid emulsifying agent, or may also contain a liquid carrier, such as xylene, heavy aromatic naphthas, isophorone and other non-volatile organic solvents. In use, these concentrates are dispersed in water or other liquid and normally applied as a spray to the area to be treated. The amount of active ingredient may range from about 0.5% to about 95% of the concentrate.

Granular formulations include both extrudates and relatively coarse particles and are usually applied without dilution to the area in which control of plant pathogenic fungi is required. Typical carriers for granular formulations include sand, fuller's earth, attapulgite clay, bentonite clays, montmorillonite clay, vermiculite, perlite, calcium carbonate, brick, pumice, pyrophyllite, kaolin, dolomite, plaster, wood flour, ground corn cobs, ground peanut hulls, sugars, sodium chloride, sodium sulphate, sodium silicate, sodium borate, magnesia, mica, iron oxide, zinc oxide, titanium oxide, antimony oxide, cryolite, gypsum, diatomaceous earth, calcium sulphate and other organic or inorganic materials which absorb or which can be coated with the active compound. Granular formulations normally contain about 5% to about 25% active ingredients which may include surface-active agents such as heavy aromatic naphthas, kerosene and other petroleum fractions, or vegetable oils; and/or stickers such as dextrins, glue or synthetic resins.

Dusts are free-flowing admixtures of the active ingredient with finely divided solids such as talc, clays, flours and other organic and inorganic solids which act as dispersants and carriers.

Microcapsules are typically droplets or granules of the active ingredient enclosed in an inert porous shell which allows escape of the enclosed material to the surroundings at controlled rates. Encapsulated droplets are typically about 1 to 50 microns in diameter. The enclosed liquid typically constitutes about 50 to 95% of the weight of the capsule and may include solvent in addition to the active compound. Encapsulated granules are generally porous granules with porous membranes sealing the granule pore openings, retaining the active species in liquid form inside the granule pores. Granules typically range from 1 millimetre to 1 centimetre and preferably 1 to 2 millimetres in diameter. Granules are formed by extrusion, agglomeration or prilling, or are naturally occurring. Examples of such materials are vermiculite, sintered clay, kaolin, attapulgite clay, sawdust and granular carbon. Shell or membrane materials include natural and synthetic rubbers, cellulosic materials, styrene-butadiene copolymers, polyacrylonitriles, polyacrylates, polyesters, polyamides, polyureas, polyurethanes and starch xanthates.

Other useful formulations for agrochemical applications include simple solutions of the active ingredient in a solvent in which it is completely soluble at the desired concentration, such as acetone, alkylated naphthalenes, xylene and other organic solvents. Pressurised sprayers, wherein the active ingredient is dispersed in finely-divided form as a result of vaporization of a low boiling dispersant solvent carrier, may also be used.

Suitable agricultural adjuvants and carriers that are useful in formulating the compositions of the invention in the formulation types described above are well known to those skilled in the art. Suitable examples of the different classes are found in the non-limiting list below.

Liquid carriers that can be employed include water, toluene, xylene, petroleum naphtha, crop oil, acetone, methyl ethyl ketone, cyclohexanone, acetic anhydride, acetonitrile, acetophenone, amyl acetate, 2-butanone, chlorobenzene, cyclohexane, cyclohexanol, alkyl acetates, diacetonalcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethyl formamide, dimethyl sulfoxide, 1,4-dioxane, dipropylene glycol, dipropylene glycol methyl ether, dipropylene glycol dibenzoate, diproxitol, alkyl pyrrolidinone, ethyl acetate, 2-ethyl hexanol, ethylene carbonate, 1,1,1-trichloroethane, 2-heptanone, alpha pinene, d-limonene, ethylene glycol, ethylene glycol butyl ether, ethylene glycol methyl ether, gamma-butyrolactone, glycerol, glycerol diacetate, glycerol monoacetate, glycerol triacetate, hexadecane, hexylene glycol, isoamyl acetate, isobornyl acetate, isooctane, isophorone, isopropyl benzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octadecanoic acid, octyl amine acetate, oleic acid, oleylamine, o-xylene, phenol, polyethylene glycol (PEG400), propionic acid, propylene glycol, propylene glycol monomethyl ether, p-xylene, toluene, triethyl phosphate, triethylene glycol, xylene sulfonic acid, paraffin, mineral oil, trichloroethylene, perchloroethylene, ethyl acetate, amyl acetate, butyl acetate, methanol, ethanol, isopropanol, and higher molecular weight alcohols such as amyl alcohol, tetrahydrofurfuryl alcohol, hexanol, octanol, etc. ethylene glycol, propylene glycol, glycerine, N-methyl-2-pyrrolidinone, and the like. Water is generally the carrier of choice for the dilution of concentrates.

Suitable solid carriers include talc, titanium dioxide, pyrophyllite clay, silica, attapulgite clay, kieselguhr, chalk, diatomaxeous earth, lime, calcium carbonate, bentonite clay, fuller's earth, cotton seed hulls, wheat flour, soybean flour, pumice, wood flour, walnut shell flour, lignin and the like.

A broad range of surface-active agents are advantageously employed in both said liquid and solid compositions, especially those designed to be diluted with carrier before application. These agents, when used, normally comprise from 0.1% to 15% by weight of the formulation. They can be anionic, cationic, non-ionic or polymeric in character and can be employed as emulsifying agents, wetting agents, suspending agents or for other purposes. Typical surface active agents include salts of alkyl sulfates, such as diethanolammonium lauryl sulphate; alkylarylsulfonate salts, such as calcium dodecylbenzenesulfonate; alkylphenol-alkylene oxide addition products, such as nonylphenol-C.sub. 18 ethoxylate; alcohol-alkylene oxide addition products, such as tridecyl alcohol-C.sub. 16 ethoxylate; soaps, such as sodium stearate; alkylnaphthalenesulfonate salts, such as sodium dibutylnaphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; and salts of mono and dialkyl phosphate esters.

Other adjuvants commonly utilized in agricultural compositions include crystallisation inhibitors, viscosity modifiers, suspending agents, spray droplet modifiers, pigments, antioxidants, foaming agents, anti-foaming agents, light-blocking agents, compatibilizing agents, antifoam agents, sequestering agents, neutralising agents and buffers, corrosion inhibitors, dyes, odorants, spreading agents, penetration aids, micronutrients, emollients, lubricants, sticking agents, and the like.

In addition, further, other biocidally active ingredients or compositions may be used in the methods of the invention and applied simultaneously or sequentially with the compound of formula (I). When applied simultaneously, these further active ingredients may be formulated together with the compound of the invention or mixed in, for example, the spray tank. These further biocidally active ingredients may be fungicides, herbicides, insecticides, bactericides, acaricides, nematicides and/or plant growth regulators.

Examples of insecticidal compounds for use in the compositions/methods of the present invention include, but are not limited to, pyrethroids (such as permethrin, cypermethrin, fenvalerate, esfenvalerate, deltamethrin, cyhalothrin (in particular, lambda-cyhalothrin), bifenthrin, fenpropathrin, cyfluthrin, tefluthrin, fish safe pyrethroids (for example ethofenprox), natural pyrethrin, tetramethrin, s-bioallethrin, fenfluthrin, prallethrin and 5-benzyl-3-furylmethyl-(E)-(1R,3S)-2,2-dimethyl-3-(2-oxothiolan-3-ylidenemethyl)cyclopropane carboxylate), organophosphates (such as, profenofos, sulprofos, acephate, methyl parathion, azinphosmethyl, demeton-s-methyl, heptenophos, thiometon, fenamiphos, monocrotophos, profenofos, triazophos, methamidophos, dimethoate, phosphamidon, malathion, chlorpyrifos, phosalone, terbufos, fensulfothion, fonofos, phorate, phoxim, pirimiphos-methyl, pirimiphos-ethyl, fenitrothion, fosthiazate and diazinon); carbamates, including aryl carbamates, (such as pirimicarb, triazamate, cloethocarb, carbofuran, furathiocarb, ethiofencarb, aldicarb, thiofurox, carbosulfan, bendiocarb, fenobucarb, propoxur, methomyl and oxamyl), benzoyl ureas (such as diflubenzuron, triflumuron, hexaflumuron, flufenoxuron and chlorfluazuron), organic tin compounds (such as cyhexatin, fenbutatin oxide and azocyclotin), pyrazoles (such as tebufenpyrad and fenpyroximate), macrolides (such as avermectins or milbemycins, for example abamectin, emamectin benzoate, ivermectin, milbemycin, spinosad and azadirachtin), hormones or pheromones, organochlorine compounds (such as endosulfan, benzene hexachloride, DDT, chlordane and dieldrin), amidines (such as chlordimeform and amitraz), fumigant agents (such as chloropicrin, dichloropropane, methyl bromide and metam); chloronicotinyl compounds (such as imidacloprid, thiacloprid, acetamiprid, nitenpyram and thiamethoxam), diacylhydrazines (such as tebufenozide, chromafenozide and methoxyfenozide), diphenyl ethers (such as diofenolan and pyriproxifen), indoxacarb, chlorfenapyr and pymetrozine.

Examples of herbicidal compounds for use in the compositions/methods of the present invention include, but are not limited to, 2,3,6-TBA, 2,4-D, 2,4-DB, acetochlor, acifluorfen-sodium, aclonifen, acrolein, alachlor, alloxydim, ametryn, amicarbazone, amidosulfuron, aminopyralid, aminotriazol, amitrole, ammonium sulfamate, anilofos, asulam, atrazine, aviglycine, azafenidin, azimsulfuron, BAY FOE 5043, beflubutamid, benazolin, bencarbazone, benfluralin, benfuresate, bensulfuron-methyl, bensulide, bentazone, benzfendizone, benzobicyclon, benzofenap, bialaphos, bifenox, bispyribac-sodium, borax, bromacil, bromobutide, bromophenoxim, bromoxynil, butachlor, butafenacil, butamifos, butralin, butroxydim, butylate, cafenstrole, carbetamide, carfentrazone-ethyl, chloransulam methyl, chlorbromuron, chlorflurenol-methyl, chloridazon, chlorimuron-ethyl, chloroacetic acid, chlorotoluron, chlorpropham, chlorsulfuron, chlorthal-dimethyl, cinidon-ethyl, cinmethylin, cinosulfuron, clefoxydim profoxidim, clethodim, clodinafop-propargyl, clomazone, clomeprop, clopyralid, cloransulam, cloransulam-methyl, cumuluron, cumyluron, cyanamide, cyanazine, cyclanilide, cycloate, cyclosulfamuron, cycloxydim, cyhalofop, cyhalofop-butyl, cyprosulfamide, daimuron, dalapon, dazomet, desmedipham, desmetryn, dicamba, dichlobenil, dichlorprop, dichlorprop-P, diclofop-methyl, diclosulam, difenzoquat metilsulfate, diflufenican, diflufenzopyr, dimefuron, dimepiperate, dimethachlor, dimethametryn, dimethenamid, dimethenamid-P, dimethipin, dimethylarsinic acid, dinitramine, dinoterb, diphenamid, dipropetryn, diquat, ibromide, dithiopyr, diuron, DNOC, DSMA, endothal, EPTC, esprocarb, ethalfluralin, ethametsulfuron-methyl, ethephon, ethofumesate, ethoxyfen-ethyl, ethoxysulfuron, etobenzanid, fenclorim, fenoxaprop-P-ethyl, fentrazamide, ferrous sulfate, flamprop, flamprop-M, flazasulfuron, florasulam, fluazifop-butyl, fluazifop-P-butyl, fluazolate, flucarbazone sodium, flucetosulfuron, fluchloralin, flufenacet, flufenpyr-thyl, flumetralin, flumetsulam, flumiclorac-pentyl, flumioxazin, flumipropin, fluometuron, fluoroglycofenethyl, fluoxaprop, flupoxam, flupropacil, flupropanate, flupyrsulfuron-methyl-sodium, flurenol, fluridone, fluorochloridone, fluoroxypyr, flurtamone, fluthiacet-methyl, fluxofenim, fomesafen, foramsulfuron, fosamine, glufosinate-ammonium, glyphosate, halosulfuron-methyl, haloxyfop, haloxyfop-P, HC-252, hexazinone, imazamethabenz-methyl, imazamox, imazapic, imazapyr, imazaquin, imazethapyr, imazosulfuron, indanofan, iodosulfuron, iodosulfuron-methyl-sodium, ioxynil, isopropazol, isoproturon, isouron, isoxaben, isoxachlortole, isoxadifen, isoxaflutole, isoxapyrifop, karbutylate, KIH-485, lactofen, lenacil, linuron, MCPA, MCPA-thioethyl, MCPB, mecoprop, mecoprop-P, mefenacet, mefenpyr diethyl, mefluidide, mesosulfuron methyl, mesotrione, metam, metamifop (mefluoxafop), metamitron, metazachlor, methabenzthiazuron, methazole, methyl isothiocyanate, methylarsonic acid, methyldymron, metobenzuron, metobromuron, metolachlor, metosulam, metoxuron, metribuzin, metsulfuron-methyl, MK-616, molinate, monolinuron, MSMA, naproanilide, napropamide, naptalam, NDA-402989, neburon, nefenacet, nicosulfuron, nipyraclofen, n-methyl-glyphosate, nonanoic acid, norflurazon, oleic acid (fatty acids), orbencarb, orthosulfamuron, oryzalin, oxaciclomefone, oxadiargyl, oxadiazon, oxasulfuron, oxaziclomefone, oxyfluorfen, pebulate, pendimethalin, penoxsulam, pentachlorophenol, pentanochlor, pentoxazone, pethoxamid, petrolium oils, phenmedipham, phenoxaprop-P-ethyl (R), picloram, picolinafen, pinoxaden, piperophos, pretilachlor, primisulfuron, primisulfuron-methyl, procarbazone, prodiamine, profluazol, profoxydim, prohexcadion calcium, prometon, prometryn, propachlor, propanil, propaquizafop, propazine, propham, propisochlor, propoxycarbazone, propoxycarbazone-sodium, propyzamide, prosulfocarb, prosulfuron, pyraclonil pyrazogyl, pyraflufen-ethyl, pyrasulfotole, pyrazolynate, pyrazosulfuron-ethyl, pyrazoxyfen, pyribenzoxim, pyributicarb, pyridafol, pyridate, pyriftalid, pyriminobac-methyl, pyrimisulfan, pyrithiobac-sodium, quinclorac, quinmerac, quinoclamine, quizalofop, quizalofop-P, rimsulfuron, sequestren, sethoxydim, siduron, simazine, simetryn, S-metolachlor, sodium chlorate, sulcotrione, sulfentrazone, sulfometuron-methyl, sulfosate, sulfosulfuron, sulfuric acid, tar oils, TCA-sodium, tebutam, tebuthiuron, tefuryltrione, tembotrione, tepraloxydim, terbacil, terbumeton, terbuthylazine, terbutryn, thenylchlor, thiazafluoron, thiazimin, thiazopyr, thiencarbazone, thifensulfuron-methyl (thiameturon-methyl), thiobencarb, tiocarbazil, topramezone, tralkoxydim, tri-allate, triasulfuron, triaziflam, tribenuron-methyl, triclopyr, trietazine, triflosulam, trifloxysulfuron, trifloxysulfuron-sodium, trifluralin, triflusulfuron-methyl, trinexapac-ethyl and tritosulfuron.

Examples of fungicidal compounds for use in the compositions/methods of the present invention include, but are not limited to, acibenzolar (CGA245704), ancymidol, alanycarb, aldimorph, amisulbrom anilazine, azaconazole, azoxystrobin, benalaxyl, benthiavalicarb, benomyl, biloxazol, bitertanol, bixafen blasticidin S, boscalid, bromuconazole, bupirimate, captafol, captan, carbendazim, carbendazim chlorhydrate, carboxin, carpropamid, carvone, CGA41396, CGA41397, chinomethionate, chloroneb, chlorothalonil, chlorozolinate, clozylacon, copper containing compounds such as copper oxychloride, copper oxyquinolate, copper sulphate, copper tallate and Bordeaux mixture, cyflufenamid, cymoxanil, cyproconazole, cyprodinil, debacarb, di-2-pyridyl disulphide 1,1'-dioxide, dichlofluanid, diclomezine, dichlozoline, dichlone, dicloran, diclocymet, diethofencarb, difenoconazole, difenzoquat, diflumetorim, O,O-di-iso-propyl-5-benzyl thiophosphate, dimefluazole, dimetconazole, dimethomorph, dimethirimol, dimoxystrobin, diniconazole, dinocap, dithianon, dodecyl dimethyl ammonium chloride, dodemorph, dodine, doguadine, edifenphos, enestrobin, epoxiconazole, ethaboxam, ethirimol, etridiazole, famoxadone, fenamidone (RPA407213), fenarimol, fenbuconazole, fenfuram, fenhexamid (KBR2738), fenoxanil, fenpiclonil, fenpropidin, fenpropimorph, fentin acetate, fentin hydroxide, ferbam, ferimzone, fluazinam, fluopicolide, fludioxonil, fluoxastrobin, flumetover, SYP-LI90 (flumorph), fluopyram fluoroimide, fluquinconazole, flusilazole, flusulfamide, flutolanil, flutriafol, folpet, fosetyl-aluminium, fuberidazole, furalaxyl, furametpyr, guazatine, hexaconazole, hydroxy-isoxazole, hymexazole, IKF-916 (Cyazofamid), imazalil, imibenconazole, iminoctadine, iminoctadine triacetate, ipconazole, iprobenfos, iprodione, iprovalicarb (SZX0722), isopropanyl butyl carbamate, isoprothiolane, kasugamycin, kresoxim-methyl, LY186054, LY211795, LY248908, maneb, mancopper, mancozeb, mandipropamid, maneb, mefenoxam, mepanipyrim, mepronil, metalaxyl, metconazole, methasulfocarb, metiram, metiram-zinc, metominostrobin, metrafenone, myclobutanil, myclozoline, neoasozin, nickel dimethyldithiocarbamate, nitrothal-isopropyl, nuarimol, ofurace, organomercury compounds, orysastrobin, oxadixyl, oxasulfuron, oxine-copper, oxolinic acid, oxpoconazole, oxycarboxin, pefurazoate, penconazole, pencycuron, penthiopyrad, phenazin oxide, phosdiphen, phosphorus acids, phthalide, picoxystrobin (ZA1963), polyoxin D, polyram, probenazole, prochloraz, procymidone, propamocarb, prop-iconazole, propineb, propionic acid, proquinazid, prothioconazole, pyraclostrobin, pyrazophos, Pyribencarb pyrifenox, pyrimethanil, pyroquilon, pyroxyfur, pyrrolnitrin, quaternary ammonium compounds, quinomethionate, quinoxyfen, quintozene, silthiofam simeconazole, sipconazole (F-155), sodium pentachlorophenate, spiroxamine, streptomycin, sulphur, schwefel, tebuconazole, tecloftalam, tecnazene, tetraconazole, thiabendazole, thifluzamid, 2-(thiocyanomethylthio)benzothiazole, thiophanate-methyl, thiram, tiadinil timibenconazole, tolclofos-methyl, tolylfluanid, triadimefon, triadimenol, triazbutil, triazoxide, tricyclazole, tridemorph, trifloxystrobin (CGA279202), triforine, triflumizole, triticonazole, validamycin A, vapam, valiphenal vinclozolin, zineb, ziram, zoxamide, 3-[5-(4-chlorophenyl)-2,3-dimethylisoxazolidin-3-yl]pyridine, 5-chloro-7-(4-methylpiperidine-1-yl)-6-(2,4,6-trifluorophenyl)[1,2,4]triazolo[1,5-a]pyrimidine and N-(4-chloro-2-nitrophenyl)-N-ethyl-4-methyl-benzsulfonamide.

These formulations of the invention and for use in the methods of the invention can be applied to the areas where control is desired by conventional methods such as spraying atomising, dusting, scattering, coating or pouring. Dust and liquid compositions, for example, can be applied by the use of power-dusters, broom and hand sprayers and spray dusters. The formulations can also be applied from airplanes as a dust or a spray or by rope wick applications. Both solid and liquid formulations may also be applied to the soil in the locus of the plant to be treated allowing the active ingredient to penetrate the plant through the roots. The formulations of the invention may also be used for dressing applications on plant propagation material to provide protection against fungus infections on the plant propagation material as well as against phytopathogenic fungi occurring in the soil. Suitably, the active ingredient may be applied to plant propagation material to be protected by impregnating the plant propagation material, in particular, seeds, either with a liquid formulation of the fungicide or coating it with a solid formulation. In special cases, other types of application are also possible, for example, the specific treatment of plant cuttings or twigs serving propagation.

In addition, the compounds of formula (I) as defined above can be used in the treatment of fungal infections of human and animal subjects. The active compounds as described herein may be combined with a pharmaceutically acceptable carrier and administered or applied to such subjects or infections in an amount effective to treat the infection in accordance with known techniques. Accordingly, therefore, the present invention also provides the use of a compound of formula (I) as defined above in the manufacture of a medicament for the treatment of fungal infection in humans or animals.

The present invention will now be described by way of the following non-limiting examples. Those skilled in the art will promptly recognize appropriate variations from the procedures both as to reactants and as to reaction conditions and techniques

EXAMPLES

Example 1

Preparation of 3-(4-Fluoro-phenyl)-6-methyl-2-pyridin-4-yl-1H-pyrrolo[3,2-b]pyridine following procedures described in scheme 1

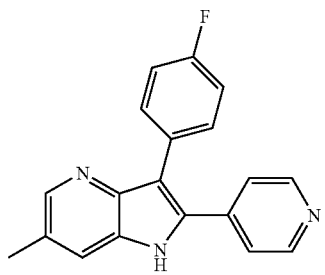

Step 1: 50.6 g of sodium metal (2.1 moles) are dissolved in 1.5 L of absolute ethanol under refluxing conditions. A mixture of 205 g of methyl isonicotinate (1.5 moles) and 202 g of 4-fluorophenyl in 0.5 L of absolute ethanol are added once the temperature has cooled to 30° C. The reaction mixture is refluxed for 4 hours, then cooled and poured into 1.2 L of ice-water. HCl 2N is added to reach pH=3 and the resulting yellow precipitate filtered and dried (271 g). This material is suspended in 1.1 L of 48% HBr solution and heated at 100° C. for 8 hours. Once cooled, the reaction mixture is poured into ice-water (1.2 L) and the pH is adjusted to 7 with a 25% solution of ammonium hydroxide. After extraction in ethyl acetate, the organic layers are dried over magnesium sulfate and the residue after concentration is purified by chromatography on silica gel (ethylacetate/hexane 2/1) to give 133 g of 2-(4-fluorophenyl)-1-(pyridine-4-yl)ethanone as a yellowish solid.

Step 2: A mixture of p-toluenesulfonic acid (500 mg), 2-(4-fluorophenyl)-1-(pyridine-4-yl)ethanone (10 g, 46 mmoles) and 5-methyl-3-amino-2-chloropyridine (8.6 g, 60 mmoles) in 350 mL of toluene was refluxed overnight with a Dean-Stark removal of water/toluene azeotrope. The reaction mixture was further concentrated, the brown residue suspended in an ethyl acetate/hexane mixture (9/1) and filtered. The solid was solubilised in ethyl acetate and purified by chromatography on silica gel (ethylacetate/hexane 1/1) to give 10 g of (2-Chloro-5-methyl-pyridin-3-yl)-[2-(4-fluoro-phenyl)-1-pyridin-4-yl-ethylidene]-amine as a brown solid.

Step 3: 6.15 g (18.1 mmoles) of (2-Chloro-5-methyl-pyridin-3-yl)-[2-(4-fluoro-phenyl)-1-pyridin-4-yl-ethylidene]-amine are dissolved in 100 mL of dimethylformamide under nitrogen. 6.4 g of DABCO (56 mmoles) and 610 mg of bis(triphenylphosphine)palladium dichloride are subsequently added to the reaction mixture which is stirred for 5 hours at 120° C. The cooled reaction mixture is then poured into water and extracted with ethyl acetate. The organic phase is washed with water and dried over magnesium sulfate. The solid residue after concentration is recrystallized into ethyl acetate to afford 5.3 g of 3-(4-Fluoro-phenyl)-6-methyl-2-pyridin-4-yl-1H-pyrrolo[3,2-b]pyridine as a yellowish solid.

Example 2

Preparation of 344-Fluoro-phenyl)-1-methoxymethyl-6-methyl-2-pyridin-4-yl-1H-pyrrolo[3,2-b] pyridine following procedures described in scheme 1

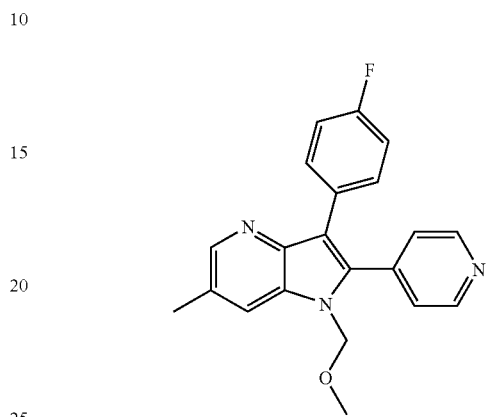

Sodium hydride (22 mg, 0.55 mmole 60% in oil) is added to a solution of 150 mg (0.5 mmole) of 3-(4-Fluoro-phenyl)-6-methyl-2-pyridin-4-yl-1H-pyrrolo[3,2-b]pyridine (prepared as described in example 1) in 5 mL of dimethylformamide at room temperature. After 30 min. at room temperature, a solution of 44.5 mg of chloromethyl methyl ether in 0.5 mL of DMF is added to the reaction mixture. After 45 min. at room temperature, the reaction mixture is poured into ammonium chloride solution and extracted with ethyl acetate. The organic phase is washed with water and dried over magnesium sulfate. The solid residue after concentration is recrystallized into ethyl acetate/hexane mixture (1/2) to afford 70 mg of pure 3-(4-Fluoro-phenyl)-1-methoxymethyl-6-methyl-2-pyridin-4-yl-1H-pyrrolo[3,2-b]pyridine as a yellowish solid.

Example 3

Preparation of 1-Methyl-2-pyridin-4-yl-3-(3-trifluoromethyl-phenyl)-1H-pyrrolo[3,2-b]pyridine following scheme 3

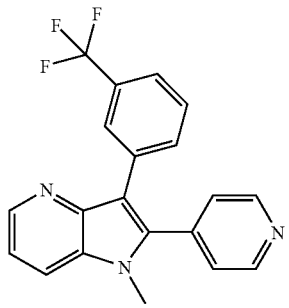

Step 1: 5 g of 3-amino-2-bromopyridine (28.9 mmole) and 15.5 g of formaldehyde in 25 g of formic acid are stirred 6 hours at 100° C. The cooled reaction mixture is poured into water and the pH adjusted to 8-9 by adding sodium hydroxide 2N solution. After extraction in t-butylmethyl ether, the organic layers are washed with water and dried over magnesium sulfate and the residue after concentration is purified by chromatography on silica gel (ethylacetate/hexane 1/1) to give 3.7 g of (2-Bromo-pyridin-3-yl)-dimethyl-amine as orange oil.

Step 2: A mixture of 2 g of (2-Bromo-pyridin-3-yl)-dimethyl-amine (9.95 mmoles), 1.24 g of 4-ethynyl pyridine (12 mmoles) in 120 mL of a 1/1 mixture of triethylamine and dimethylformamide is stirred under argon at room temperature. 750 mg of bis(triphenylphosphine)palladium dichloride and 400 mg of copper iodide are added to the reaction mixture which is further stirred at room temperature for 3 hours. The reaction mixture is poured into ammonium chloride solution and extracted with ethyl acetate. The organic phase is washed with water and dried over magnesium sulfate. The solid residue after concentration is purified by chromatography on silica gel (ethylacetate/hexane 1/1) to give 1 g of Dimethyl-(2-pyridin-4-ylethynyl-pyridin-3-yl)-amine as orange oil.

Step 3: 1 g (4.4 mmoles) of Dimethyl-(2-pyridin-4-ylethynyl-pyridin-3-yl)-amine are dissolved in 60 mL of dichloromethane under argon atmosphere. A solution of 2.27 g of iodine (8.9 mmoles) in 35 mL of dichloromethane is added dropwise in the reaction mixture at 0° C. The reaction mixture is allowed to reach room temperature and further stirred for 4 hours. The reaction mixture is then poured into a solution sodium thiosulfate and extracted with dichloromethane. The organic phase is washed with water and dried over magnesium sulfate. The solid residue after concentration is purified by chromatography on silica gel (ethylacetate) to give 600 mg of 3-Iodo-1-methyl-2-pyridin-4-yl-1H-pyrrolo[3,2-b]pyridine as brown solid.

Step 4: To a solution of 130 mg (0.39 mmoles) of 3-Iodo-1-methyl-2-pyridin-4-yl-1H-pyrrolo[3,2-b]pyridine in 5 mL of toluene under nitrogen is added a 1 mL of a 2N solution of sodium carbonate, 78 mg (0.4 mmole) of 3-trifluoromethyl phenylboronic acid and 1 mL of ethanol. To the reaction mixture is finally added 24 mg of tetrakistriphenylphosphine palladium before heating at 80° C. for 10 hours. The cooled reaction mixture is then poured into ammonium chloride solution and extracted with ethyl acetate. The organic phase is washed with water and dried over magnesium sulfate. The solid residue after concentration is recrystallized into hexane to afford 70 mg of 1-Methyl-2-pyridin-4-yl-3-(3-trifluoromethyl-phenyl)-1H-pyrrolo[3,2-b]pyridine as white crystals.

Example 4

Preparation 1-(2-Fluoro-ethyl)-2-pyridin-4-yl-3-m-tolyl-1H-pyrrolo[3,2-b]pyridine following scheme 2

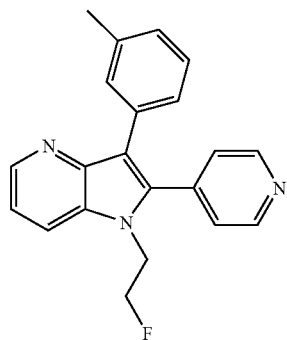

Step 1: Into 12 mL dimethylacetamide are added 240 mg (2 mmoles) of anhydrous magnesium sulfate, 1.3 mL (12 mmoles) of 4-acetyl pyridine, 515 mg (4 mmoles) of 3-amino-2-chloropyridine and 0.3 mL of acetic acid. The resulting suspension is kept under argon. Then 1.1 g (5.2 mmoles) of potassium phosphate and 202 mg (0.4 mmole) of bis-(tri-t-butylphosphine) palladium are added to the reaction mixture which is then sealed in its reaction vessel and stirred at 140° C. for 10 hours. The reaction mixture is poured into ammonium chloride solution and extracted with ethyl acetate. The organic phase is washed with water and dried over magnesium sulfate. The solid residue after concentration is purified by chromatography on silica gel (ethylacetate/methanol 9/1) to give 460 mg 2-pyridin-4-yl-1H-pyrrolo[3,2-b]pyridine as brown solid.

Step 2: 800 mg of N-bromosuccinimide (4 mmole) is added to a solution of 720 mg (3.7 mmoles) of 2-pyridin-4-yl-1H-pyrrolo[3,2-b]pyridine in tetrachloromethane. The brown reaction mixture is stirred 5 hours at 50° C. and concentrated. The brown residue is purified by chromatography on silica gel (ethylacetate/methanol 9/1) to give 650 mg of 3-Bromo-2-pyridin-4-yl-1H-pyrrolo[3,2-b]pyridine as white crystals.

Step 3: To a solution of 274 mg (1 mmole) of 3-Bromo-2-pyridin-4-yl-1H-pyrrolo[3,2-b]pyridine in 1.8 mL of toluene under nitrogen is added a 0.6 mL of a 2N solution of sodium carbonate, 170 mg (1.25 mmoles) of m-tolylboronic acid and 1.2 mL of ethanol. To the reaction mixture is finally added 45 mg of tetrakistriphenylphosphine palladium. The reaction mixture is sealed in a microwave vessel and stirred under microwave conditions at 180° C. for 2 min. The cooled reaction mixture is then poured into ammonium chloride solution and extracted with ethyl acetate. The organic phase is washed with water and dried over magnesium sulfate. The solid residue after concentration is recrystallized into hexane to afford 150 mg of 2-Pyridin-4-yl-3-m-tolyl-1H-pyrrolo[3,2-b]pyridine as white crystals.

Step 4: Sodium hydride (34 mg, 0.84 mmole 60% in oil) is added to a solution of 160 mg (0.56 mmole) of 2-Pyridin-4-yl-3-m-tolyl-1H-pyrrolo[3,2-b] in 6 mL of dimethylformamide at room temperature. After 30 min. at room temperature, 107 mg of 1-bromo-2-fluoroethane is added to the reaction mixture. After 20 hours at room temperature, the reaction mixture is poured into ammonium chloride solution and extracted with ethyl acetate. The organic phase is washed with water and dried over magnesium sulfate. The solid residue is purified by chromatography on silica gel (ethylacetate/methanol 9/1) to give 137 mg of 1-(2-Fluoro-ethyl)-2-pyridin-4-yl-3-m-tolyl-1H-pyrrolo[3,2-b]pyridine as white crystals.

Example 5

Preparation of 3-(4-Fluoro-phenyl)-1-methoxymethoxy-2-pyridin-4-yl-1H-pyrrolo[3,2-b]pyridine following scheme 4

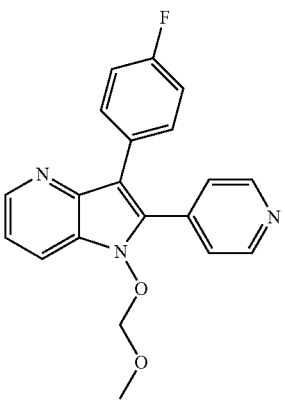

Step 1: 21.5 g (100 mmoles) of 2-(4-fluorophenyl)-1-(pyridine-4-yl)ethanone (prepared as described in scheme 1) and 34.9 g of 2-chloro-3-nitropyridine are dissolved in 270 mL of dimethylformamide. 8.8 g of sodium hydride (60% in oil (220 mmoles) is slowly added to the reaction mixture which is kept between 0 and 5° C. After stirring for 1 hour at room temperature, the reaction mixture is poured into 1 L of ammonium chloride solution and extracted with ethyl acetate. The organic phase is washed with water and dried over magnesium sulfate. The oily residue is purified by chromatography on silica gel (ethylacetate/hexane 1/1) to give 26.7 g of 2-(4-Fluoro-phenyl)-2-(3-nitro-pyridin-2-yl)-1-pyridin-4-yl-ethanone.

Step 2: 23 g (68.2 mmoles) of 2-(4-Fluoro-phenyl)-2-(3-nitro-pyridin-2-yl)-1-pyridin-4-yl-ethanone is dissolved in 700 mL of absolute ethanol. 2.2 g of 10% Palladium on charcoal is added to the solution which is stirred for 6 hours under a hydrogen atmosphere. The reaction mixture is filtered over celite, concentrated and the brown residue is purified by chromatography on silica gel (ethylacetate) to give 7 g of 3-(4-Fluoro-phenyl)-2-pyridin-4-yl-pyrrolo[3,2-b]pyridin-1-ol and 13 g of the starting material is recovered.

Step 3: Sodium hydride (30 mg, 0.72 mmole 60% in oil) is added to a solution of 200 mg (0.65 mmole) of 3-(4-Fluorophenyl)-2-pyridin-4-yl-pyrrolo[3,2-b]pyridin-1-ol in 6 mL of dimethylformamide at room temperature. After 30 min. at room temperature, 65 mg of chloromethyl methyl ether is added to the reaction mixture. After 1 hour at room temperature, the reaction mixture is poured into ammonium chloride solution and extracted with ethyl acetate. The organic phase is washed with water and dried over magnesium sulfate. The solid residue is purified by chromatography on silica gel (ethylacetate) to give 120 mg of 3-(4-Fluoro-phenyl)-1-methoxymethoxy-2-pyridin-4-yl-1H-pyrrolo[3,2-b]pyridine as white crystals.

Example 6

Preparation of 1-Allyl-2-(2-chloro-pyridin-4-yl)-3-(4-fluoro-phenyl)-1H-pyrrolo[3,2-b]pyridine following scheme 5

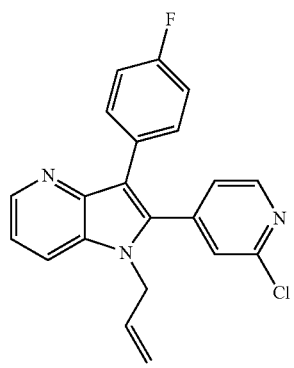

Step 1: 80 g (74.6 mmoles) of pyridine-4-carboxaldehyde is dissolved in 150 mL of methanol. 123.5 mL (112 mmoles) of trimethyl orthoformiate is added to the reaction mixture at room temperature followed by the addition of 33 mL of concentrated sulfuric acid. The reaction mixture is kept under reflux for 24 hours and once cooled, added to 300 mL of sodium methylate solution. The white suspension obtained is filtered over celite, the filtrate is concentrated under vacuum and 70.3 g of 4-dimethoxymethyl-pyridine is obtained as a yellow oil.

Step 2: 315 mL of n-butyllithium 1.6 M solution in hexane is added dropwise to a solution of 70.3 g (0.46 mole) of 4-dimethoxymethyl-pyridine in 1.4 L of tetrahydrofuran under nitrogen at −70° C. After 30 min. at −70° C., 73 g (0.505 mole) of 4-fluorobenzyl chloride in 280 mL of tetrahydrofuran is added dropwise. After 10 more min. at −70° C., the reaction mixture is allowed to reach room temperature and then stirred for 30 further min. The reaction mixture is poured into 2 L ammonium chloride solution and extracted with ethyl acetate. The organic phase is washed with water and dried over magnesium sulfate. After concentration the residue is purified by chromatography on silica gel (ethylacetate/hexane 1/1) to give 114 g of 4-[2-(4-Fluoro-phenyl)-1,1-dimethoxy-ethyl]-pyridine as yellow oil.

Step 3: 55 g (0.21 mole) of 4-[2-(4-Fluoro-phenyl)-1,1-dimethoxy-ethyl]-pyridine and 445 mg of methyltrioxorhenium are dissolved in 250 mL of dichloromethane. 112 mL of commercial hydrogen peroxide solution is added to the reaction mixture which is further stirred over night at room temperature. The reaction mixture is then decanted and the organic phase is washed with sodium hydrogen sulfate and water and dried over magnesium sulfate. After concentration, 33 g of 4-[2-(4-Fluoro-phenyl)-1,1-dimethoxy-ethyl]-pyridine 1-oxide is obtained as a green oil.

Step 4: 60 g (0.21 mole) of 4-[2-(4-Fluoro-phenyl)-1,1-dimethoxy-ethyl]-pyridine 1-oxide together with 27.9 g (0.21 mole) of 3-amino-2-chloro pyridine are heated under argon at 130° C. without solvent for 2 hours. After cooling and before complete crystallisation of the reaction mixture, ethyl acetate is added (150 mL) resulting in the formation of a white precipitate which is filtered to give 32 g of (2-Chloro-pyridin-3-yl)-[2-(4-fluoro-phenyl)-1-(1-oxy-pyridin-4-yl)-ethylidene]amine.

Step 5: 5.8 g (17 mmoles) of (2-Chloro-pyridin-3-yl)-[2-(4-fluoro-phenyl)-1-(1-oxy-pyridin-4-yl)-ethylidene]-amine is dissolved in 100 mL of dimethylformamide under nitrogen. 5.7 g of DABCO (51 mmoles) and 550 mg of bis(triphenylphosphine)palladium dichloride are subsequently added to the reaction mixture which is stirred for 3 hours at 120° C. The cooled reaction mixture is then poured into water and extracted with ethyl acetate. The organic phase is washed with water and dried over magnesium sulfate. The solid residue after concentration is recrystallized into ethyl acetate to afford 5.2 g of 3-(4-Fluoro-phenyl)-2-(1-oxy-pyridin-4-yl)-1H-pyrrolo[3,2-b]pyridine as a yellowish solid.

Step 6: 12.25 g (40.1 mmoles) of 3-(4-Fluoro-phenyl)-2-(1-oxy-pyridin-4-yl)-1H-pyrrolo[3,2-b]pyridine in 120 mL of phosphoroxychloride are stirred at 120° C. for 90 min. The reaction mixture is concentrated under vacuum and the residue treated with methanol and filtered over celite. After concentration of the methanol phase, the solid residue is purified by chromatography on silica gel (ethyl acetate/methanol 9/1) to give 10 g of 2-(2-Chloro-pyridin-4-yl)-3-(4-fluoro-phenyl)-1H-pyrrolo[3,2-b]pyridine as yellow solid.

Step 7: Sodium hydride (120 mg, 3 mmole 60% in oil) is added to a solution of 323.5 mg (1 mmole) of 2-(2-Chloro-pyridin-4-yl)-3-(4-fluoro-phenyl)-1H-pyrrolo[3,2-b]pyridine in 8 mL of dimethylformamide at room temperature. After 30 min. at room temperature, 1.2 g of allyl bromide (10 mmoles) is added to the reaction mixture. After 1 hour at room temperature, the reaction mixture is poured into ammonium chloride solution and extracted with ethyl acetate. The organic phase is washed with water and dried over magnesium sulfate. After concentration the solid residue is purified by chromatography on silica gel (ethyl acetate/hexane 1/1) to give 270 mg of 1-Allyl-2-(2-chloro-pyridin-4-yl)-3-(4-fluoro-phenyl)-1H-pyrrolo[3,2-b]pyridine as white solid.

Example 7

Preparation of 4-[3-(4-Fluoro-phenyl)-6-methyl-1H-pyrrolo[3,2-b]pyridin-2-yl]-pyridin-2-ylamine following scheme 1

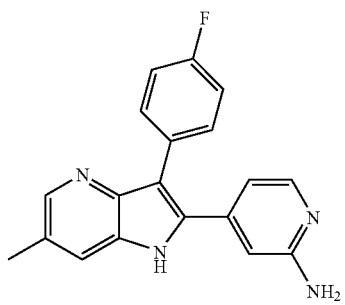

Step 1: To a solution of 15 g (0.105 mole) of 5-amino-6-chloro-3-picoline in 100 mL dimethylformamide is added 1 mL of concentrated sulfuric acid. Then a solution of 43.7 g (0.15 mole) of 4-[2-(4-Fluoro-phenyl)-1,1-dimethoxy-ethyl]-pyridine 1-oxide (as previously prepared in example 6) in 80 mL of dimethylformamide is slowly added to the reaction mixture which is subsequently warmed at 80° C. for 6 hours. Once cooled, the reaction mixture is poured into ammonium chloride solution and extracted with ethyl acetate. The organic phase is washed with water and dried over magnesium sulfate. After concentration the solid residue is purified by chromatography on silica gel (ethyl acetate/methanol 9/1) to give 16 g of (2-Chloro-5-methyl-pyridin-3-yl)-[2-(4-fluoro-phenyl)-1-(1-oxy-pyridin-4-yl)-ethylidene]-amine as white solid.

Step 2: 34.5 g (97 mmoles) of ((2-Chloro-5-methyl-pyridin-3-yl)-[2-(4-fluoro-phenyl)-1-(1-oxy-pyridin-4-yl)-ethylidene]-amine are dissolved in 600 mL of dimethylformamide under nitrogen. 33 g of DABCO (295 mmoles) and 3.5 g of bis(triphenylphosphine)palladium dichloride are subsequently added to the reaction mixture which is stirred for 3 hours at 120° C. The cooled reaction mixture is then poured into water and extracted with ethyl acetate. The organic phase is washed with water and dried over magnesium sulfate. The solid residue after concentration is recrystallized in diethyl ether to afford 17 g of 3-(4-Fluoro-phenyl)-6-methyl-2-(1-oxy-pyridin-4-yl)-1H-pyrrolo[3,2-b]pyridine as a yellowish solid.

Step 3: 15 g (47 mmoles) of 3-(4-Fluoro-phenyl)-6-methyl-2-(1-oxy-pyridin-4-yl)-1H-pyrrolo[3,2-b]pyridine in 150 mL of phosphoroxychloride are stirred at 120° C. for 1 hour. The reaction mixture is concentrated under vacuum and the residue treated with methanol and filtered over celite. After concentration of the methanol phase, the solid residue is purified by chromatography on silica gel (ethyl acetate/methanol 9/1) to give 11 g of 2-(2-Chloro-pyridin-4-yl)-3-(4-fluoro-phenyl)-6-methyl-1H-pyrrolo[3,2-b]pyridine as yellow solid.

Step 4: 11 g of 2-(2-Chloro-pyridin-4-yl)-3-(4-fluoro-phenyl)-6-methyl-1H-pyrrolo[3,2-b]pyridine are suspended in 115 ml of benzylamine. The reaction mixture is refluxed at 180° C. for 24 hours. After cooling, the reaction mixture is poured into hexane resulting in the formation of a yellow precipitate. After filtration the precipitate is suspended in hot water, filtrated again and washed with hot water resulting in the isolation of 9.55 g of Benzyl-{-4-[3-(4-fluoro-phenyl)-6-methyl-1H-pyrrolo[3,2-b]pyridin-2-yl]-pyridin-2-yl}-amine as a white solid.

Step 5: 7.8 g (19 mmoles) of Benzyl-{4-[3-(4-fluoro-phenyl)-6-methyl-1H-pyrrolo[3,2-b]pyridin-2-yl]-pyridin-2-yl}-amine is suspended at room temperature in 40 mL of concentrated sulfuric acid. After 1 hour, the reaction is poured into ice (250 g) and kept at 0° C. while adding 170 mL of concentrated sodium hydroxide solution to reach pH=10. The resulting precipitate is filtered, suspended again in hot water and stirred at reflux for 1 hour. The reaction mixture is then filtered again and washed with hot water to give 6 g of 4-[3-(4-Fluoro-phenyl)-6-methyl-1H-pyrrolo[3,2-b]pyridin-2-yl]-pyridin-2-ylamine as white solid.

Example 8

Preparation N-{4-[3-(4-Fluoro-phenyl)-6-methyl-1H-pyrrolo[3,2-b]pyridin-2-yl]-pyridin-2-yl}-malonamic acid methyl ester following scheme 5

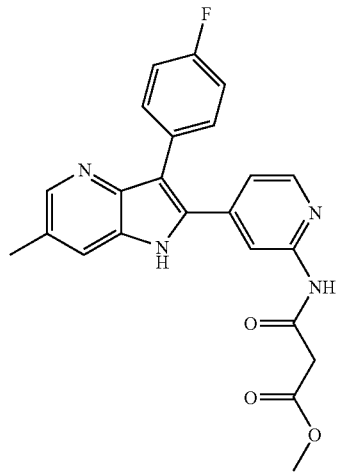

Chlorocarbonyl-acetic acid methyl ester (129 mg, 0.9 mmole) is added to a solution of 200 mg (0.62 mmole) of 4-[3-(4-Fluoro-phenyl)-6-methyl-1H-pyrrolo[3,2-b]pyridin-2-yl]-pyridin-2-ylamine (prepared following the procedure for example 7) in 3 mL of pyridine at room temperature. After 30 hours at room temperature, Chlorocarbonyl-acetic acid methyl ester (129 mg, 0.9 mmole) is added again to the reaction mixture stirred 12 more hours at room temperature. The reaction mixture is then poured into ammonium chloride solution and extracted with ethyl acetate. The organic phase is washed with water and dried over magnesium sulfate. After concentration the solid residue is purified by chromatography on silica gel (ethyl acetate) to give 40 mg of N-{4-[3-(4-

Fluoro-phenyl)-6-methyl-1H-pyrrolo[3,2-b]pyridin-2-yl]-pyridin-2-yl}-malonamic acid methyl ester as white solid.

Example 9

Preparation of {4-[1-(2-Fluoro-ethyl)-3-(4-fluoro-phenyl)-1H-pyrrolo[3,2-b]pyridin-2-yl]-pyridin-2-yl}-(3-fluoro-phenyl)-amine following scheme 5

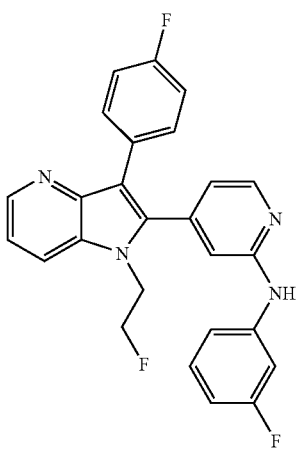

Step 1: Sodium hydride (371 mg, 9.3 mmoles 60% in oil) is added to a solution of 1 g (3.1 mmoles) of 2-(2-Chloro-pyridin-4-yl)-3-(4-fluoro-phenyl)-1H-pyrrolo[3,2-b]pyridine (prepared following the procedure for example 6) in 20 mL of dimethylformamide at room temperature. After 30 min. at room temperature, 2.75 g of 1-bromo-2-fluoro-ethane (21.6 mmoles) is added to the reaction mixture. After 10 hour at room temperature, the reaction mixture is poured into ammonium chloride solution and extracted with ethyl acetate. The organic phase is washed with water and dried over magnesium sulfate. After concentration the solid residue is purified by chromatography on silica gel (ethyl acetate/hexane 1/1) to give 720 mg of 2-(2-Chloro-pyridin-4-yl)-1-(2-fluoro-ethyl)-3-(4-fluoro-phenyl)-1H-pyrrolo[3,2-b]pyridine as white solid.

Step 2: In a 5 mL microwave vessel (Biotage) are weighted together 185 mg (0.5 mmole) of 2-(2-Chloro-pyridin-4-yl)-1-(2-fluoro-ethyl)-3-(4-fluoro-phenyl)-1H-pyrrolo[3,2-b]pyridine, 67 mg (0.6 mmoles) of 3-fluorophenyl amine, 2 mg of palladium acetate, 7 mg of biphenylyl dicyclohexylphosphine and 67 mg (0.7 mmole) of sodium t-butoxide in 2.5 mL of toluene. The reaction mixture is then heated at 180° C. for 10 min. under microwave conditions. The reaction mixture is poured into ammonium chloride solution and extracted with ethyl acetate. The organic phase is washed with water and dried over magnesium sulfate. After concentration the solid residue is purified by chromatography on silica gel (ethyl acetate/hexane 1/1) to give 85 mg of {4-[1-(2-Fluoro-ethyl)-3-(4-fluoro-phenyl)-1H-pyrrolo[3,2-b]pyridin-2-yl]-pyridin-2-yl}-(3-fluoro-phenyl)-amine as white solid.

Example 10

Preparation of 4-[3-(4-Fluoro-phenyl)-1H-pyrrolo[3,2-b]pyridin-2-yl]-pyridine-2-carboxylic acid amide following scheme 5

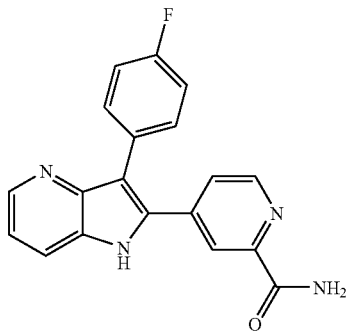

Step 1: Trimethylsilyl cyanide (10.3 mL, 82 mmoles) is added to a solution of 5.02 g (16.4 mmoles) of 3-(4-Fluoro-phenyl)-2-(1-oxy-pyridin-4-yl)-1H-pyrrolo[3,2-b]pyridine (as prepared in example 6) in 35 mL of dimethylformamide. Benzoyl chloride (3.8 mL, 33 mmoles) is then slowly added to the reaction mixture. After 8 hours, the reaction mixture is poured into ammonium chloride solution and extracted with ethyl acetate. The organic phase is washed with water and dried over magnesium sulfate. After concentration the solid residue is purified by chromatography on silica gel (ethyl acetate) to give 3.55 g of 4-[3-(4-Fluoro-phenyl)-1H-pyrrolo[3,2-b]pyridin-2-yl]-pyridine-2-carbonitrile as white solid.

Step 2: 1.44 g (4.6 mmoles) of 4-[3-(4-Fluoro-phenyl)-1H-pyrrolo[3,2-b]pyridin-2-yl]-pyridine-2-carbonitrile is stirred at room temperature in 8 mL of t-butanol in the presence of 1.03 g (18.3 mmoles) of powdered potassium hydroxide. The reaction is stirred at room temperature for 4 hours, concentrated under vacuum and poured into water and ethyl acetate (1/1). Chlorhydric acid 2N is added to the solution to reach pH=5 and the solution is extracted with ethyl acetate. The organic phase is washed with water and dried over magnesium sulfate. After concentration 800 mg of 4-[3-(4-Fluoro-phenyl)-1H-pyrrolo[3,2-b]pyridin-2-yl]-pyridine-2-carboxylic acid amide are obtained as white solid.

Example 11

Preparation of 3-(4-Fluoro-phenyl)-2-pyrimidin-4-yl-1H-pyrrolo[3,2-b]pyridine following scheme 1

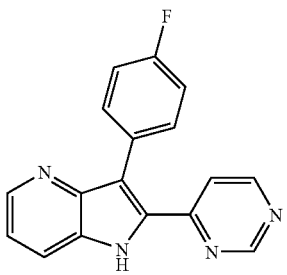

Step 1: 50 g (0.31 mole) of 4-chloro-2-methylthiopyrimidine is solubilised in 300 mL of hydriodic acid at room temperature. The reaction mixture is stirred at room temperature for 8 hours. The reaction mixture is poured into 1.2 L of water and the pH adjusted to 8 with solid sodium bicarbonate. The mixture is extracted with dichloromethane and washed with sodium thiosulfate. After concentration the oily residue gives 74 g of 4-iodo-2-methylthiopyrimidine.

Step 2: 20 g (79 mmoles) of 4-iodo-2-methylthiopyrimidine in 165 mL of tetrahydrofuran under argon is cooled to −70° C. 45.5 mL of isopropylmagnesium chloride (2M in THF) is then slowly added to the reaction mixture, keeping the temperature at −70° C. After 30 min., a solution of 4-fluorophenyl acetyl chloride (13.7 g, 79 mmoles) in 65 mL tetrahydrofuran is added dropwise to the reaction mixture which is further stirred at −78° C. for 1 hour and allowed to reach 0° C. After 30 min. at 0° C., the reaction is poured into ice-water and extracted with ethyl acetate. The organic phase is washed with water and dried over magnesium sulfate. After concentration the oily purified by chromatography on silica gel (ethyl acetate/hexane 4/1) affording 9.5 g of 2-(4-Fluoro-phenyl)-1-(2-methylthio-pyrimidin-4-yl)-ethanone as yellow oil.

Step 3: A mixture of p-toluenesulfonic acid (10 mg), 2-(4-Fluoro-phenyl)-1-(2-methylthio-pyrimidin-4-yl)-ethanone (200 mg, 0.76 mmoles) and 3-amino-2-chloropyridine (90 mg, 0.7 mmoles) in 3 mL of toluene was refluxed overnight with a Dean-Stark removal of water/toluene azeotrope. The reaction mixture was further concentrated, the brown residue suspended in an ethyl acetate/hexane mixture (9/1) and filtered. The solid was solubilised in ethyl acetate and purified by chromatography on silica gel (ethylacetate/hexane 1/1) to give 130 mg of (2-Chloro-pyridin-3-yl)-[2-(4-fluoro-phenyl)-1-(2-methylthio-pyrimidin-4-yl)-ethylidene]-amine as a brown oil.

Step 4: 6.5 g (14.7 mmoles) of (2-Chloro-pyridin-3-yl)-[2-(4-fluoro-phenyl)-1-(2-methylthio-pyrimidin-4-yl)-ethylidene]-amine is dissolved in 60 mL of dimethylformamide under nitrogen. 6.2 g of DABCO (52 mmoles) and 0.5 g of bis(triphenylphosphine)palladium dichloride are subsequently added to the reaction mixture which is stirred for 4 hours at 120° C. The cooled reaction mixture is then poured into water and extracted with ethyl acetate. The organic phase is washed with water and dried over magnesium sulfate. The solid residue after concentration is recrystallized in diethyl ether to afford 4 g of 3-(4-Fluoro-phenyl)-2-(2-methylthio-pyrimidin-4-yl)-1H-pyrrolo[3,2-b]pyridine as a yellowish solid.

Step 5: 560 mg (1.66 mmoles) of 3-(4-Fluoro-phenyl)-2-(2-methylthio-pyrimidin-4-yl)-1H-pyrrolo[3,2-b]pyridine is stirred at room temperature in a mixture of 50 mL of absolute ethanol and 40 mL of ammonia (15% in water). 2 g of Raney nickel (50% in water) is then added to the solution which is further stirred for 3 hours under refluxing conditions. Once cooled, the reaction mixture is filtered over celite and extracted with ethyl acetate. The organic phase is washed with water and dried over magnesium sulfate. The solid residue after concentration is solubilised in ethyl acetate and purified by chromatography on silica gel (ethylacetate/hexane 1/1) to give 250 mg of 3-(4-Fluoro-phenyl)-2-pyrimidin-4-yl-1H-pyrrolo[3,2-b]pyridine as yellowish solid.

Example 12

Preparation of {4-[3-(4-Fluoro-phenyl)-1-methoxymethyl-1H-pyrrolo[3,2-b]pyridin-2-yl]-pyrimidin-2-yl}-(2-methoxy-1-methyl-ethyl)-amine following scheme 1

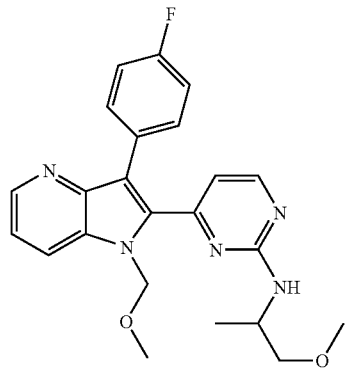

Step 1: Sodium hydride (130 mg, 2.8 mmoles 60% in oil) is added to a solution of 850 mg (2.53 mmoles) of 3-(4-Fluoro-phenyl)-2-(2-methylthio-pyrimidin-4-yl)-1H-pyrrolo[3,2-b]pyridine in 30 mL of dimethylformamide at room temperature. After 30 min. at room temperature, 0.23 mL of chloromethyl methyl ether is added to the reaction mixture. After 1 hour at room temperature, the reaction mixture is poured into ammonium chloride solution and extracted with ethyl acetate. The organic phase is washed with water and dried over magnesium sulfate. The solid residue is purified by chromatography on silica gel (ethyl acetate/hexane 2/1) to give 750 mg of 3-(4-Fluoro-phenyl)-1-methoxymethyl-2-(2-methylthio-pyrimidin-4-yl)-1H-pyrrolo[3,2-b]pyridine as white crystals.

Step 2: 730 mg (1.92 mmoles) of 3-(4-Fluoro-phenyl)-1-methoxymethyl-2-(2-methylthio-pyrimidin-4-yl)-1H-pyrrolo[3,2b]pyridine in 50 mL of dichloromethane is treated as 0° C. with 0.57 g of 3-chloroperbenzoic acid (2.3 mmoles). The reaction mixture is stirred 30 min. at 0° C. and poured into ice-water. The mixture is treated with sodium bicarbonate to reach a pH of between 8 and 9 and extracted with dichloromethane to give a yellow wax. 395 mg of this yellow wax is directly solubilised in 3 mL of 2-amino-1-methoxypropane and under microwave conditions heated at 200° C. for 20 min. The reaction mixture is poured into ammonium chloride solution and extracted with ethyl acetate. The organic phase is washed with water and dried over magnesium sulfate. The solid residue is purified by chromatography on silica gel (ethyl acetate/hexane 1/5) to give 350 mg of {-4-[3-(4-Fluoro-phenyl)-1-methoxymethyl-1H-pyrrolo[3,2-b]pyridin-2-yl]-pyrimidin-2-yl}-(2-methoxy-1-methyl-ethyl)-amine as yellowish wax.

Example 13

Biological Activity of the Compounds of the Invention

The compounds of the invention were tested in a leaf disk assay, as described below to determine their preventative action against a number of fungal species. In all cases, the test compounds were dissolved in DMSO and diluted into water to 200 ppm. The final test solution contained 2% DMSO and 0.025% Tween® 20.

a) *Erysiphe graminis* f.sp. *hordei* (barley powdery mildew) and *Pyrenophora teres* (barley net blotch): Barley leaf segments were placed on agar in a 24-well plate and sprayed with a solution of the test compound. After allowing the segments to dry completely (24 hours) they were inoculated with a spore suspension of the fungus. After appropriate incubation the activity of a compound was assessed four (*Pyrenophora teres*) or seven (*Erysiphe graminis* f.sp. *hordei*) days after inoculation as preventive fungicidal activity.

b) *Erysiphe graminis* f.sp. *tritici* (wheat powdery mildew), *Puccinia recondita* f.sp. *tritici* (wheat brown rust) and *Septoria nodorum* (wheat glume blotch): Wheat leaf segments were placed on agar in a 24-well plate and sprayed with a solution of the test compound. After allowing the segments to dry completely (24 hours), they were inoculated with a spore suspension of the fungus. After appropriate incubation the activity of a compound was assessed four (*Septoria nodorum*), seven (*Erysiphe graminis* f.sp. *tritici*) or eight (*Puccinia recondita* f.sp. *tritici*) days after inoculation as preventive fungicidal activity.

c) *Pyricularia oryzae* (rice blast): Rice leaf segments were placed on agar in a 24-well plate and sprayed with a solution of the test compound. After allowing the segments to dry completely (24 hours), they were inoculated with a spore suspension of the fungus. After appropriate incubation the activity of a compound was assessed five days after inoculation as preventive fungicidal activity.

d) *Botrytis cinerea* (grey mould): Bean leaf disks were placed on agar in a 24-well plate and sprayed with a solution of the test compound. After allowing the disks to dry completely (24 hours), they were inoculated with a spore suspension of the fungus. After appropriate incubation the activity of a compound was assessed three days after inoculation as preventive fungicidal activity.

e) *Phytophthora infestans* (late blight of potato/tomato): Tomato leaf disks were placed on water agar in a 24-well plate and sprayed with a solution of the test compound. After allowing the disks to dry completely (24 hours), they were inoculated with a spore suspension of the fungus. After appropriate incubation the activity of a compound was assessed four days after inoculation as preventive fungicidal activity.

f) *Plasmopara viticola* (downy mildew of grapevine): Grapevine leaf disks were placed on agar in a 24-well plate and sprayed a solution of the test compound. After allowing the disks to dry completely (for between 12 and 24 hours), they were inoculated with a spore suspension of the fungus. After appropriate incubation the activity of a compound was assessed seven days after inoculation as preventive fungicidal activity.

The following compounds (numbering corresponds to Tables 1, 2 and 3 above) gave at least 80% control of the following fungal infection at 200 ppm in the leaf disc assays described above:

*Plasmopara viticola:* 2; 3; 4; 5; 7; 9; 10; 13; 17; 18; 19; 21; 22; 28; 30; 33; 38; 39; 40; 41; 44; 48; 50; 51; 52; 53; 55; 56; 57; 58; 61; 63; 65; 66; 77; 78; 83; 84; 89; 97; 98; 99; 100; 101; 103; 104; 105; 106; 108; 109; 112; 113; 115; 118; 121; 124; 125; 126; 127; 129; 130; 132; 133; 135; 140; 151; 154; 155; 161; 162; 166; 167; 168; 169; 170; 171; 172; 173; 174; 175; 181; 182; 185; 195; 196; 203; 204; 207; 208; 212; 213; 214; 215; 216; 217; 222; 225; 226; 228; 233; 234; 265; 266; 267; 269; 276; 281; 282; 283; 284; 288; 289; 290; 292; 295; 296; 303; 304; 306; 308; 309; 329; 335; 337; 339; 342; 343; 350; 352; 373; 378; 396; 397; 401; 404; 409; 411; 412; 413; 437; 438; 445; 447; 448; 449; 451; 452; 453; 454; 455; 456 and 457.

*Phytophthora infestans:* 3; 13; 28; 38; 39; 40; 48; 50; 52; 54; 55; 56; 58; 59; 73; 77; 78; 84; 87; 89; 97; 98; 99; 101; 103; 104; 105; 108; 109; 110; 111; 112; 113; 114; 115; 118; 119; 121; 122; 124; 125; 126; 127; 128; 130; 132; 134; 139; 133; 135; 140; 141; 143; 145; 146; 147; 150; 151; 154; 162; 164; 166; 168; 169; 170; 171; 182; 187; 201; 203; 204; 205; 206; 207; 208; 211; 212; 213; 216; 217; 222; 225; 226; 246; 248; 252; 259; 260; 262; 264; 265; 276; 277; 278; 281; 282; 283; 284; 285; 290; 292; 306; 342; 343; 378; 397; 409; 411; 412; 413; 445; 447; 448; 451; 452; 453; 454; 455 and 456.

*Erysiphe graminis* f.sp. *tritici:* 3; 4; 7; 13; 28; 191; 201; 203; 205; 206; 207; 208; 212; 213; 216; 217; 220; 222; 224; 226; 234; 235; 238; 246; 248; 252; 253; 258; 259; 260; 261; 264; 265; 255; 278; 282; 283; 284; 288; 289; 290; 292; 315; 396; 401; 403; 404; 405; 408; 409; 411; 412; 413; 423; 426; 427; 435; 437; 447; 448; 449; 450; 451; 452; 453; 454; 455; 456 and 457.

*Botrytis cinerea:* 4; 6; 30; 56; 66; 93; 97; 98; 100; 101; 104; 105; 119; 123; 127; 133; 135; 139; 140; 143; 151; 166; 167; 173; 207; 211; 212; 213; 216; 222; 225; 228; 255; 258; 260; 262; 263; 265; 266; 269; 292; 306; 398 and 405.

*Puccinia recondita* f.sp. *tritici:* 3; 4; 7; 10; 17; 18; 19; 30; 37; 38; 39; 40; 43; 51; 52; 54; 55; 57; 66; 77; 78; 83; 84; 87; 89; 93; 96; 97; 98; 100; 101; 103; 104; 107; 108; 110; 119; 121; 125; 126; 127; 128; 129; 130; 135; 136; 143; 151; 154; 155; 162; 164; 166; 167; 168; 169; 170; 171; 172; 173; 174; 175; 204; 205; 206; 207; 208; 211; 212; 213; 215; 216; 217; 219; 220; 222; 225; 226; 228; 234; 235; 238; 244; 245; 246; 248; 252; 253; 255; 258; 259; 260; 261; 262; 263; 264; 265; 267; 277; 278; 282; 283; 288; 289; 294; 295; 303; 319; 337; 342; 343; 369; 373; 378; 395; 396; 401; 403; 404; 405; 408; 409; 411; 412; 413; 423; 424; 427; 432; 433; 437; 448; 449; 450; 451; 452; 453; 454; 455; 456; 457 and 447.

In addition, the compounds of the invention were also tested for their ability to inhibit the growth of fungal spores in nutrient broth.

a) *Septoria tritici* (wheat leaf blotch), *Botrytis cinerea* (grey mould), *Pyricularia oryzae* (rice blast), *Rhizoctonia solani* (foot rot and damping off), *Fusarium culmorum* (foot rot of cereals): Conidia of the fungus from cryogenic storage were directly mixed into nutrient broth (PDB potato dextrose broth). After placing a (DMSO) solution of the test compounds at 20 ppm into a microtiter plate (96-well format) the nutrient broth containing the fungal spores was added. The test plates were incubated at 24 C and the inhibition of growth was determined photometrically after 72 hrs (*Septoria tritici, Botrytis cinerea, Pyricularia oryzae*) or 48 hrs (*Rhizoctonia solani, Fusarium culmorum*).

b) *Pythium ultimum* (Damping off): Mycelial fragments of the fungus, prepared from a fresh liquid culture, were mixed into potato dextrose broth. A (DMSO) solution of the test compound at 20 ppm was then placed into a 96-well microtiter plate and the nutrient broth containing the fungal spores was added. The test plate was incubated at 24° C. and the inhibition of growth was determined photometrically after 48 hours.

The following compounds (numbering corresponds to Tables 1, 2 and 3 above) gave at least 80% control of the following fungal infection at 20 ppm in the liquid culture assays described above:

*Septoria tritici:* 4; 6; 7; 8; 10; 11; 13; 14; 17; 18; 26; 30; 33; 37; 38; 43; 47; 48; 52; 53; 54; 56; 57; 58; 59; 60; 62; 77; 78; 83; 84; 87; 89; 93; 96; 97; 98; 99; 100; 101; 103; 104; 105; 107; 108; 119; 126; 127; 128; 136; 142; 143; 156; 162; 166;

167; 168; 169; 170; 171; 172; 178; 181; 191; 193; 195; 196; 201; 204; 205; 207; 210; 216; 217; 219; 220; 222; 225; 226; 228; 234; 245; 246; 248; 252; 255; 257; 258; 259; 261; 263; 264; 265; 267; 276; 278; 282; 284; 285; 303; 306; 307; 327; 329; 339; 342; 343; 352; 369; 373; 378; 382; 389; 395; 396; 397; 398; 401; 404; 405; 408; 409; 411; 412; 413; 419; 420; 422; 423; 427; 428; 429; 431; 433; 437; 448; 449; 450; 451; 452; 453; 454; 455; 456; and 457.

*Pyricularia oryzae:* 4; 7; 13; 14; 26; 30; 33; 37; 38; 40; 43; 48; 56; 60; 83; 84; 92; 96; 97; 99; 100; 103; 104; 107; 108; 119; 123; 126; 127; 135; 136; 142; 143; 178; 181; 189; 191; 192; 194; 195; 196; 200; 201; 209; 216; 217; 219; 220; 222; 225; 226; 228; 278; 280; 282 and 306.

*Pythium ultimum:* 4; 6; 7; 8; 10; 13; 16; 17; 18; 27; 30; 38; 40; 43; 48; 50; 52; 53; 54; 55; 57; 58; 59; 62; 73; 76; 77; 78; 89; 91; 93; 97; 98; 99; 100; 101; 103; 104; 105; 106; 107; 108; 109; 110; 111; 112; 113; 115; 117; 119; 121; 123; 124; 125; 126; 127; 129; 130; 132; 133; 134; 135; 136; 139; 141; 143; 145; 146; 147; 148; 149; 150; 151; 152; 154; 155; 162; 166; 167; 168; 169; 170; 171; 172; 175; 195; 196; 197; 201; 203; 204; 205; 206; 207; 208; 210; 212; 216; 217; 219; 220; 222; 224; 225; 226; 234; 244; 245; 248; 251; 255; 256; 257; 258; 259; 260; 261; 262; 263; 264; 265; 266; 267; 269; 276; 278; 282; 283; 284; 288; 289; 307; 308; 329; 337; 339; 342; 343; 348; 352; 369; 373; 378; 394; 396; 397; 398; 400; 401; 404; 405; 408; 409; 411; 412; 413; 420; 427; 429; 432; 433; 435; 436; 437; 445; 448; 449; 450; 451; 452; 453; 454; 455; 456; 457; 395; 399; 402; 403 and 447.

*Fusarium culmorum:* 4; 6; 7; 10; 13; 38; 40; 43; 84; 97; 104; 128; 133; 162; 166; 168; 169; 216; 217; 220; 222; 234; 248; 255; 259; 264; 265; 278; 397; 398; 409; 413; 404; 405; 411; 412; 449 and 452.

Example 14

HPLC Methods Used

Method A (Water Alliance 2795 LC) with the following HPLC gradient conditions:
Solvent A: 0.1% formic acid in water/acetonitrile (9:1)
Solvent B: 0.1% formic acid in acetonitrile)

| Time (minutes) | A (%) | B (%) | Flow rate (ml/min) |
|---|---|---|---|
| 0 | 90 | 10 | 1.7 |
| 2.5 | 0 | 100 | 1.7 |
| 2.8 | 0 | 100 | 1.7 |
| 2.9 | 90 | 10 | 1.7 |

Type of column: Water atlantis dc18; Column length: 20 mm; Internal diameter of column: 3 mm; Particle Size: 3 micron; Temperature: 40° C.

The characteristic values obtained for each compound were the retention time ("RT", recorded in minutes) and the molecular ion, typically the cation $MH^+$ as listed in Tables 1, 2 and 3. The HPLC-MS method used is indicated in brackets.

Method B (Agilent1100 Series LC) with the following HPLC gradient conditions:
Solvent A: 0.1% formic acid in water/acetonitrile (9:1)
Solvent B: 0.1% formic acid in acetonitrile)

| Time (minutes) | A (%) | B (%) | Flow rate (ml/min) |
|---|---|---|---|
| 0 | 90 | 10 | 1.7 |
| 2.5 | 0 | 100 | 1.7 |
| 2.8 | 0 | 100 | 1.7 |
| 2.9 | 90 | 10 | 1.7 |

Type of column: Water atlantis dc18; Column length: 20 mm; Internal diameter of column: 3 mm; Particle Size: 3 micron; Temperature: 40° C.

The characteristic values obtained for each compound were the retention time ("RT", recorded in minutes) and the molecular ion, typically the cation $MH^+$ as listed in Tables 1, 2 and 3. The HPLC-MS method used is indicated in brackets.

Although the invention has been described with reference to preferred embodiments and examples thereof, the scope of the present invention is not limited only to those described embodiments. As will be apparent to persons skilled in the art, modifications and adaptations to the above-described invention can be made without departing from the spirit and scope of the invention, which is defined and circumscribed by the appended claims. All publications cited herein are hereby incorporated by reference in their entirety for all purposes to the same extent as if each individual publication were specifically and individually indicated to be so incorporated by reference.

The invention claimed is:

1. A method of preventing and/or controlling fungal infection in plants and/or plant propagation material comprising applying to the plant or plant propagation material a fungicidally effective amount of a compound of formula (I):

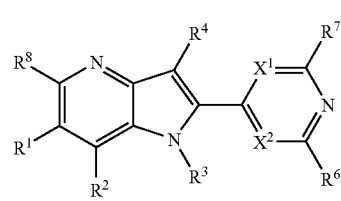

wherein:
$X^1$ is CH;
$X^2$ is CH;
$R^1$ is hydrogen, methyl, or chloro;
$R^2$ is hydrogen or methyl;
$R^3$ is hydrogen, cyanomethyl, aminoethyl, aminopropyl, pro-2-enyl, pro-2-ynyl, propa-1,2-dienyl, methoxymethyl, 2-fluoroethyl, —OCH2CCH, —OCH2OCH3, —OCH2CN, —OCH(CH3)CN;
$R^4$ is phenyl or 4-fluorophenyl:
(iv)
(iii)
$R^6$ is hydrogen or —NHCOR$^{23}$;
$R^7$ and $R^8$ are hydrogen; and
$R^{23}$ is methyl, ethyl, isopropyl, methoxy, C2-6alkenyl, cyclopropyl, cyclobutyl, methylcyclopropyl or methylcyclobutyl
or a salt of N-oxide thereof.

2. The method of claim 1, wherein $R^1$ is hydrogen.

3. The method of claim 1, wherein $R^2$ is hydrogen.

4. The method of claim 1, wherein $R^3$ is hydrogen.

5. The method of claim 1, wherein the fungal infection is a *Botrytis cinerea, Pyricularia oryzae, Fusarium culmorum, Septoria nodurum* and *Septoria tritici, Rhizoctonia solani, Puccinia recondite, Erysiphe graminis, Pyrenophora teres, Phytophthora infestans, Pythium ultimum* or *Plasmopara viticola* infection.

* * * * *